(12) United States Patent
Green et al.

(10) Patent No.: US 8,716,014 B2
(45) Date of Patent: May 6, 2014

(54) ADENOVIRUS E1A FRAGMENTS FOR USE IN ANTI-CANCER THERAPIES

(75) Inventors: Maurice Green, Wildwood, MO (US); Paul M. Loewenstein, Sain Louis, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 13/552,407

(22) Filed: Jul. 18, 2012

(65) Prior Publication Data

US 2013/0023481 A1 Jan. 24, 2013

Related U.S. Application Data

(60) Provisional application No. 61/509,891, filed on Jul. 20, 2011.

(51) Int. Cl.
*A61K 39/235* (2006.01)
(52) U.S. Cl.
USPC ..................... 435/320.1; 424/93.3
(58) Field of Classification Search
CPC ................ A61K 48/00; A61K 38/00; C12N 2710/10322; C12N 2710/10332; C07K 14/005
See application file for complete search history.

(56) References Cited

U.S. PATENT DOCUMENTS

| 7,883,888 B2 | 2/2011 | Michl et al. |
| 2004/0053863 A1 | 3/2004 | Hung et al. |
| 2009/0232732 A1 | 9/2009 | Simon et al. |
| 2010/0316635 A1 | 12/2010 | Lee et al. |

OTHER PUBLICATIONS

Boyd et al., "Adenovirus E1A N-terminal amino acid sequence requirements for repression of transcription in vitro and in vivo correlate with those required for E1A interference with TBP-TATA complex formation", *J. Virol.*, 76:1461-1474, 2002.
Chen et al., "Mapping of adenovirus 5 E1A domains responsible for suppression of neu-mediated transformation via transcriptional repression of neu", *Oncogene*, 14:1965-1971, 1997.
Green and Loewenstein, "Human adenoviruses: propagation, purification, quantification, and storage", *Curr. Prot. Micro.*, 14C.1-14C.19, 2005.
Green et al., "Adenovirus E1A proteins are closely associated with chromatin in productively infected and transformed cells", *Virology*, 371:1-7, 2008.
Green et al., "The transcription-repression domain of the adenovirus E1A oncoprotein targets p300 at the promoter", *Oncogene*, 27:4446-4455, 2008.
Hortobagyi et al., "Cationic liposome-mediated E1A gene transfer to human breast and ovarian cancer cells and its biologic effects: a phase I clinical trial", *Journal of Clinical Oncology*, 19(14):3422-3433, 2001.
Loewenstein and Green, "Expression of the adenovirus early gene IA transcription-repression domain alone downregulates HER2 and results in the death of human breast cancer cells upregulated for the HER2 proto-oncogene", *Genes & Cancer*, 2(7):737-744, 2011.
Loewenstein et al., "Mutational and functional analysis of an essential subdomain of the adenovirus E1A N-terminal transcription repression domain", *Virology*, 351:312-321, 2006.
Loewenstein et al., "The adenovirus E1A N-terminal repression domain represses transcription from a chromatic template in vitro", *Virology*, 428(1):70-5, 2012.
PCT International Search Report and Written Opinion issued in International Application No. PCT/US2012/47198, mailed Oct. 4, 2012.
Song et al., "Repression in vitro, by human adenovirus E1A protein domains, of basal or Tat-activated transcription of the human immunodeficiency virus type I long terminal repeat", *J. Virol.*, 69:2907-2911, 1995.
Song et al., "The adenovirus E1A repression domain disrupts the interaction between the TATA binding protein and the TATA box in a manner reversible by TFIIB", *Molecular and Cellular Biology*, 17(4):2186-93, 1997.
Song et al., "Transcription factor TFIID is a direct functional target of the adenovirus E1A transcription-repression domain," *Proc. Natl. Acad. Sci. USA*, 92:10330-10333, 1995.
Song et al., "Transcriptional repression by human adenovirus E1A N terminus/conserved domain 1 polypeptides in vivo and in vitro in the absence of protein synthesis", *The Journal of Biological Chemistry*, 270(40):23263-23267, 1995.
Xing et al., "Safety study and characterization of E1A-liposmes complex gene-delivery protocol in an ovarian cancer model", *Gene Therapy*, 5:1538-1544, 1998.
Yu et al., "Liposome-mediated in vivo E1A gene transfer suppressed dissemination of ovarian cancer cells that overexpress HER-2/neu", *Oncogene*, 11(7):1383-1388, 1995.
Zhang et al., "HER-2/neu-targeting cancer therapy via adenovirus-mediated E1A delivery in an animal model", *Oncogene*, 10(10):1947-1954, 1995.

*Primary Examiner* — Bao Li
(74) *Attorney, Agent, or Firm* — Parker Highlander PLLC

(57) ABSTRACT

The present invention relates to an improved cancer therapy comprising co-administration with the E1A 1-80 transcription-repression domain activity. In addition, E1A 1-80 can act as a monotherapy against cancers that express elevated HER2/Neu or in combination with anti-HER2/Neu, chemo- or radiotherapeutic treatments.

23 Claims, 16 Drawing Sheets

A.
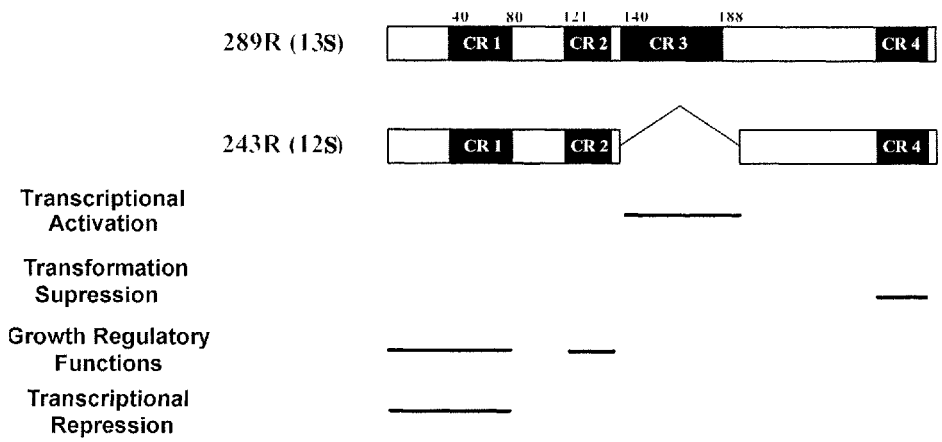
B.
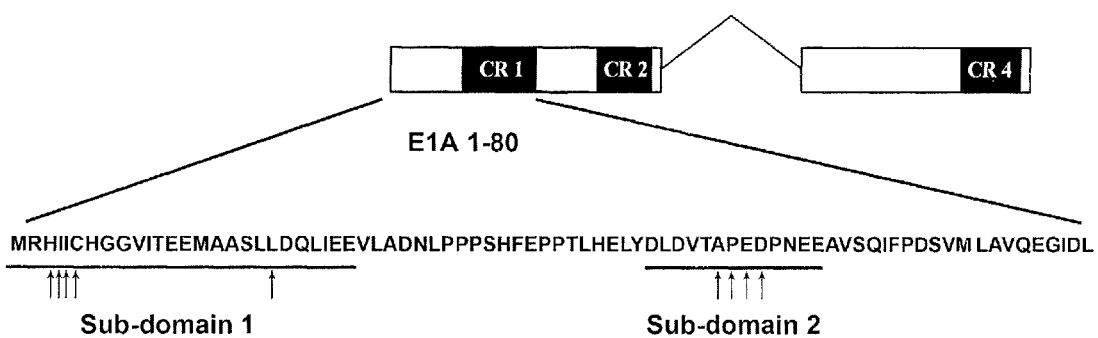
FIG. 1A-B

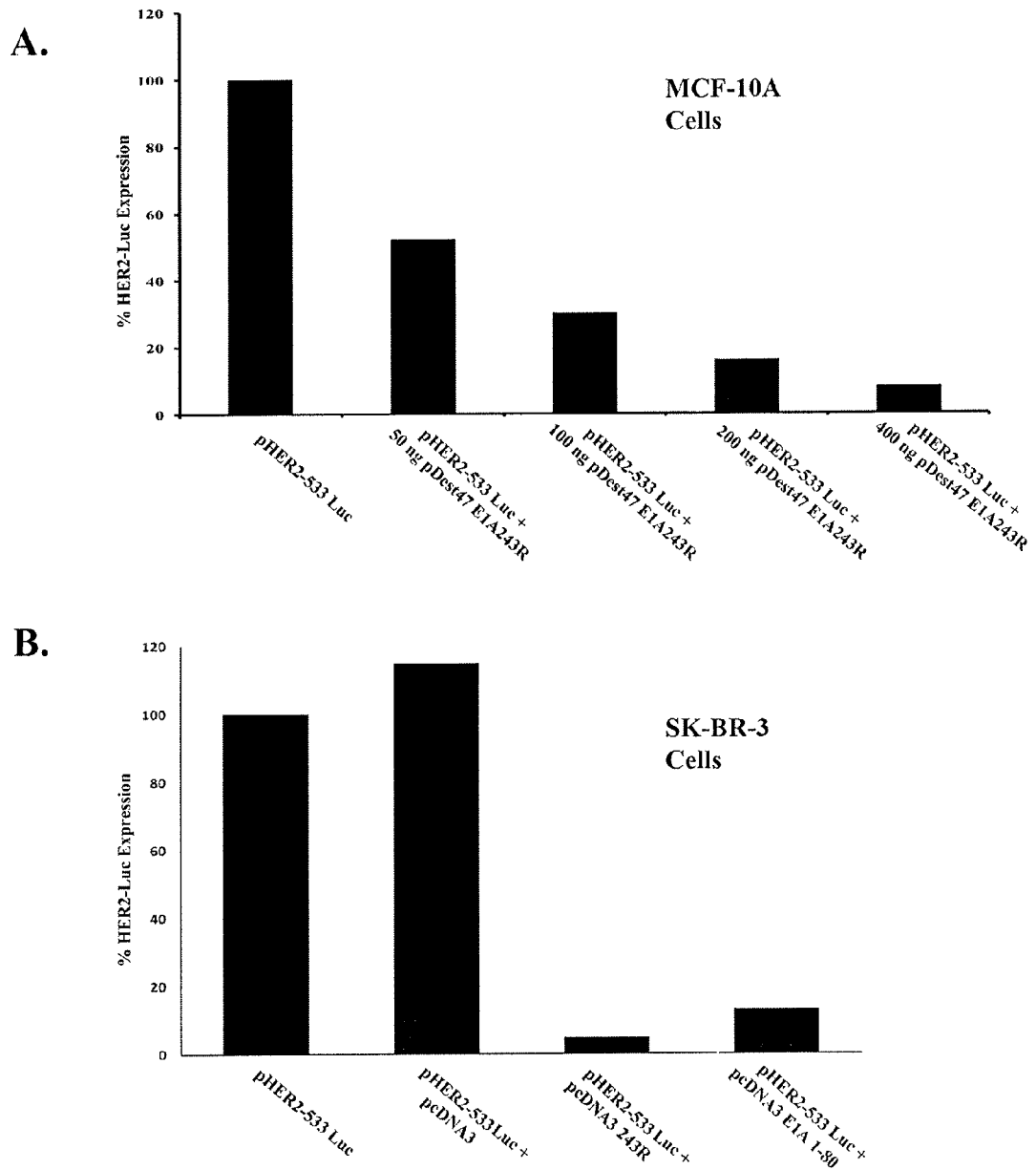
FIG. 2A-B

A.
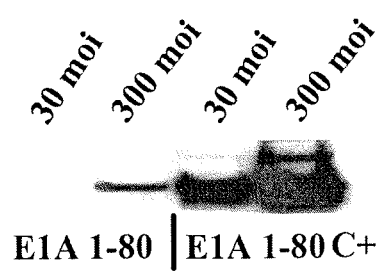
B.
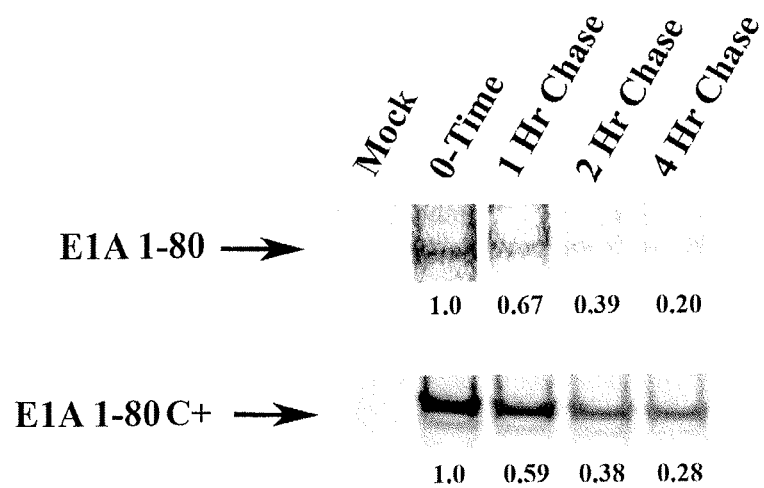
FIG. 4A-B

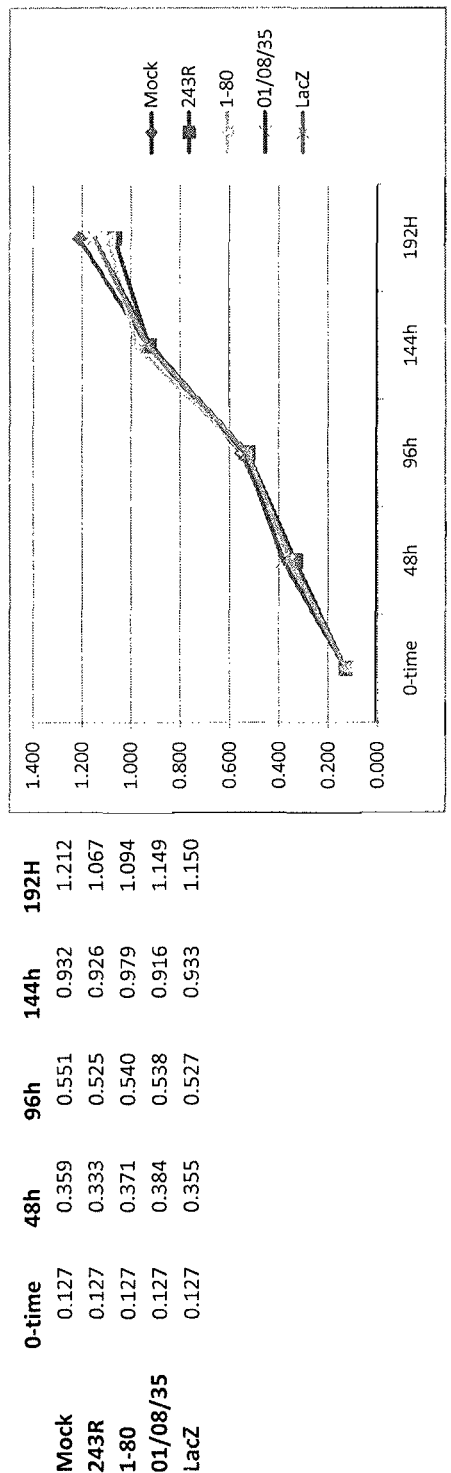
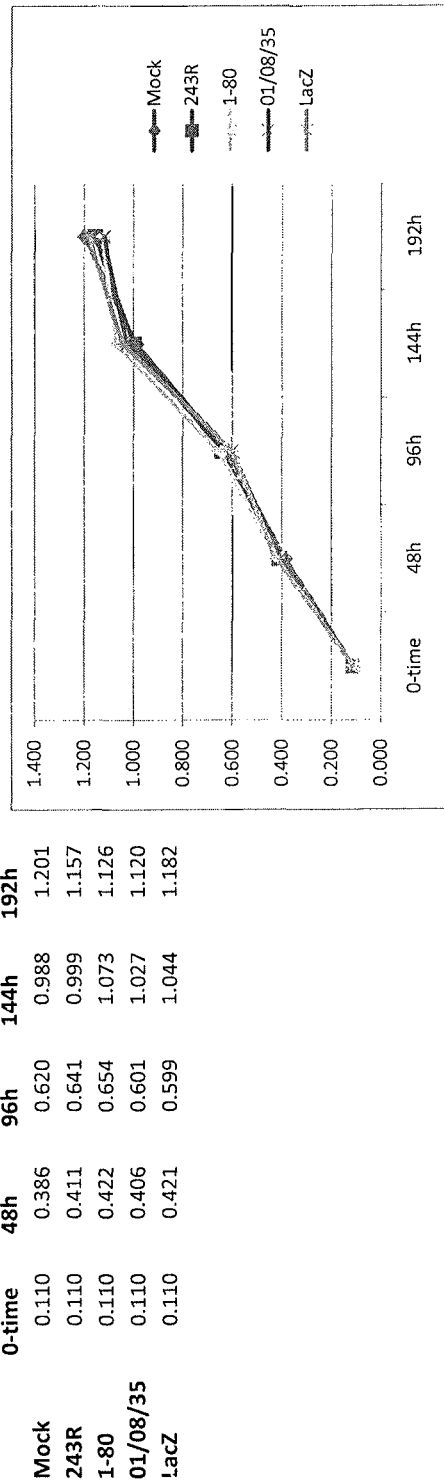

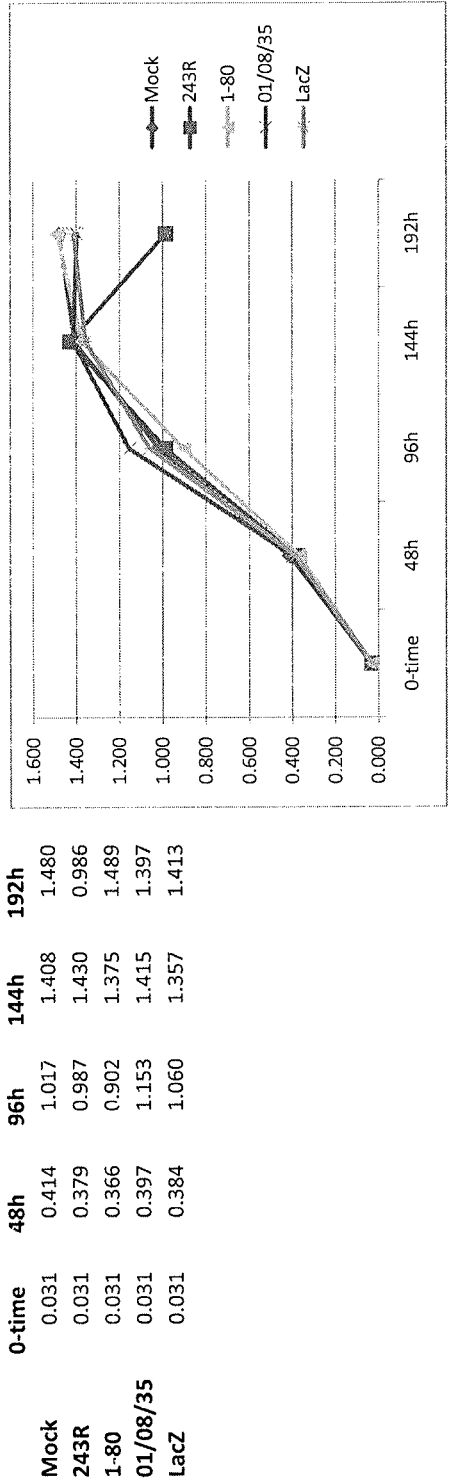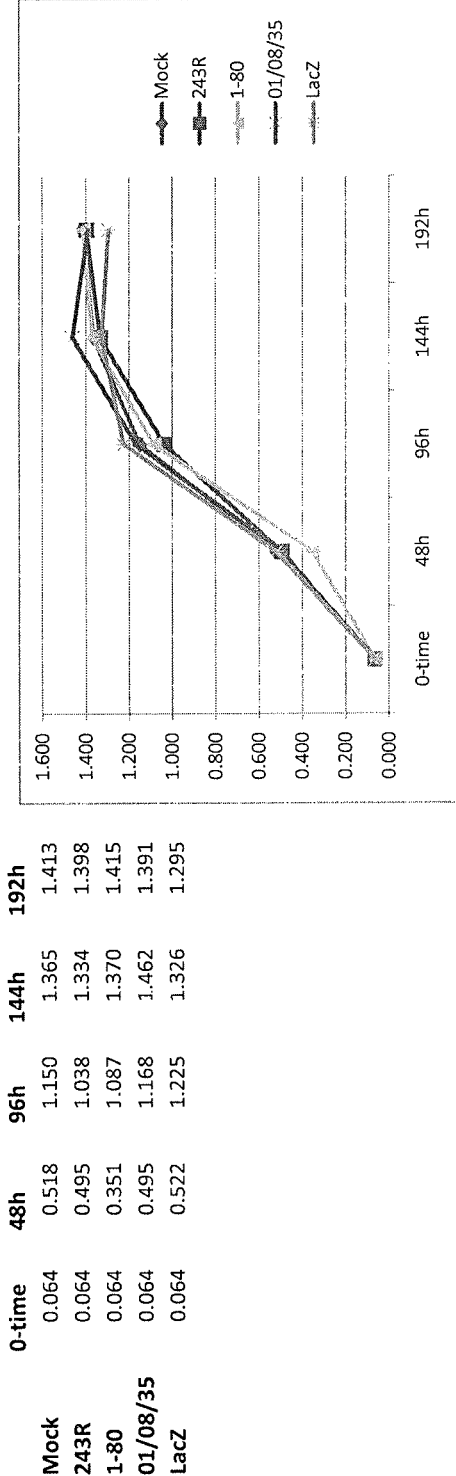
|  | 0-time | 48h | 96h | 144h | 192h |
|---|---|---|---|---|---|
| Mock | 0.031 | 0.414 | 1.017 | 1.408 | 1.480 |
| 243R | 0.031 | 0.379 | 0.987 | 1.430 | 0.986 |
| 1-80 | 0.031 | 0.366 | 0.902 | 1.375 | 1.489 |
| 01/08/35 | 0.031 | 0.397 | 1.153 | 1.415 | 1.397 |
| LacZ | 0.031 | 0.384 | 1.060 | 1.357 | 1.413 |
Fig 6C Normal Breast MCF 12A - Virus Alone: Average of 3 Experiments
|  | 0-time | 48h | 96h | 144h | 192h |
|---|---|---|---|---|---|
| Mock | 0.064 | 0.518 | 1.150 | 1.365 | 1.413 |
| 243R | 0.064 | 0.495 | 1.038 | 1.334 | 1.398 |
| 1-80 | 0.064 | 0.351 | 1.087 | 1.370 | 1.415 |
| 01/08/35 | 0.064 | 0.495 | 1.168 | 1.462 | 1.391 |
| LacZ | 0.064 | 0.522 | 1.225 | 1.326 | 1.295 |
Fig 6D Normal Breast MCF10A - Virus Alone: Average of 3 Experiments

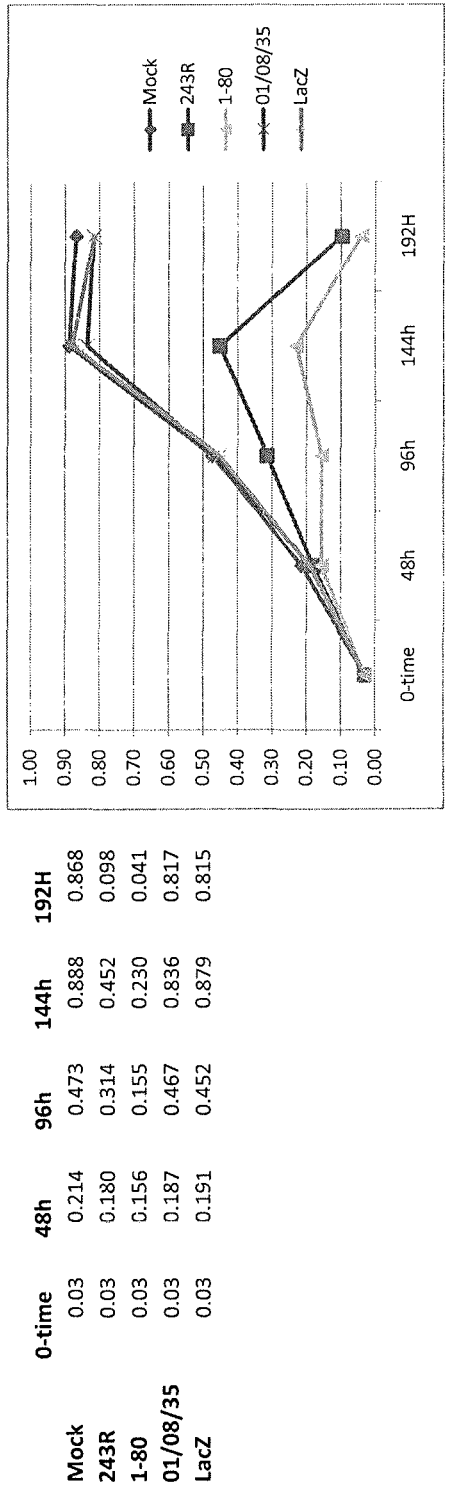
Fig 6E  Adenocarcinima of the colon SW620 - Virus Alone: Average of 3 Experiments
|          | 0-time | 48h   | 96h   | 144h  | 192H  |
|----------|--------|-------|-------|-------|-------|
| Mock     | 0.03   | 0.214 | 0.473 | 0.888 | 0.868 |
| 243R     | 0.03   | 0.180 | 0.314 | 0.452 | 0.098 |
| 1-80     | 0.03   | 0.156 | 0.155 | 0.230 | 0.041 |
| 01/08/35 | 0.03   | 0.187 | 0.467 | 0.836 | 0.817 |
| LacZ     | 0.03   | 0.191 | 0.452 | 0.879 | 0.815 |
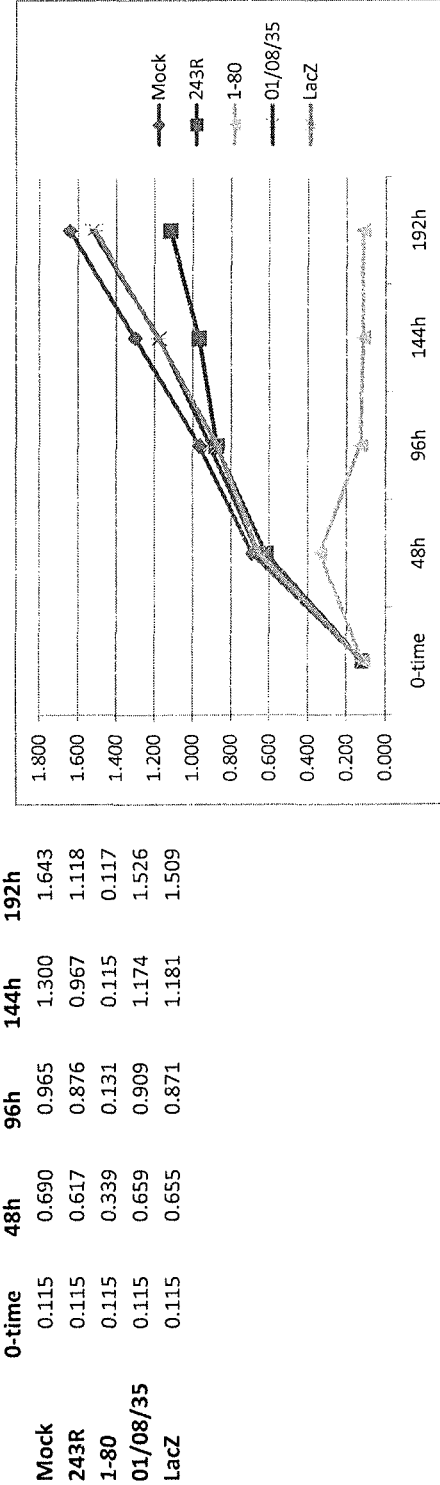
Fig 6F  Carcinima of the lung A549 - Virus Alone: Average of 3 Experiments
|          | 0-time | 48h   | 96h   | 144h  | 192h  |
|----------|--------|-------|-------|-------|-------|
| Mock     | 0.115  | 0.690 | 0.965 | 1.300 | 1.643 |
| 243R     | 0.115  | 0.617 | 0.876 | 0.967 | 1.118 |
| 1-80     | 0.115  | 0.339 | 0.131 | 0.115 | 0.117 |
| 01/08/35 | 0.115  | 0.659 | 0.909 | 1.174 | 1.526 |
| LacZ     | 0.115  | 0.655 | 0.871 | 1.181 | 1.509 |

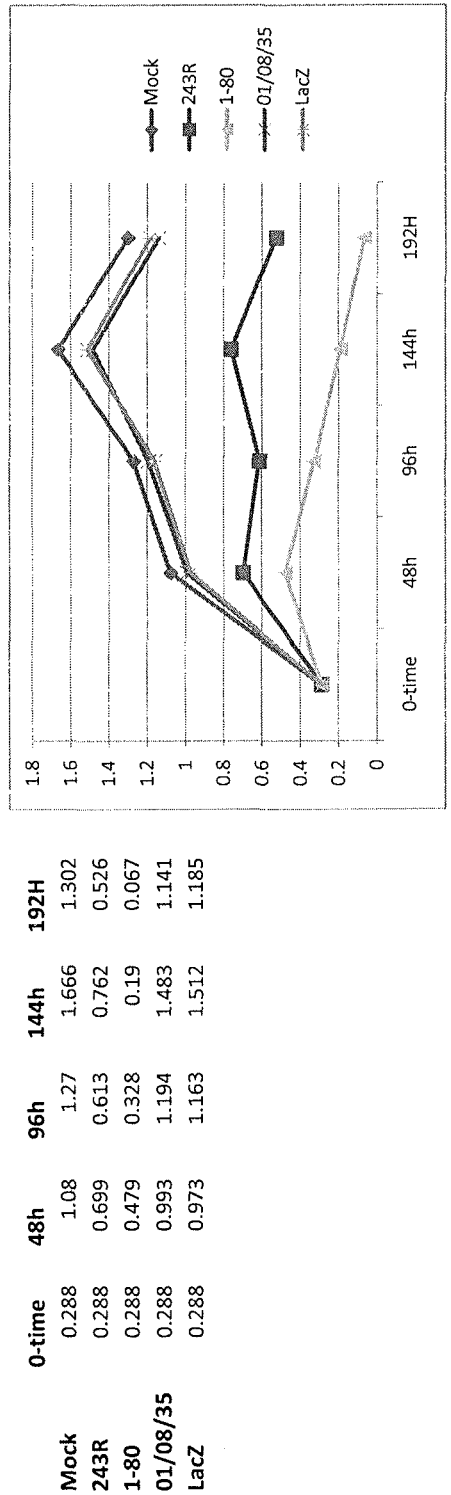
Fig 6G  Carcinoma of the lung NCI460 - Virus Alone: Average of 3 Experiments
|  | 0-time | 48h | 96h | 144h | 192H |
|---|---|---|---|---|---|
| Mock | 0.288 | 1.08 | 1.27 | 1.666 | 1.302 |
| 243R | 0.288 | 0.699 | 0.613 | 0.762 | 0.526 |
| 1-80 | 0.288 | 0.479 | 0.328 | 0.19 | 0.067 |
| 01/08/35 | 0.288 | 0.993 | 1.194 | 1.483 | 1.141 |
| LacZ | 0.288 | 0.973 | 1.163 | 1.512 | 1.185 |
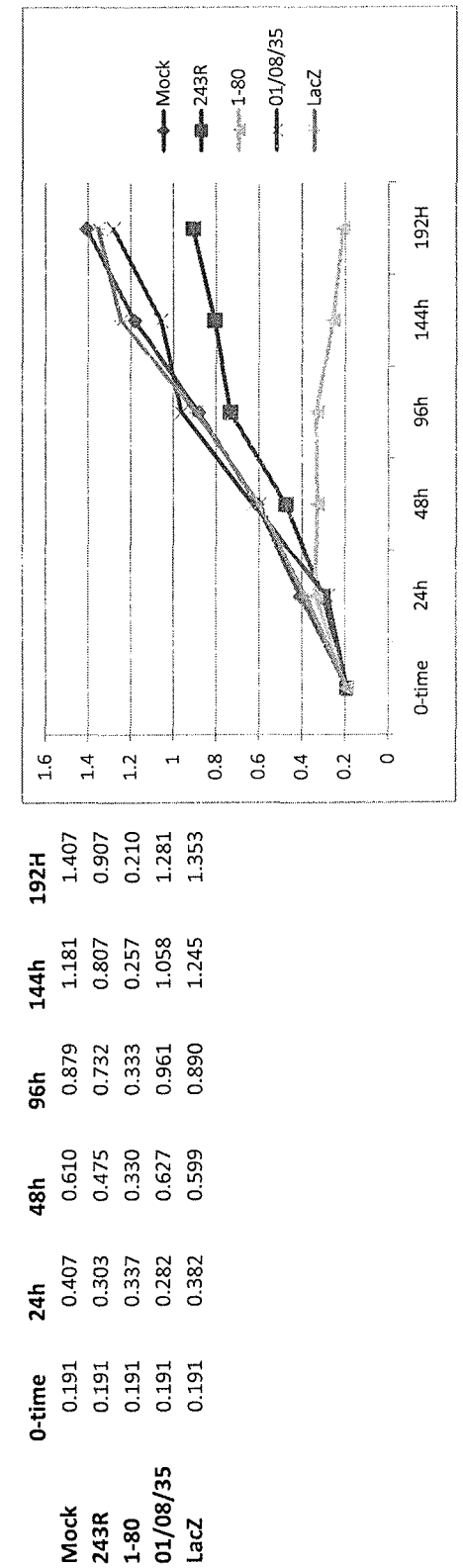
Fig 6H  Adenocarcinoma of the breast SKBR3 - Virus Alone: Average of 3 Experiments
|  | 0-time | 24h | 48h | 96h | 144h | 192H |
|---|---|---|---|---|---|---|
| Mock | 0.191 | 0.407 | 0.610 | 0.879 | 1.181 | 1.407 |
| 243R | 0.191 | 0.303 | 0.475 | 0.732 | 0.807 | 0.907 |
| 1-80 | 0.191 | 0.337 | 0.330 | 0.333 | 0.257 | 0.210 |
| 01/08/35 | 0.191 | 0.282 | 0.627 | 0.961 | 1.058 | 1.281 |
| LacZ | 0.191 | 0.382 | 0.599 | 0.890 | 1.245 | 1.353 |

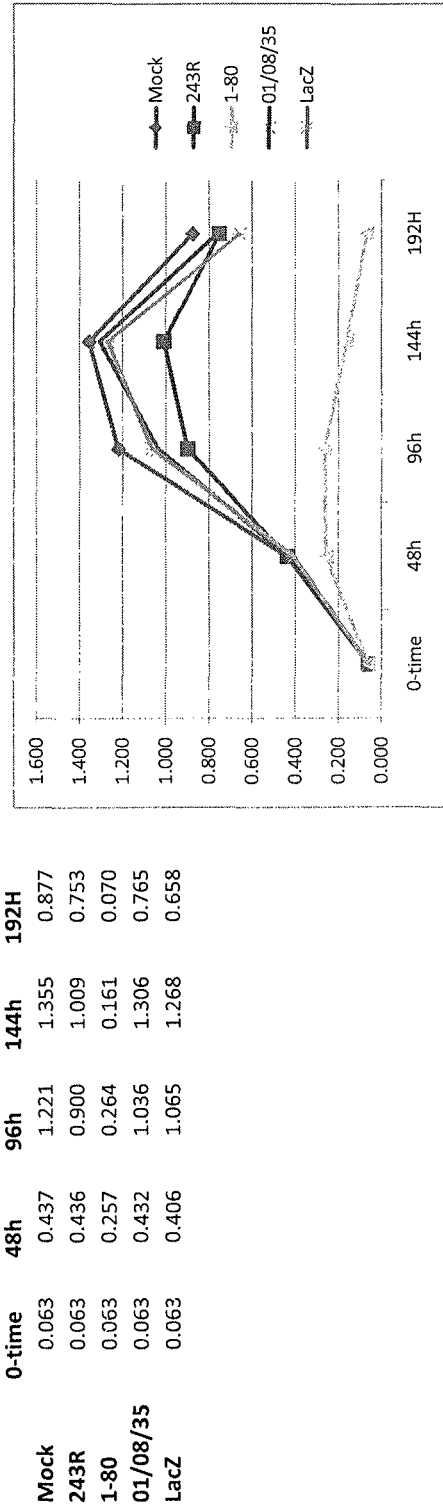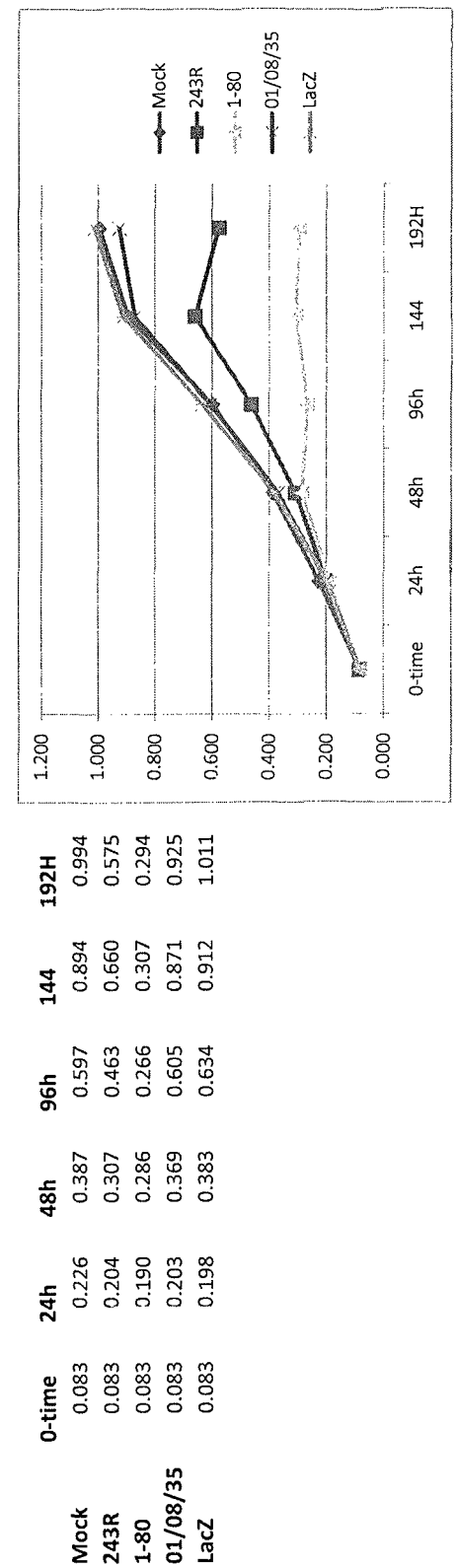
Fig 6I Adenocarcinoma of the breast MB231 - Virus Alone: Average of 2 Experiments
|  | 0-time | 48h | 96h | 144h | 192H |
|---|---|---|---|---|---|
| Mock | 0.063 | 0.437 | 1.221 | 1.355 | 0.877 |
| 243R | 0.063 | 0.436 | 0.900 | 1.009 | 0.753 |
| 1-80 | 0.063 | 0.257 | 0.264 | 0.161 | 0.070 |
| 01/08/35 | 0.063 | 0.432 | 1.036 | 1.306 | 0.765 |
| LacZ | 0.063 | 0.406 | 1.065 | 1.268 | 0.658 |
Fig 6J Adenocarcinoma of the breast SPC3 - Virus Alone: Average of 3 Experiments
|  | 0-time | 24h | 48h | 96h | 144 | 192H |
|---|---|---|---|---|---|---|
| Mock | 0.083 | 0.226 | 0.387 | 0.597 | 0.894 | 0.994 |
| 243R | 0.083 | 0.204 | 0.307 | 0.463 | 0.660 | 0.575 |
| 1-80 | 0.083 | 0.190 | 0.286 | 0.266 | 0.307 | 0.294 |
| 01/08/35 | 0.083 | 0.203 | 0.369 | 0.605 | 0.871 | 0.925 |
| LacZ | 0.083 | 0.198 | 0.383 | 0.634 | 0.912 | 1.011 |

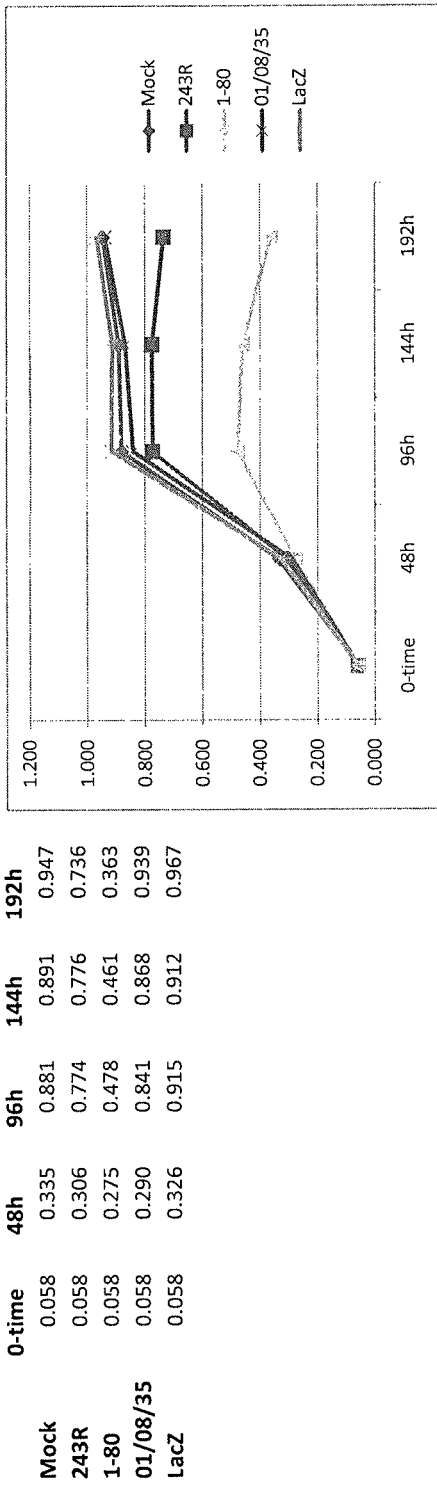
Fig 6K Adenocarcinoma of the breast MCF7 - Virus Alone: Average of 2 Experiments
|          | 0-time | 48h   | 96h   | 144h  | 192h  |
|----------|--------|-------|-------|-------|-------|
| Mock     | 0.058  | 0.335 | 0.881 | 0.891 | 0.947 |
| 243R     | 0.058  | 0.306 | 0.774 | 0.776 | 0.736 |
| 1-80     | 0.058  | 0.275 | 0.478 | 0.461 | 0.363 |
| 01/08/35 | 0.058  | 0.290 | 0.841 | 0.868 | 0.939 |
| LacZ     | 0.058  | 0.326 | 0.915 | 0.912 | 0.967 |
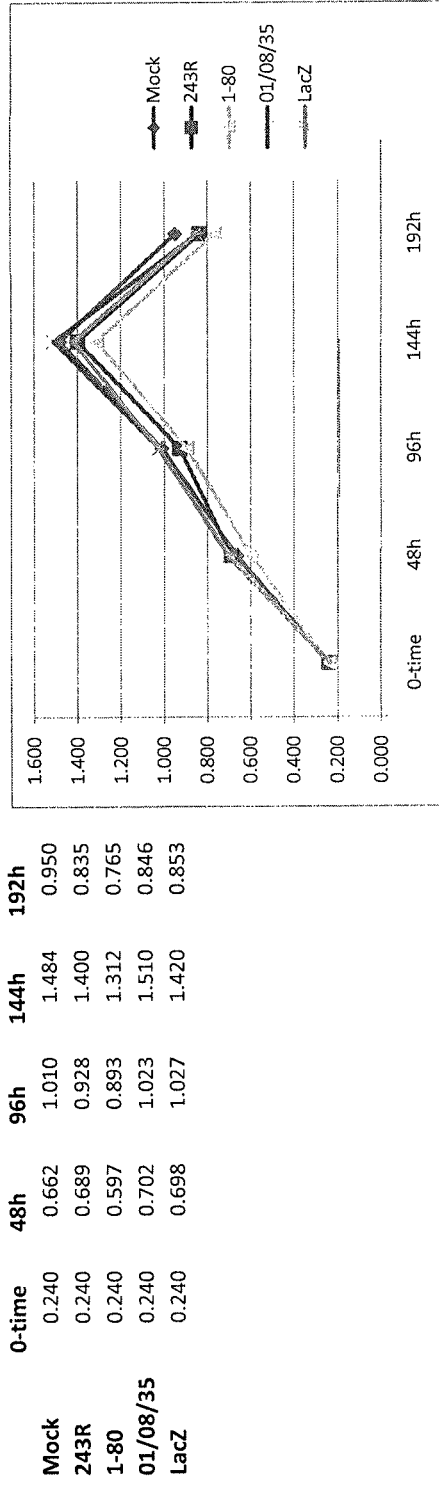
Fig 6L Glioblastoma T98 - Virus Alone: Average of 3 Experiments
|          | 0-time | 48h   | 96h   | 144h  | 192h  |
|----------|--------|-------|-------|-------|-------|
| Mock     | 0.240  | 0.662 | 1.010 | 1.484 | 0.950 |
| 243R     | 0.240  | 0.689 | 0.928 | 1.400 | 0.835 |
| 1-80     | 0.240  | 0.597 | 0.893 | 1.312 | 0.765 |
| 01/08/35 | 0.240  | 0.702 | 1.023 | 1.510 | 0.846 |
| LacZ     | 0.240  | 0.698 | 1.027 | 1.420 | 0.853 |

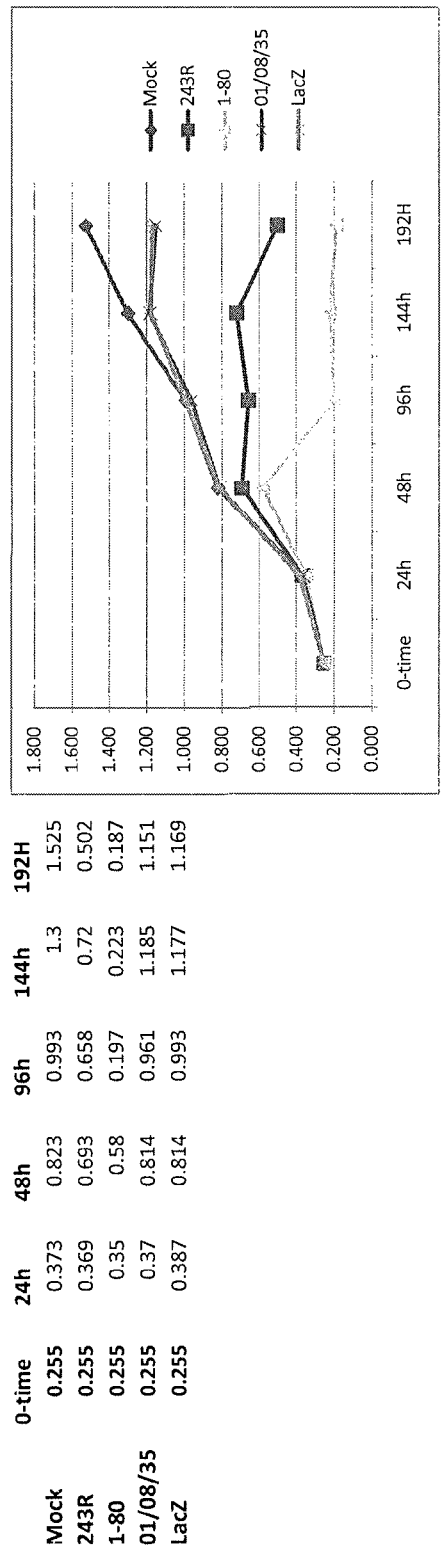
Fig 6M Glioblastoma SNP-19 - Virus Alone: Average of 3 Experiments
|  | 0-time | 24h | 48h | 96h | 144h | 192H |
|---|---|---|---|---|---|---|
| Mock | 0.255 | 0.373 | 0.823 | 0.993 | 1.3 | 1.525 |
| 243R | 0.255 | 0.369 | 0.693 | 0.658 | 0.72 | 0.502 |
| 1-80 | 0.255 | 0.35 | 0.58 | 0.197 | 0.223 | 0.187 |
| 01/08/35 | 0.255 | 0.37 | 0.814 | 0.961 | 1.185 | 1.151 |
| LacZ | 0.255 | 0.387 | 0.814 | 0.993 | 1.177 | 1.169 |
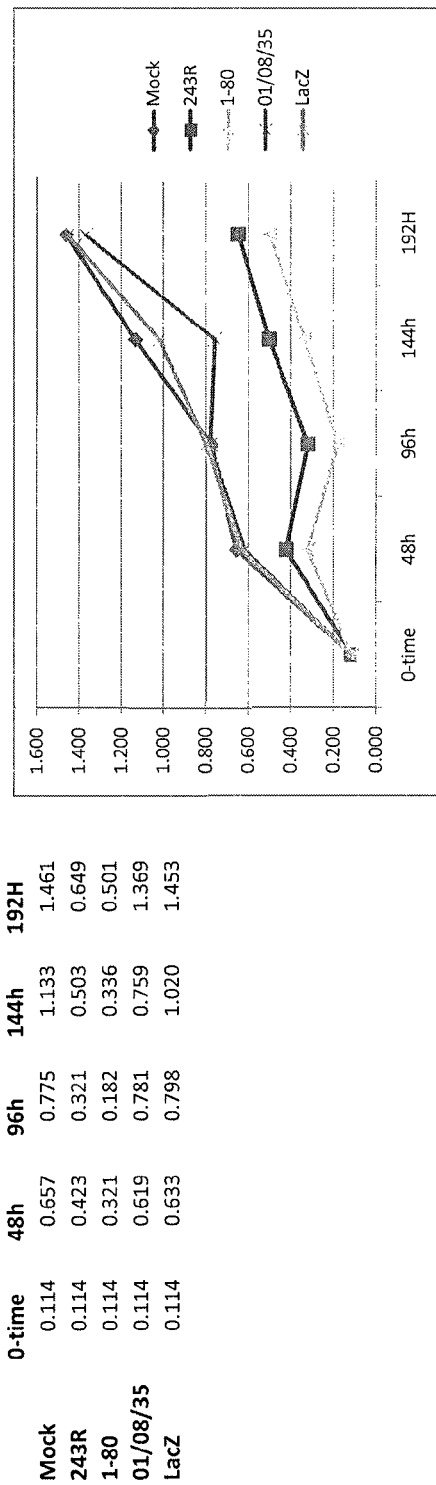
Fig 6N Adenocarcinoma of the prostate PC3 - Virus Alone: Average of 2 Experiments
|  | 0-time | 48h | 96h | 144h | 192H |
|---|---|---|---|---|---|
| Mock | 0.114 | 0.657 | 0.775 | 1.133 | 1.461 |
| 243R | 0.114 | 0.423 | 0.321 | 0.503 | 0.649 |
| 1-80 | 0.114 | 0.321 | 0.182 | 0.336 | 0.501 |
| 01/08/35 | 0.114 | 0.619 | 0.781 | 0.759 | 1.369 |
| LacZ | 0.114 | 0.633 | 0.798 | 1.020 | 1.453 |

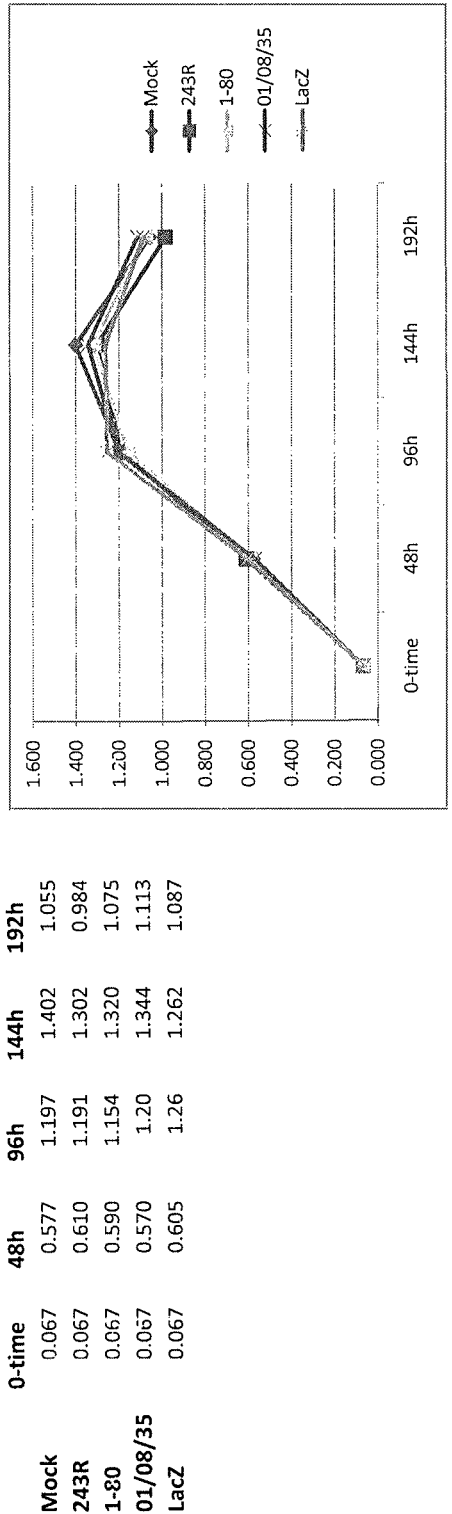
Fig 6O Adenocarcinoma of the ovary ES2 - Virus Alone: Average of 3 Experiments
|  | 0-time | 48h | 96h | 144h | 192h |
|---|---|---|---|---|---|
| Mock | 0.067 | 0.577 | 1.197 | 1.402 | 1.055 |
| 243R | 0.067 | 0.610 | 1.191 | 1.302 | 0.984 |
| 1-80 | 0.067 | 0.590 | 1.154 | 1.320 | 1.075 |
| 01/08/35 | 0.067 | 0.570 | 1.20 | 1.344 | 1.113 |
| LacZ | 0.067 | 0.605 | 1.26 | 1.262 | 1.087 |

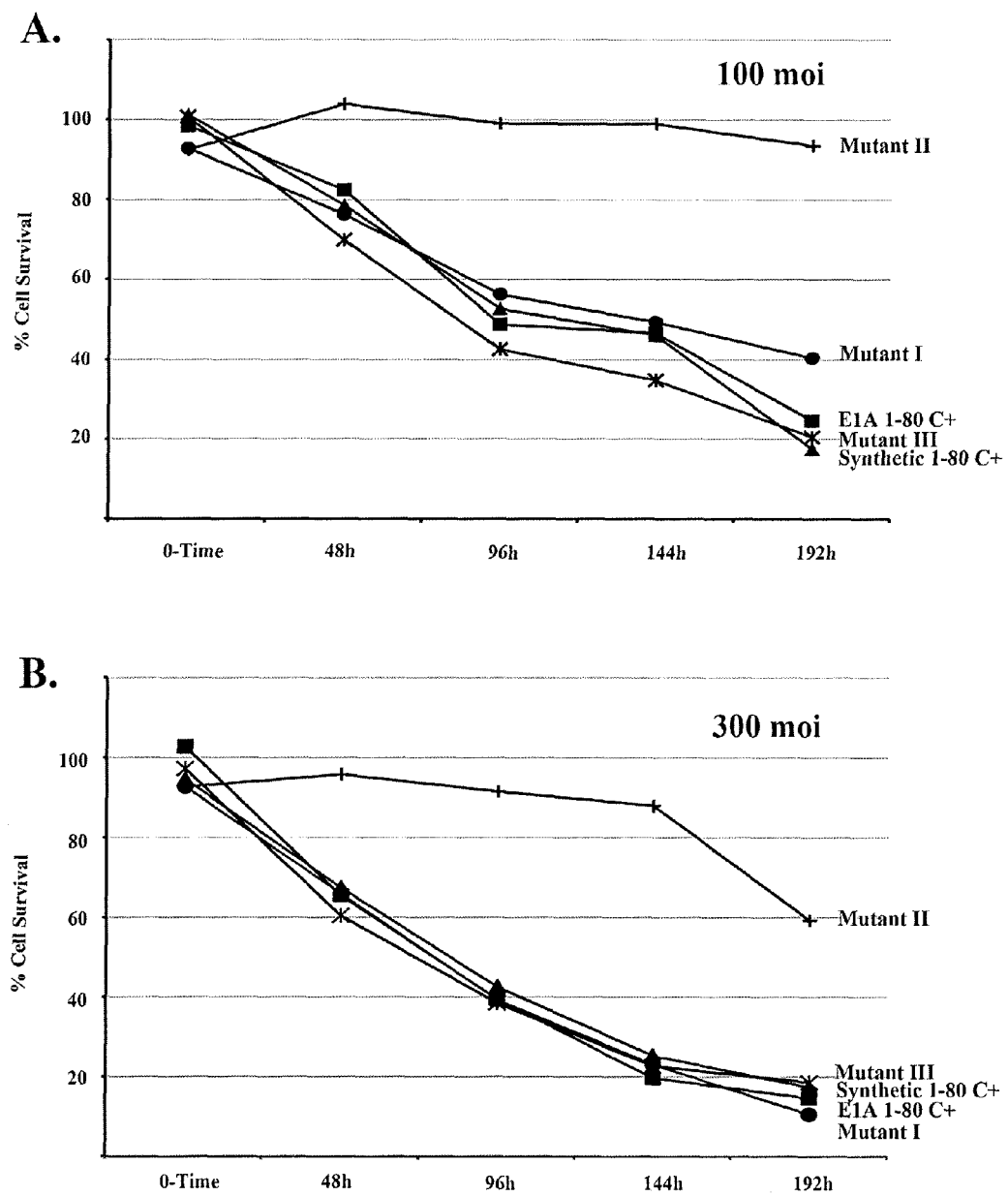
FIG. 7A-B

SEQUENCE LISTING

<160> NUMBER OF SEQ ID NOS: 48

<210> SEQ ID NO 1
<211> LENGTH: 80
<212> TYPE: PRT
<213> ORGANISM: Artificial Sequence
<220> FEATURE:
<223> OTHER INFORMATION: Synthetic peptide

<400> SEQUENCE: 1

Met Arg His Ile Ile Cys His Gly Gly Val Ile Thr Glu Glu Met Ala
1               5                   10                  15

Ala Ser Leu Leu Asp Gln Leu Ile Glu Glu Val Leu Ala Asp Asn Leu
            20                  25                  30

Pro Pro Pro Ser His Phe Glu Pro Pro Thr Leu His Glu Leu Tyr Asp
        35                  40                  45

Leu Asp Val Thr Ala Pro Glu Asp Pro Asn Glu Glu Ala Val Ser Gln
    50                  55                  60

Ile Phe Pro Asp Ser Val Met Leu Ala Val Gln Glu Gly Ile Asp Leu
65                  70                  75                  80

<210> SEQ ID NO 2
<211> LENGTH: 14
<212> TYPE: PRT
<213> ORGANISM: Artificial Sequence
<220> FEATURE:
<223> OTHER INFORMATION: Synthetic peptide

<400> SEQUENCE: 2

Val Asp Leu Glu Gly Pro Arg Phe Glu Gly Lys Pro Ile Pro
1               5                   10

<210> SEQ ID NO 3
<211> LENGTH: 39
<212> TYPE: PRT
<213> ORGANISM: Artificial Sequence
<220> FEATURE:
<223> OTHER INFORMATION: Synthetic peptide

<400> SEQUENCE: 3

Lys Gly Gly Arg Ala Asp Pro Ala Phe Leu Tyr Lys Val Val Asp Leu
1               5                   10                  15

Glu Gly Pro Arg Phe Glu Gly Lys Pro Ile Pro Asn Pro Leu Leu Gly
            20                  25                  30

Leu Asp Ser Thr Arg Thr Gly
        35

```
<210> SEQ ID NO 4
<211> LENGTH: 27
<212> TYPE: PRT
<213> ORGANISM: Artificial Sequence
<220> FEATURE:
<223> OTHER INFORMATION: Synthetic peptide

<400> SEQUENCE: 4

Lys Gly Gly Arg Ala Asp Pro Ala Phe Leu Tyr Lys Val Val Asp Leu
1               5                   10                  15

Glu Gly Pro Arg Phe Glu Gly Lys Pro Ile Pro
            20                  25

<210> SEQ ID NO 5
<211> LENGTH: 23
<212> TYPE: PRT
<213> ORGANISM: Artificial Sequence
<220> FEATURE:
<223> OTHER INFORMATION: Synthetic peptide

<400> SEQUENCE: 5

Gly Ala Leu Phe Leu Gly Trp Leu Gly Ala Ala Gly Ser Thr Met Gly
1               5                   10                  15

Ala Lys Lys Lys Arg Lys Val
            20

<210> SEQ ID NO 6
<211> LENGTH: 16
<212> TYPE: PRT
<213> ORGANISM: Artificial Sequence
<220> FEATURE:
<223> OTHER INFORMATION: Synthetic peptide

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Arg Arg Met Lys Trp Lys Lys
1               5

<210> SEQ ID NO 8
<211> LENGTH: 16
<212> TYPE: PRT
<213> ORGANISM: Artificial Sequence
<220> FEATURE:
<223> OTHER INFORMATION: Synthetic peptide

<400> SEQUENCE: 8

Arg Arg Trp Arg Arg Trp Trp Arg Arg Trp Trp Arg Arg Trp Arg Arg
1               5                   10                  15

<210> SEQ ID NO 9
<211> LENGTH: 18
<212> TYPE: PRT
<213> ORGANISM: Artificial Sequence
<220> FEATURE:
<223> OTHER INFORMATION: Synthetic peptide
```

```
<400> SEQUENCE: 9

Arg Gly Gly Arg Leu Ser Tyr Ser Arg Arg Phe Ser Thr Ser Thr
1               5                   10                  15

Gly Arg

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide

<400> SEQUENCE: 10

Tyr Gly Arg Lys Lys Arg Arg Gln Arg Arg Arg
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide

<400> SEQUENCE: 11

Arg Lys Lys Arg Arg Gln Arg Arg Arg
1               5

<210> SEQ ID NO 12
<211> LENGTH: 11
<212> TYPE: PRT
<213> ORGANISM: Artificial Sequence
<220> FEATURE:
<223> OTHER INFORMATION: Synthetic peptide

<400> SEQUENCE: 12

Tyr Ala Arg Ala Ala Arg Gln Ala Arg Ala
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide

<400> SEQUENCE: 13

Arg Arg Arg Arg Arg Arg Arg Arg
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic peptide

<400> SEQUENCE: 14

Lys Lys Lys Lys Lys Lys Lys Lys
1               5

<210> SEQ ID NO 15
<211> LENGTH: 27
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: misc_feature
<222> LOCATION: (25)..(25)
<223> OTHER INFORMATION: Xaa can be any naturally occurring amino acid

<400> SEQUENCE: 15

Gly Trp Thr Leu Asn Ser Ala Gly Tyr Leu Leu Gly Lys Ile Asn Leu
1               5                   10                  15

Lys Ala Leu Ala Ala Leu Ala Lys Xaa Ile Leu
            20                  25

<210> SEQ ID NO 16
<211> LENGTH: 18
<212> TYPE: PRT
<213> ORGANISM: Artificial Sequence
<220> FEATURE:
<223> OTHER INFORMATION: Synthetic peptide

<400> SEQUENCE: 16

Leu Leu Ile Leu Leu Arg Arg Arg Ile Arg Lys Gln Ala Asn Ala His
1               5                   10                  15

Ser Lys

<210> SEQ ID NO 17
<211> LENGTH: 16
<212> TYPE: PRT
<213> ORGANISM: Artificial Sequence
<220> FEATURE:
<223> OTHER INFORMATION: Synthetic peptide

<400> SEQUENCE: 17

Ser Arg Arg His His Cys Arg Ser Lys Ala Lys Arg Ser Arg His His
1               5                   10                  15

<210> SEQ ID NO 18
<211> LENGTH: 11
<212> TYPE: PRT
<213> ORGANISM: Artificial Sequence
<220> FEATURE:
<223> OTHER INFORMATION: Synthetic peptide

<400> SEQUENCE: 18

Asn Arg Ala Arg Arg Asn Arg Arg Arg Val Arg
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide

<400> SEQUENCE: 19

Arg Gln Leu Arg Ile Ala Gly Arg Arg Leu Arg Gly Arg Ser Arg
1               5                   10                  15

<210> SEQ ID NO 20
<211> LENGTH: 13
<212> TYPE: PRT
<213> ORGANISM: Artificial Sequence
<220> FEATURE:
<223> OTHER INFORMATION: Synthetic peptide

<400> SEQUENCE: 20

Lys Leu Ile Lys Gly Arg Thr Pro Ile Lys Phe Gly Lys
1               5                   10
```

```
<210> SEQ ID NO 21
<211> LENGTH: 10
<212> TYPE: PRT
<213> ORGANISM: Artificial Sequence
<220> FEATURE:
<223> OTHER INFORMATION: Synthetic peptide

<400> SEQUENCE: 21

Arg Arg Ile Pro Asn Arg Arg Pro Arg Arg
1               5                   10

<210> SEQ ID NO 22
<211> LENGTH: 18
<212> TYPE: PRT
<213> ORGANISM: Artificial Sequence
<220> FEATURE:
<223> OTHER INFORMATION: Synthetic peptide

<400> SEQUENCE: 22

Lys Leu Ala Leu Lys Leu Ala Leu Lys Ala Leu Lys Ala Ala Leu Lys
1               5                   10                  15

Leu Ala

<210> SEQ ID NO 23
<211> LENGTH: 14
<212> TYPE: PRT
<213> ORGANISM: Artificial Sequence
<220> FEATURE:
<223> OTHER INFORMATION: Synthetic peptide

<400> SEQUENCE: 23

Lys Leu Ala Lys Leu Ala Lys Lys Leu Ala Lys Leu Ala Lys
1               5                   10

<210> SEQ ID NO 24
<211> LENGTH: 27
<212> TYPE: PRT
<213> ORGANISM: Artificial Sequence
<220> FEATURE:
<223> OTHER INFORMATION: Synthetic peptide

<400> SEQUENCE: 24

Gly Ala Leu Phe Leu Gly Phe Leu Gly Ala Ala Gly Ser Thr Asn Gly
1               5                   10                  15

Ala Trp Ser Gln Pro Lys Lys Lys Arg Lys Val
            20                  25

<210> SEQ ID NO 25
<211> LENGTH: 21
<212> TYPE: PRT
<213> ORGANISM: Artificial Sequence
<220> FEATURE:
<223> OTHER INFORMATION: Synthetic peptide

<400> SEQUENCE: 25

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 26
<211> LENGTH: 20
<212> TYPE: PRT
<213> ORGANISM: Artificial Sequence
<220> FEATURE:
<223> OTHER INFORMATION: Synthetic peptide
```

```
<400> SEQUENCE: 26

Leu Lys Lys Leu Leu Lys Lys Leu Leu Lys Leu Leu Lys Lys Leu
1               5                   10                  15

Leu Lys Lys Leu
            20

<210> SEQ ID NO 27
<211> LENGTH: 34
<212> TYPE: PRT
<213> ORGANISM: Artificial Sequence
<220> FEATURE:
<223> OTHER INFORMATION: Synthetic peptide

<400> SEQUENCE: 27

Gln Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 28
<211> LENGTH: 23
<212> TYPE: PRT
<213> ORGANISM: Artificial Sequence
<220> FEATURE:
<223> OTHER INFORMATION: Synthetic peptide

<400> SEQUENCE: 28

Met Gly Leu Gly Leu His Leu Leu Val Leu Ala Ala Ala Leu Gln Gly
1               5                   10                  15

Ala Lys Ser Lys Arg Lys Val
            20

<210> SEQ ID NO 29
<211> LENGTH: 26
<212> TYPE: PRT
<213> ORGANISM: Artificial Sequence
<220> FEATURE:
<223> OTHER INFORMATION: Synthetic peptide

<400> SEQUENCE: 29

Ala Ala Val Ala Leu Leu Pro Ala Val Leu Leu Ala Leu Leu Ala Pro
1               5                   10                  15

Ala Ala Ala Asn Tyr Lys Lys Pro Lys Leu
            20                  25

<210> SEQ ID NO 30
<211> LENGTH: 28
<212> TYPE: PRT
<213> ORGANISM: Artificial Sequence
<220> FEATURE:
<223> OTHER INFORMATION: Synthetic peptide

<400> SEQUENCE: 30

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 31
<211> LENGTH: 24
<212> TYPE: PRT
<213> ORGANISM: Artificial Sequence
```

<220> FEATURE:
<223> OTHER INFORMATION: Synthetic peptide

<400> SEQUENCE: 31

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 32
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(24)
<223> OTHER INFORMATION: Xaa can be any naturally occurring amino acid

<400> SEQUENCE: 32

Asp Pro Lys Gly Asp Pro Lys Gly Val Thr Val Thr Val Thr Val Thr
1               5                   10                  15

Val Thr Gly Lys Gly Asp Pro Xaa Pro Asp
            20                  25

<210> SEQ ID NO 33
<211> LENGTH: 14
<212> TYPE: PRT
<213> ORGANISM: Artificial Sequence
<220> FEATURE:
<223> OTHER INFORMATION: Synthetic peptide

<400> SEQUENCE: 33

Pro Pro Pro Pro Pro Pro Pro Pro Pro Pro Pro Pro
1               5                   10

<210> SEQ ID NO 34
<211> LENGTH: 18
<212> TYPE: PRT
<213> ORGANISM: Artificial Sequence
<220> FEATURE:
<223> OTHER INFORMATION: Synthetic peptide

<400> SEQUENCE: 34

Val Arg Leu Pro Pro Pro Val Arg Leu Pro Pro Pro Val Arg Leu Pro
1               5                   10                  15

Pro Pro

<210> SEQ ID NO 35
<211> LENGTH: 10
<212> TYPE: PRT
<213> ORGANISM: Artificial Sequence
<220> FEATURE:
<223> OTHER INFORMATION: Synthetic peptide

<400> SEQUENCE: 35

Pro Arg Pro Leu Pro Pro Pro Arg Pro Gly
1               5                   10

<210> SEQ ID NO 36
<211> LENGTH: 30
<212> TYPE: PRT
<213> ORGANISM: Artificial Sequence
<220> FEATURE:
<223> OTHER INFORMATION: Synthetic peptide -continued

```
<400> SEQUENCE: 36

Ser Val Arg Arg Pro Arg Pro Pro Tyr Leu Pro Arg Pro Arg Pro
1               5                   10                  15

Pro Pro Phe Phe Pro Pro Arg Leu Pro Pro Arg Ile Pro Pro
            20                  25                  30

<210> SEQ ID NO 37
<211> LENGTH: 21
<212> TYPE: PRT
<213> ORGANISM: Artificial Sequence
<220> FEATURE:
<223> OTHER INFORMATION: Synthetic peptide

<400> SEQUENCE: 37

Thr Arg Ser Ser Arg Ala Gly Leu Gln Phe Pro Val Gly Arg Val His
1               5                   10                  15

Arg Leu Leu Arg Lys
            20

<210> SEQ ID NO 38
<211> LENGTH: 23
<212> TYPE: PRT
<213> ORGANISM: Artificial Sequence
<220> FEATURE:
<223> OTHER INFORMATION: Synthetic peptide

<400> SEQUENCE: 38

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 39
<211> LENGTH: 37
<212> TYPE: PRT
<213> ORGANISM: Artificial Sequence
<220> FEATURE:
<223> OTHER INFORMATION: Synthetic peptide

<400> SEQUENCE: 39

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35

<210> SEQ ID NO 40
<211> LENGTH: 28
<212> TYPE: PRT
<213> ORGANISM: Artificial Sequence
<220> FEATURE:
<223> OTHER INFORMATION: Synthetic peptide

<400> SEQUENCE: 40

Ala Leu Trp Met Thr Leu Leu Lys Lys Val Leu Lys Ala Ala Ala Lys
1               5                   10                  15

Ala Ala Leu Asn Ala Val Leu Val Gly Ala Asn Ala
            20                  25

<210> SEQ ID NO 41
<211> LENGTH: 26
<212> TYPE: PRT
<213> ORGANISM: Artificial Sequence
```

```
<220> FEATURE:
<223> OTHER INFORMATION: Synthetic peptide

<400> SEQUENCE: 41

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 42
<211> LENGTH: 14
<212> TYPE: PRT
<213> ORGANISM: Artificial Sequence
<220> FEATURE:
<223> OTHER INFORMATION: Synthetic peptide

<400> SEQUENCE: 42

Ile Asn Leu Lys Ala Leu Ala Ala Leu Ala Lys Lys Ile Leu
1               5                   10

<210> SEQ ID NO 43
<211> LENGTH: 33
<212> TYPE: PRT
<213> ORGANISM: Artificial Sequence
<220> FEATURE:
<223> OTHER INFORMATION: Synthetic peptide

<400> SEQUENCE: 43

Gly Phe Phe Ala Leu Ile Pro Lys Ile Ile Ser Ser Pro Leu Pro Lys
1               5                   10                  15

Thr Leu Leu Ser Ala Val Gly Ser Ala Leu Gly Gly Ser Gly Gly Gln
            20                  25                  30

Glu

<210> SEQ ID NO 44
<211> LENGTH: 15
<212> TYPE: PRT
<213> ORGANISM: Artificial Sequence
<220> FEATURE:
<223> OTHER INFORMATION: Synthetic peptide

<400> SEQUENCE: 44

Leu Ala Lys Trp Ala Leu Lys Gln Gly Phe Ala Lys Leu Lys Ser
1               5                   10                  15

<210> SEQ ID NO 45
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(23)
<223> OTHER INFORMATION: Xaa can be any naturally occurring amino acid

<400> SEQUENCE: 45

Ser Met Ala Gln Asp Ile Ile Ser Thr Ile Gly Asp Leu Val Lys Trp
1               5                   10                  15

Ile Ile Gln Thr Val Asn Xaa Phe Thr Lys Lys
            20                  25

<210> SEQ ID NO 46
<211> LENGTH: 41
<212> TYPE: PRT
<213> ORGANISM: Artificial Sequence
```

```
-continued

<220> FEATURE:
<223> OTHER INFORMATION: Synthetic peptide

<400> SEQUENCE: 46

Leu Leu Gly Asp Phe Phe Arg Lys Ser Lys Glu Lys Ile Gly Lys Glu
1               5                   10                  15

Phe Lys Arg Ile Val Gln Arg Ile Lys Gln Arg Ile Lys Asp Phe Leu
                20                  25                  30

Ala Asn Leu Val Pro Arg Thr Glu Ser
            35                  40

<210> SEQ ID NO 47
<211> LENGTH: 18
<212> TYPE: PRT
<213> ORGANISM: Artificial Sequence
<220> FEATURE:
<223> OTHER INFORMATION: Synthetic peptide

<400> SEQUENCE: 47

Pro Ala Trp Arg Lys Ala Phe Arg Trp Ala Trp Arg Met Leu Lys Lys
1               5                   10                  15

Ala Ala

<210> SEQ ID NO 48
<211> LENGTH: 18
<212> TYPE: PRT
<213> ORGANISM: Artificial Sequence
<220> FEATURE:
<223> OTHER INFORMATION: Synthetic peptide

<400> SEQUENCE: 48

Lys Leu Lys Leu Lys Leu Lys Leu Lys Leu Lys Leu Lys Leu Lys Leu
1               5                   10                  15

Lys Leu
```

ADENOVIRUS E1A FRAGMENTS FOR USE IN ANTI-CANCER THERAPIES

This application claims benefit of priority to U.S. Provisional Application Ser. No. 61/509,891, filed Jul. 20, 2011, the entire contents of which are hereby incorporated by reference.

This invention was made with government support under grant nos. 5ROICA29561 and 5KO6AI04739 awarded by the National institutes of Health. The government has certain rights in the invention.

BACKGROUND OF THE INVENTION

I. Field of the Invention

The present invention relates to the fields of oncology and molecular biology. More particular the invention relates to cancer therapies utilizing a fragment of adenovirus E1A that represses transcription of oncogenic genes such as HER2/Neu.

II. Related Art

Up-regulation of the HER2/neu (erbB2) proto-oncogene occurs in several types of human cancer, including breast, ovary, and prostate. HER2 up-regulation in breast cancer is predictive of aggressive disease with a poor prognosis; 25-30% of breast cancers are positive for HER2 up-regulation but account for 60-80% of breast cancer deaths (Moasser, 2007a). Of significance, several studies have shown that elevated HER2 levels decrease the susceptibility of cancer cells to chemotherapeutic drugs (Moasser, 2007b). Further, treatment with siRNAs that inhibit HER2 translation was found to promote growth arrest and apoptosis of breast cancer cell lines (Choudhury et al., 2003). These findings appear to be examples of what has been termed "Oncogene Addiction" (Weinstein, 2002).

Several studies with human cancer cell lines have shown that although they may have acquired multiple genetic and epigenetic abnormalities, they can remain highly dependent on the expression of a single oncogene for cell proliferation and survival (Weinstein and Joe, 2008). Oncogene addiction has been demonstrated in several mouse model systems including MYC-driven papillomas, lymphomas and osteosarcomas (Felsher and Bishop, 1999; Jain et al., 2002; Pelengaris et al., 1999), hRAS-driven melanoma (Chin et al., 1999) and BCR/ABL-driven leukemia (Huettner et al., 2000). Interference with the function of the oncogene which drives a specific tumor is a therapeutic approach that has met with some clinical success including targeting BCR-ABL (imatinib), EGRF (gefitinib, erlotinib) and HER2 (trastuzumab) (Weinstein and Joe, 2008).

The Ad group C (types 2 and 5) E1A oncogene encodes two major proteins of 243 and 289 amino acid residues (243R and 289R) which contain multiple functional domains that interact with key cellular regulatory factors. E1A is involved in diverse functions, including transcriptional activation, induction of cellular DNA synthesis, cell immortalization, cell transformation, and of particular interest, transcriptional-repression. E1A 289R differs from E1A 243R by conserved region 3 (CR3), a 46 amino acid domain unique to 289R that is involved in transcription-activation of Ad early genes (Lillie et al., 1987; Green et al., 1988). The Ad5 oncogene inhibits the expression of HER2 in rodent and human cell cultures (Yan et al., 1991; Yu et al., 1990; Yu et al., 1991). However, the full length Ad E1A oncogene is not a good candidate as a therapy because it possesses, in addition to its transcription-repression function, other biological activities which may complicate a medical therapy and could have long-term deleterious effects. Further, other E1A domains interact with several important cellular proteins not associated with its transcriptional repression function, including, for example, Rb, p21, and CtBP, all of which can have profound effects on cell cycle regulation.

The present inventors have previously demonstrated that the transcription-repression function of the E1A oncogene consists of two critical sub-domains that reside solely within the N-terminal 80 amino acids of E1A (Song et al., 1995a; Song et al., 1995b; Song et al., 1995c; Song et al., 1997; Boyd et al., 2002; Loewenstein et al., 2006). Extensive studies demonstrated that the E1A repression domain (a recombinant protein containing only the N-terminal 80 amino acids), exhibits the same repression function as the entire E1A 243R oncoprotein. Single amino acid substitution analysis of the two E1A N-terminal repression sub-domains has led to a two-step model of E1A repression (Boyd et al., 2002; Loewenstein et al., 2006): first E1A gains access to repressible promoters by interaction of E1A repression sub-domains 1 (amino acids ~1-30) and 2 (amino acids ~48-60) with a promoter-bound cellular partner such as p300; second, the E1A N-terminus (sub-domain 1) interacts with TBP (TATA binding protein) and disrupts the TBP/TATA complex thus blocking transcription (Green et al., 2008a; Green et al., 2008b). However, the ability of this molecule to repress the expression of oncogenes such as HER2/Neu inside cancer cells has yet to be explored.

SUMMARY OF THE INVENTION

Thus, in accordance with the present invention, there is provided a method of inhibiting a cancer cell comprising contacting the cancer cell with a polypeptide characterized as (a) comprising residues 1-80 of adenovirus E1A (SEQ ID NO: 1); (b) substantially lacking E1A sequences C-terminal to residue 80; and (c) comprising a non-E1A stabilization sequence located C-terminal to residue 80. The cancer cell may or may not overexpress HER2-Neu as compared to a non-cancer cell. The cancer cell may be a breast cancer cell, a lung cancer cell, an ovarian cancer cell, a brain cancer cell, or a prostate cancer cell. The cancer cell may be a carcinoma, an adenocarcinoma or a glioblastoma. The cancer cell may be a multi-drug resistant cancer cell. The non-E1A stabilization sequence may be about 40 residues in length, may comprises SEQ ID NO: 3, may comprise or consist of residues 1-27 or 14-27 of SEQ ID NO: 3, or may consists of SEQ ID NO: 2. The polypeptide may lack E1A sequences other than SEQ ID NO: 1.

Contacting may comprise introducing into the cell a viral vector comprising an polynucleotide segment encoding the polypeptide under the control of a promoter active in the cell. The viral vector may be an adenoviral vector, poxvirus vector, herpesvirus vector, adeno-associated viral vector, or lentiviral vector. The promoter may be a viral promoter or a tissue specific promoter. The viral promoter may be a cytomegalovirus immediate early promoter. Alternatively, contacting may comprise introducing into the cell a non-viral vector comprising an polynucleotide segment encoding the polypeptide under the control of a promoter active in the cell. The non-viral vector may be delivered in a lipid delivery vehicle. The polypeptide may further comprise a cell penetrating domain. The cancer cell may be located in a non-human animal, or in a human subject.

The method may further comprise contacting the cancer cell with a second anti-cancer treatment. The second anti-cancer treatment may be given prior to the polypeptide, after the polypeptide, or at the same time as the polypeptide. The second anti-cancer treatment may be selected from the group consisting of radiotherapy, chemotherapy, immunotherapy, gene therapy, toxin therapy, hormone therapy or cryotherapy. The method may also further comprise contacting the polypeptide with the cancer cell at least a second time. Inhibiting may comprise slowing the growth of the cancer cell, or killing the cancer cell, such as by inducing apoptosis in the cancer cell. The method may further comprise assessing HER2-Neu expression prior to contacting, such as by an ELISA.

In another embodiment, there is provided a method of treating a subject with cancer comprising contacting a cancer cell in the subject with a polypeptide characterized as (a) comprising residues 1-80 of adenovirus E1A (SEQ ID NO: 1); (b) substantially lacking E1A sequences C-terminal to residue 80; and (c) comprising a non-E1A stabilization sequence located C-terminal to residue 80. The cancer cell may or may not overexpress HER2-Neu as compared to a non-cancer cell. The cancer cell may be a breast cancer cell, a lung cancer cell, an ovarian cancer cell, a brain cancer cell, or a prostate cancer cell. The cancer cell may be a carcinoma, an adenocarcinoma or a glioblastoma. The cancer cell may be a multi-drug resistant cancer cell, a recurrent cancer cell or a metastatic cancer cell. The non-E1A stabilization sequence may be about 40 residues in length, may comprise or consist of residues 1-27 or 14-27 of SEQ ID NO: 3, may comprise SEQ ID NO: 3, or may consist of SEQ ID NO: 3. The polypeptide may lack E1A sequences other than SEQ ID NO: 1.

Contacting may comprise administering to the subject a viral vector comprising an polynucleotide segment encoding the polypeptide under the control of a promoter active in the cell. The viral vector may be an adenoviral vector, poxvirus vector, herpesvirus vector, adeno-associated viral vector, or lentiviral vector. The promoter may be a viral promoter or a tissue specific promoter. The viral promoter may be a cytomegalovirus immediate early promoter. Alternatively, contacting may comprise administering to the subject a non-viral vector comprising an polynucleotide segment encoding the polypeptide under the control of a promoter active in the cell. The non-viral vector may be administered in a lipid delivery vehicle. The polypeptide may further comprise a cell penetrating domain.

The method may further comprise contacting the cancer cell with a second anti-cancer treatment. The second anti-cancer treatment may be given prior to the polypeptide, after the polypeptide, or at the same time as the polypeptide. The second anti-cancer treatment may be selected from the group consisting of radiotherapy, chemotherapy, immunotherapy, gene therapy, toxin therapy, hormone therapy, cryotherapy or surgery. The method may also further comprise contacting the polypeptide with the cancer cell at least a second time. Treating comprises slowing the growth of the cancer cell, or killing the cancer cell, such as by inducing apoptosis in the cancer cell. The method may further comprise assessing HER2-Neu expression in the cancer cell prior to contacting, such as by an ELISA.

In yet another embodiment, there is provided a method of improving the quality of life of a subject with cancer comprising contacting a cancer cell in the subject with a polypeptide characterized as (a) comprising residues 1-80 of adenovirus E1A (SEQ ID NO: 1); (b) substantially lacking E1A sequences C-terminal to residue 80; and (c) comprising a non-E1A stabilization sequence located C-terminal to residue 80.

In still yet another embodiment, there is provided a method of improving the survival of a subject with cancer comprising contacting a cancer cell in the subject with an polypeptide characterized as (a) comprising residues 1-80 of adenovirus E1A (SEQ ID NO: 1); (b) substantially lacking E1A sequences C-terminal to residue 80; and (c) comprising a non-E1A stabilization sequence located C-terminal to residue 80.

In yet an additional embodiment, there is provided a method of rendering an unresectable tumor in a subject with cancer resectable comprising contacting the tumor with an polypeptide characterized as (a) comprising residues 1-80 of adenovirus E1A (SEQ ID NO: 1); (b) substantially lacking E1A sequences C-terminal to residue 80; and (c) comprising a non-E1A stabilization sequence located C-terminal to residue 80.

A further embodiment includes a method of delaying metastasis in a subject with cancer comprising contacting a cancer cell in the subject with an polypeptide characterized as (a) comprising residues 1-80 of adenovirus E1A (SEQ ID NO: 1); (b) substantially lacking E1A sequences C-terminal to residue 80; and (c) comprising a non-E1A stabilization sequence located C-terminal to residue 80.

Yet another embodiment involves a method of increasing remission time in a subject with cancer that is in remission comprising contacting a cancer cell in the subject with an polypeptide characterized as (a) comprising residues 1-80 of adenovirus E1A (SEQ ID NO: 1); (b) substantially lacking E1A sequences C-terminal to residue 80; and (c) comprising a non-E1A stabilization sequence located C-terminal to residue 80.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

FIGS. 1A-B. Schematic of E1A organization and functions; E1A 1-80 critical sub-domains 1 and 2. (FIG. 1A) E1A proteins encode multiple domains with diverse biochemical and biological functions. Conserved region 3 (CR 3), found only in the 289R protein, encodes a powerful transactivator whose function is needed for adenovirus replication. The Ad E1A 243R oncoprotein encodes three conserved domains and a non-conserved N-terminus in exon 1 which are essential for cell immortalization and cell transformation. The ability to immortalize cells maps to sequences within the non-conserved N-terminus, CR1, CR2, and CR4. Additional growth regulatory functions map to the N-terminus, CR1, and CR2. These include oncogene co-operation and induction of cell DNA synthesis. The transcription-repression function maps to the N-terminus and CR1 (E1A 1-80). (FIG. 1B) By extensive single amino acid substitution analysis, the inventors have mapped the E1A repression function and its interaction with cellular partners to two sub-domains. Within the first sub-domain amino acids 3His, 4Ile, 5Ile 6Cys and 20Leu are critical for interactions with p300 and with TBP. Within the second sub-domain 53Ala, 54Pro, 55Glu and 56Asp are especially important for interaction with p300 (SEQ ID NO:1).

FIGS. 2A-B. Transcription from an exogenous HER2 promoter is repressed by E1A 243R and E1A 1-80. (FIG. 2A) Normal human breast cells, MCF-10A, were transfected with a plasmid expressing the luciferase gene driven by the HER2 promoter and co-transfected with pDest47 expressing E1A 243R. Cells were harvested 48 h post transfection, and luciferase gene expression measured. Data are from a representative experiment. (FIG. 2B) Human breast cancer cells, SK-BR-3, were transfected with pcDNA3 or with pcDNA3 expressing E1A 243R or E1A 1-80. Cells were harvested 48 h post transfection, and luciferase gene expression measured. Data are from a representative experiment.

FIGS. 4A-B. E1A 1-80 modified at its C-terminus is expressed from an Ad vector at high levels. (FIG. 4A) A549 cells were infected at 30 or 300 moi and subjected to Western blot analysis. E1A 1-80 C+ is expressed at much higher levels than E1A 1-80. (FIG. 4B) Pulse-chase analysis demonstrates that the turnover rate for E1A 1-80 and E1A 1-80 C+ are approximately the same. The relative amounts of expression are indicated below each lane. Data are from a representative experiment.

(FIG. 5A) SK-BR-3 human breast cancer cells or (FIG. 5B) HS 579.Mg normal human breast cells were mock infected (•--•) or were infected with the indicated moi of AdCMV E1A 243R (■--■), AdCMV E1A 1-80 C+ (★--★), AdCMV E1A 243R dl1101/1108/1135 (▲--▲) or AdCMV LacZ (♦--♦). Cell viability was measured. Results are the average of three or more experiments.

FIGS. 6A-O. The activity of Ad-expressed full-length E1A 243R and E1A 1-80 C+ against various normal and cancer cells compared to controls. Various human cancer cells but not normal cells are killed by the expression of the E1A transcription-repression domain. FIG. 6A; HS68 cells. FIG. 6B; MG.579 cells. FIG. 6C; MCF 12A cells. FIG. 6D; MCF 10A cells. FIG. 6E; SW620 cells. FIG. 6F; A549 cells. FIG. 6G; NCI460 cells. FIG. 6H; SKBR3 cells. FIG. 6I; MB231 cells. FIG. 6J; SPC3 cells. FIG. 6K; MCF7 cells. FIG. 6L; T98 cells. FIG. 6M; SNP-19 cells. FIG. 6N; PC3 cells. FIG. 6O; ES2 cells.

FIG. 7. SK BR3 cells were subjected to infection with 100 moi or 300 moi of Ad vector expressing E1A 1-80 C+ (■), synthetic GeneArt® E1A 1-80 C+ (▲), synthetic GeneArt® mutant I (●), synthetic GeneArt® mutant II (+) or synthetic GeneArt® mutant III (☆). Cell survival was accessed at the indicated times post infection by cell proliferation assay kit. Data are the average of two experiments.

DETAILED DESCRIPTION OF THE PREFERRED EMBODIMENTS

Figure 3:
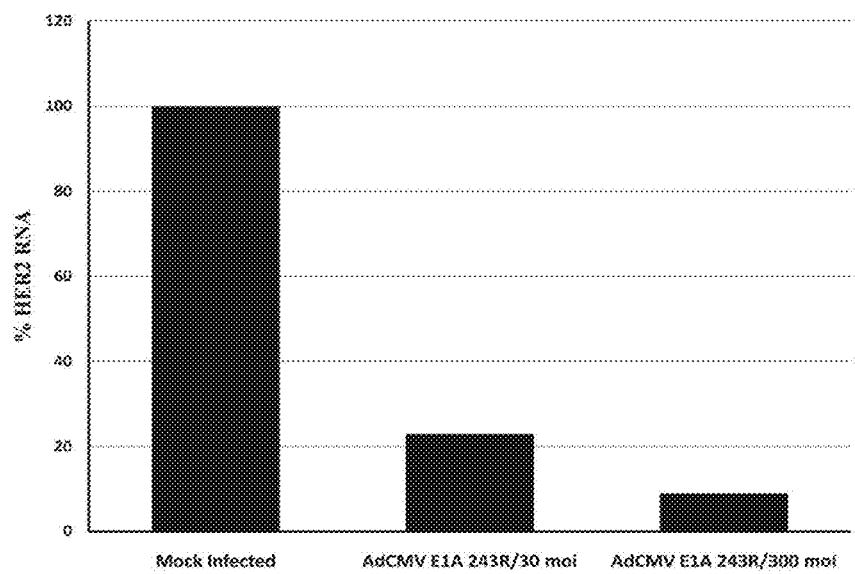
FIG. 3. E1A 243R, when expressed from an Ad vector, is able to repress the transcription of the endogenous HER2 promoter in SK-BR-3 human breast cancer cells. Cells were infected with 30 or 300 moi of AdCMV E1A 243R and harvested 36 h PI. Expression of HER2 was measured by quantitative RT PCR. Data are from a representative experiment.

The inventors describe herein the transcription-repression of the HER2/Neu proto-oncogene in a novel approach to the treatment of HER2 up-regulated cancers. They propose the use of a single functional domain of the multifunctional human adenovirus (Ad) early region 1A (E1A) oncogene to transcriptionally repress HER2 expression and thus negate its function in HER2-mediated breast cancer pathogenesis. The successful identification and development of a strong E1A transcription-repressor of HER2 may lead to valuable adjunct therapies with Herceptin® (trastuzumab) (Beuzeboc et al., 1999) or with other traditional chemotherapeutic regimes. Transcription-repression of HER2 by E1A may prove to be a superior method of blocking HER2 function. Herceptin interferes with the function of the HER2 tyrosine kinase cell-surface receptor in HER2 up-regulated cancers; however, even a small percentage of unblocked receptors can allow the HER2 signal cascade to promulgate cancer cell growth. E1A, on the other hand, acts at an earlier stage than Herceptin® to efficiently repress HER2 transcription and thus greatly reduce its intracellular levels. Therefore, therapy with E1A, optionally in a co-therapy with Herceptin, could substantially increase the effective treatment of HER2 oncogene addicted cancer cells. These and other aspects of the invention are described in detail below.

I. HER2/NEU

HER2/neu (also known as ErbB-2) stands for "Human Epidermal growth factor Receptor 2" and is a protein giving higher aggressiveness in breast cancers. It is a member of the ErbB protein family, more commonly known as the epidermal growth factor receptor family. HER2/neu has also been designated as CD340 (cluster of differentiation 340) and p185. It is encoded by the ERBB2 gene.

HER2 is a cell membrane surface-bound receptor tyrosine kinase and is normally involved in the signal transduction pathways leading to cell growth and differentiation. It is encoded within the genome by HER2/neu, a known proto-oncogene. HER2 is thought to be an orphan receptor, with none of the EGF family of ligands able to activate it. However, ErbB receptors dimerise on ligand binding, and HER2 is the preferential dimerisation partner of other members of the ErbB family. The HER2/neu gene is a proto-oncogene located at the long arm of human chromosome 17 (17q21-q22).

Approximately 30% of breast cancers have an amplification of the HER2/neu gene or overexpression of its protein product. Overexpression of this receptor in breast cancer is associated with increased disease recurrence and worse prognosis. Because of its prognostic role as well as its ability to predict response to trastuzumab (Herceptin US brand name) (see below), breast tumors are routinely checked for overexpression of HER2/neu. Overexpression also occurs in other cancers such as ovarian cancer, stomach cancer, and biologically aggressive forms of uterine cancer, such as uterine serous endometrial carcinoma.

The oncogene HER2/neu is so-named because it was derived from a rodent glioblastoma cell line, which is a type of neural tumor, hence "neu." HER2 is named because it has a similar structure to human epidermal growth factor receptor, or HER1. ErbB2 was named for its similarity to ErbB (avian erythroblastosis oncogene B), the oncogene later found to code for EGFR. Gene cloning showed that neu, HER2, and ErbB2 are the same.

HER2 is co-localized, and, thus, most of the time, co-amplified with the gene GRB7, which is also a proto-oncogene (active in, e.g., breast cancer, testicular germ cell tumor, gastric cancer, and esophageal cancer). It is revealed that patients with ER+/HER2+ compared with ER−/HER2+ breast cancers may actually benefit more from drugs that inhibit the PI3K/AKT molecular pathway. HER2 is known to form clusters which might play a role in tumorigenesis.

II. ADENOVIRUS AND E1A

Adenoviruses are non-enveloped, regular icosohedral, double-stranded DNA viruses. The protein coat (capsid) is composed of 252 capsomeres of which 240 are hexons and 12 are pentons. Most of the detailed structural studies of the adenovirus polypeptides have been done for adenovirus types 2 and 5. The viral DNA is $23.85 \times 10^6$ daltons for adenovirus 2 and varies slightly in size depending on serotype. The DNA has inverted terminal repeats and the length of these varies with the serotype. Virtually every adult has been infected with adenovirus at some time, the major effect being cold-like symptoms. Adenovirus is referred to as a "DNA tumor virus" because of its oncogenic effect in rodents.

The replicative cycle is divided into early (E) and late (L) phases. The late phase defines the onset of viral DNA replication. Adenovirus structural proteins are generally synthesized during the late phase. Following adenovirus infection, host DNA and protein synthesis is inhibited in cells infected with most serotypes. The adenovirus lytic cycle with adenovirus 2 and adenovirus 5 is very efficient and results in approximately 10,000 virions per infected cell along with the synthesis of excess viral protein and DNA that is not incorporated into the virion. Early adenovirus transcription is a complicated sequence of interrelated biochemical events, but it entails essentially the synthesis of viral RNAs prior to the onset of viral DNA replication.

The organization of the adenovirus genome is similar in all of the adenovirus groups and specific functions are generally positioned at identical locations for each serotype studied. Early cytoplasmic messenger RNAs are complementary to four defined, noncontiguous regions on the viral DNA. These regions are designated (E1-E4). The early transcripts have been classified into an array of immediate early (E1a), delayed early (E1b, E2a, E2b, E3 and E4), and intermediate (IVa2.1X) regions.

The E1a region is involved in transcriptional transactivation of viral and cellular genes as well as transcriptional repression of other sequences. The E1a gene exerts an important control function on all of the other early adenovirus messenger RNAs. In normal tissues, in order to transcribe regions E1b, E2a, E2b, E3, or E4 efficiently, active E1a product is required. However, the E1a function may be bypassed. Cells may be manipulated to provide E1a-like functions or may naturally contain such functions. The virus may also be manipulated to bypass the functions.

The E1b region is required for the normal progression of viral events late in infection. The E1b product acts in the host nucleus. Mutants generated within the E1b sequences exhibit diminished late viral mRNA accumulation as well as impairment in the inhibition of host cellular transport normally observed late in adenovirus infection (Berkner, 1988). E1b is required for altering functions of the host cell such that processing and transport are shifted in favor of viral late gene products. These products then result in viral packaging and release of virions. E1b produces a 19 kD protein that prevents apoptosis. E1b also produces a 55 kD protein that binds to p53.

The proteins encoded by the E1A gene of adenovirus have been studied primarily from two points of view. First, the 243 amino acid and 289 amino acid forms of E1A (arising from alternative splicing of the precursor RNA such that the 243 amino acid protein is a subset of the 289 amino acid protein) are both transcriptional regulatory proteins (Flint et al., 1989). Secondly these proteins facilitate the oncogenic transformation of certain rodent cells by other oncogenes, (Ruley, 1983), and, as such E1A is generally classified as an oncogene.

However, there is evidence that the expression of some oncogenes can increase the susceptibility of cells to apoptosis, also known as programmed cell death (Lowe et al., 1993). For example, the E1A gene may increase cellular susceptibility to apoptosis in primary rodent cells (Roa et al., 1992). Other oncogenes, such as c-myc, can also increase cellular susceptibility to programmed cell death (Evan et al., 1992), and overexpression of c-myc may also confer susceptibility to apoptosis induced by anticancer agents, such as tumor necrosis factor-α (Chen et al., 1987), or etoposide (Fanidi et al., 1992; Lowe et al., supra).

Interestingly, and in contrast to E1A's purported oncogenic and apoptotic effects in rodent cells, E1A acts as a tumor suppressor gene in the human context. Frisch (1991), provides evidence of the antioncogenic effect of adenovirus E1A in human tumor cells. More importantly, it was striking and unexpected that E1A sensitizes human tumor cells and enhances tumor cell's response to chemotherapy and irradiation treatment.

A. Structural Features of E1A 1-80

Group C Ad E1A encodes two major regulatory proteins of 243 and 289 amino-acid residues (E1A 243R and E1A 289R) (FIG. 1A). E1A proteins encode multiple domains with diverse biochemical and biological functions including transcriptional activation, transcriptional repression, induction of cellular DNA synthesis, cell immortalization, cell transformation, as well as the inhibition of metastasis and cell differentiation. There are at least four regions (CR1 to CR4) of E1A that are well conserved amongst Ad serotypes. The protein domains of E1A have evolved to interact with key cellular transcription regulators and promoters to control cell cycle progression, cell differentiation and chromatin remodeling.

E1A 289R differs from E1A 243R by conserved region 3 (CR3) (amino-acid residues 140-185), a 46 amino-acid domain unique to 289R. CR3 is essential and sufficient for transcriptional activation of early Ad genes (Lillie et al., 1987; Green et al., 1988). The Ad E1A 243R oncoprotein encodes two conserved domains and a non-conserved N-terminus in exon 1, which are essential for cell immortalization, cell transformation and can induce S-phase DNA synthesis and cell cycle progression by two pathways. The first, the Rb-E2F pathway, involves E1A sequences within CR1 (residues 41-80) and CR2 (residues 121-139), which possess contact sites for Rb family proteins. The second, the N-terminal pathway, is a major focus of the inventors and has been mapped within the E1A N-terminal 80 amino acids (E1A 1-80). E1A 1-80 consists of CR1 and poorly conserved residues 1-40 and takes on added importance because the growth regulatory functions of E1A require sequences within this region. An important biochemical function encoded in the E1A 1-80 is the ability to transcriptionally repress cellular genes involved in cellular proliferation and cell differentiation.

A detailed mutational/functional analysis of E1A 1-80 has identified two regions or sub-domains that are critical for E1A repression: amino acids approximately 1-30 and approximately 48-60 (FIG. 1B). Key amino acids in the first sub-domain include (i) residues 2-6 with 6Cys being especially important, and (ii) residue 20Leu. All of these residues are essential for the transcription-repression function and for disruption of a TBP-TATA complex, but only amino-acid residue 6 appears to be critical for binding p300 under in vitro conditions (Boyd et al., 2002). In contrast, amino acids 53Ala, 54Pro, 55Glu and 56Asp within the second sub-domain are important for the E1A repression function and for binding of E1A's cellular partner p300, but not for binding TBP or for disruption of a TBP-TATA complex (Loewenstein et al., 2007).

These combined findings suggest a two-step hypothetical model as a molecular mechanism for E1A repression (Loewenstein et al., 2007). First E1A uses p300 as a "molecular scaffold" to access specific E1A repressible promoters. E1A likely binds p300 through 6Cys (and possibly adjacent amino acids) within the first sub-domain and with 53Ala, 54Pro, 55Glu and 56Asp (and possibly adjacent amino acids) within the second sub-domain. During the second step, after gaining access to the promoter through interaction with a "molecular scaffold", the N-terminal sub-domain of E1A is able to interact with TBP. This interaction may alter the conformation of TBP, thus melting it from the TATA box.

The amino acid sequence of E1A 1-80 (SEQ ID NO: 1) is provided in FIG. 1B and is listed here in single letter code: MRHIICHGGV ITEEMAASLL DQLIEEVLAD NLPPP-SHFEP PTLHELYDLD VTAPEDPNEE AVSQIFPDSV MLAVQEGIDL.

B. Peptides

The present invention contemplates the use of peptides and fragments of E1A that comprise, consist essentially of or consist of residues 1-80 (SEQ ID NO: 1) of full length E1A. In this context, "consisting essentially of" means that the specified molecule would not contain any additional sequences that would alter the transcription repressing function of E1A 1-80. The term E1A 1-80 is in particular defined as a polypeptide that contains only residues 1-80 of E1A, but the invention may be more generally defined as E1A molecules containing residues 1-80 as well as other non-E1A (or non-adenoviral) sequences. As such, it contains at least 80 residues, but will never contain full length E1A. A particular length may therefore be 80 residues, and 119 residues in the case of E1A 1-80 C+ (see discussion below). Other lengths are contemplated. The term "substantially lacking further E1A sequences" is to be interpreted as a segment containing additional E1A sequences but lacking any additional E1A structures that function as they would in the intact E1A polypeptide. The peptides may be generated synthetically or by recombinant techniques, and may be purified according to known methods, discussed further below.

The peptides may be labeled using various molecules, such as fluorescent, chromogenic or colorimetric agents. The peptides may also be linked to other molecules, including other anti-inflammatory agents. The links may be direct or through distinct linker molecules. The linker molecules in turn may be subject, in vivo, to cleavage, thereby releasing the agent from the peptide. Peptides may also be rendered multimeric by linking to larger, and possibly inert, carrier molecules.

C. Cell Penetrating Domains

The present invention contemplates the use of a cell delivery domain (also called a cell penetrating domain or a cell transduction domain) linked to polypeptides of the present invention. Such domains have been described in the art and are generally characterized as short amphipathic or cationic peptides and peptide derivatives, often containing multiple lysine and arginine resides (Fischer, 2007). Other examples are shown in Table 1, below.

TABLE

| CPD/CTD PEPTIDES RENUMBER SEQS | SEQ ID NO: |
|---|---|
| GALFLGWLGAAGSTMGAKKKRKV | 5 |
| RQIKIWFQNRRMKWKK | 6 |
| RRMKWKK | 7 |
| RRWRRWWRRWWRRWRR | 8 |
| RGGRLSYSRRRFSTSTGR | 9 |
| YGRKKRRQRRR | 10 |
| RKKRRQRRR | 11 |
| YARAAARQARA | 12 |
| RRRRRRRR | 13 |
| KKKKKKKK | 14 |
| GWTLNSAGYLLGKINLKALAALAKXIL | 15 |
| LLILLRRRIRKQANAHSK | 16 |
| SRRHHCRSKAKRSRHH | 17 |
| NRARRNRRRVR | 18 |
| RQLRIAGRRLRGRSR | 19 |
| KLIKGRTPIKFGK | 20 |
| RRIPNRRPRR | 21 |
| KLALKLALKALKAALKLA | 22 |
| KLAKLAKKLAKLAK | 23 |
| GALFLGFLGAAGSTNGAWSQPKKKRKV | 24 |
| KETWWETWWTEWSQPKKKRKV | 25 |
| LKKLLKKLLKKLLKKLLKKL | 26 |
| QAATATRGRSAASRPTERPRAPARSASRPRRPVE | 27 |
| MGLGLHLLVLAAALQGAKSKRKV | 28 |
| AAVALLPAVLLALLAPAAANYKKPKL | 29 |
| MANLGYWLLALFVTMWTDVGLCKKRPKP | 30 |
| LGTYTQDFNKFHTFPQTAIGVGAP | 31 |
| DPKGDPKGVTVTVTVTGKGDPXPD | 32 |
| PPPPPPPPPPPPPPP | 33 |

TABLE-continued

CPD/CTD PEPTIDES RENUMBER SEQS

| | SEQ ID NO: |
|---|---|
| VRLPPPVRLPPPVRLPPP | 34 |
| PRPLPPPRPG | 35 |
| SVRRRPRPPYLPRPRPPPFFPPRLPPRIPP | 36 |
| TRSSRAGLQFPVGRVHRLLRK | 37 |
| GIGKFLHSAKKFGKAFVGEIMNS | 38 |
| KWKLFKKIEKVGQNIRDGIIKAGPAVAVVG QATQIAK | 39 |
| ALWMTLLKKVLKAAAKAALNAVLVGANA | 40 |
| GIGAVLKVLTTGLPALISWIKRKRQQ | 41 |
| INLKALAALAKKIL | 42 |
| GFFALIPKIISSPLPKTLLSAVGSALGGSGGQE | 43 |
| LAKWALKQGFAKLKS | 44 |
| SMAQDIISTIGDLVKWIIQTVNXFTKK | 45 |
| LLGDFFRKSKEKIGKEFKRIVQRIKQRIKDFL ANLVPRTES | 46 |
| PAWRKAFRWAWRMLKKAA | 47 |
| KLKLKLKLKLKLKLKL | 48 |

A particular example of a CPP is HIV TAT. Segments defined by residues 48-60, 47-57 (SEQ ID NO: 10) and 47-55 of TAT all have been demonstrated to function in in transferring cargo molecules into cells. Other sequences such PTD3, Polyarginine, CADY, PepFect6 and RXR can be used as well.

D. Analogs and Mimetics

It also is contemplated in the present invention that variants or analogs of E1A 1-80 peptides may function in the same way as E1A 1-80. Sequence variants of E1A 1-80 peptides, primarily making conservative amino acid substitutions, may even provide improved compositions. Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a peptide to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a peptide that defines that peptide's biological functional activity, certain amino acid substitutions can be made in a protein sequence, and its underlying DNA coding sequence, and nevertheless obtain a peptide with like properties. It is thus contemplated by the inventors that various changes may be made in the DNA sequences coding the peptide without appreciable loss of their biological utility or activity, as discussed below.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant peptide, which in turn defines the interaction of the peptide with other molecules.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a peptide with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide containing molecules that mimic elements of protein secondary structure (Johnson et al, 1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule.

The present invention also may employ peptides that comprise modified, non-natural and/or unusual amino acids. Table 2 provides exemplary, but not limiting, modified, non-natural and/or unusual amino acids are provided herein below. Chemical synthesis may be employed to incorporate such amino acids into the peptides of interest.

TABLE 2

Modified, Non-Natural and Unusual Amino Acids

| Abbr. | Amino Acid | Abbr. | Amino Acid |
|---|---|---|---|
| Aad | 2-Aminoadipic acid | EtAsn | N-Ethylasparagine |
| BAad | 3-Aminoadipic acid | Hyl | Hydroxylysine |
| BAla | beta-alanine, beta-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | Aile | allo-Isoleucine |
| Aib | 2-Aminoisobutyric acid | MeGly | N-Methylglycine, sarcosine |
| BAib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

In addition to the variants discussed above, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

Beta II turns have been mimicked successfully using cyclic L-pentapeptides and those with D-amino acids (Weisshoff et al., 1999). Also, Johannesson et al. (1999) report on bicyclic tripeptides with reverse turn inducing properties.

Methods for generating specific structures have been disclosed in the art. For example, alpha-helix mimetics are disclosed in U.S. Pat. Nos. 5,446,128; 5,710,245; 5,840,833; and 5,859,184. Theses structures render the peptide or protein more thermally stable, also increase resistance to proteolytic degradation. Six, seven, eleven, twelve, thirteen and fourteen membered ring structures are disclosed.

Methods for generating conformationally-restricted β turns and β bulges are described, for example, in U.S. Pat. Nos. 5,440,013; 5,618,914; and 5,670,155. β-turns permit changed side substituents without having changes in corresponding backbone conformation, and have appropriate termini for incorporation into peptides by standard synthesis procedures. Other types of mimetic turns include reverse and γ turns. Reverse turn mimetics are disclosed in U.S. Pat. Nos. 5,475,085 and 5,929,237, and γ turn mimetics are described in U.S. Pat. Nos. 5,672,681 and 5,674,976.

E. Fusions

Another variant is a fusion. This molecule generally has all or a substantial portion of the original molecule, in this case a peptide comprising the E1A 1-80 sequence, linked at the N- or C-terminus to all or a portion of a second peptide or polypeptide. For example, fusions may employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

In particular, the present invention contemplates a fusion at the C-terminus of E1A 1-80 with vectors sequences that result in the addition of 39 non-adenoviral residues to the E1A 1-80 segment. This 39-residue segment (SEQ ID NO: 2) surprisingly increases the expression of E1A 1-80 from a commercial adenoviral vector (see Examples). This segment contains 23 non-polar, 5 acidic, 5 basic, 3 aromatic and 3 polar residues, and includes a V5 epitope. The entire fusion protein is provided in SEQ ID NO: 3.

F. Purification of Proteins

It will be desirable to purify E1A peptides. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fuctose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

G. Synthetic Peptides

Peptides of the invention can be synthesized in solution or on a solid support in accordance with conventional techniques. Various automatic synthesizers are commercially available and can be used in accordance with known protocols. See, for example, Stewart and Young (1984); Tam et al. (1983); Merrifield (1986); and Barany and Merrifield (1979), each incorporated herein by reference. Alternatively, recombinant DNA technology may be employed wherein a nucleotide sequence which encodes a peptide of the invention is inserted into an expression vector, transformed or transfected into an appropriate host cell and cultivated under conditions suitable for expression. Recombinant expression is discuss further, below, with relation to E1A encoding nucleic acids.

III. NUCLEIC ACIDS

The present invention also provides, in another embodiment, nucleic acids encoding E1A 1-80 and fragments thereof. Similarly, any reference to a nucleic acid should be read as encompassing a host cell containing that nucleic acid and, in some cases, capable of expressing the product of that nucleic acid.

A. Nucleic Acids Encoding E1A 1-80

Nucleic acids according to the present invention encode E1A 1-80, and optionally further include non-E1A sequences. The terms "substantially lacking further E1A sequences" and "consisting essentially of" as defined above with respect to peptides are also applicable, in comparable ways, to E1A nucleic acids.

As used in this application, the term "a nucleic acid encoding a E1A 1-80" refers to a nucleic acid molecule that has been isolated free of total cellular nucleic acid. In certain embodiments, the invention concerns a nucleic acid sequence essentially as set forth in SEQ ID NO:1. The term "as set forth in SEQ ID NO:1" means that the nucleic acid sequence substantially corresponds to a portion of SEQ ID NO:1. The term "functionally equivalent codon" is used herein to refer to codons that encode the same amino acid, such as the six codons for arginine or serine, and also refers to codons that encode biologically equivalent amino acids, as discussed in the following pages.

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of SEQ ID NO:1. Sequences that are essentially the same as those set forth in SEQ ID NO:1 also may be functionally defined as sequences that are capable of hybridizing to a nucleic acid segment containing the complement of SEQ ID NO:1 under standard conditions.

The DNA segments of the present invention include those encoding biologically functional equivalent E1A 1-80 proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

B. Vectors for Cloning, Gene Transfer and Expression

Within certain embodiments, expression vectors are employed to express an E1A 1-80 polypeptide or peptide product, an antisene, a ribozyme, an interfering RNA, or a single-chain antibody that binds immunologically to E1A 1-80. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (1989) and Ausubel et al. (1994), both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

(i) Regulatory Elements

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally-associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally-occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. One example is the native E1A 1-80 promoter. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Table 3 lists several elements/promoters that may be employed, in the context of the present invention, to regulate the expression of a gene. This list is not intended to be exhaustive of all the possible elements involved in the promotion of expression but, merely, to be exemplary thereof. Table 4 provides examples of inducible elements, which are regions of a nucleic acid sequence that can be activated in response to a specific stimulus.

TABLE 3

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al; 1990 |
| Immunoglobulin Light Chain | Queen et al., 1983; Picard et al., 1984 |
| T-Cell Receptor | Luria et al., 1987; Winoto et al., 1989; Redondo et al; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrook et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |

TABLE 3-continued

Promoter and/or Enhancer

| Promoter/Enhancer | References |
| --- | --- |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 4

Inducible Elements

| Element | Inducer | References |
| --- | --- | --- |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez at., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996). Tumor specific promoters also will find use in the present invention. Some such promoters are set forth in Table 5.

TABLE 5

Candidate Tissue-Specific Promoters

| Tissue-specific promoter | Cancers in which promoter is active | Normal cells in which promoter is active |
| --- | --- | --- |
| Carcinoembryonic antigen (CEA)* | Most colorectal carcinomas; 50% of lung carcinomas; 40-50% of gastric carcinomas; most pancreatic carcinomas; many breast carcinomas | Colonic mucosa; gastric mucosa; lung epithelia; eccrine sweat glands; cells in testes |

TABLE 5-continued

Candidate Tissue-Specific Promoters

| Tissue-specific promoter | Cancers in which promoter is active | Normal cells in which promoter is active |
|---|---|---|
| Prostate-specific antigen (PSA) | Most prostate carcinomas | Prostate epithelium |
| Vasoactive intestinal peptide (VIP) | Majority of non-small cell lung cancers | Neurons; lymphocytes; mast cells; eosinophils |
| Surfactant protein A (SP-A) | Many lung adenocarcinomas | Type II pneumocytes; Clara cells |
| Human achaete-scute homolog (hASH) | Most small cell lung cancers | Neuroendocrine cells in lung |
| Mucin-1 (MUC1)** | Most adenocarcinomas (originating from any tissue) | Glandular epithelial cells in breast and in respiratory, gastrointestinal, and genitourinary tracts |
| Alpha-fetoprotein | Most hepatocellular carcinomas; possibly many testicular cancers | Hepatocytes (under certain conditions); testis |
| Albumin | Most hepatocellular carcinomas | Hepatocytes |
| Tyrosinase | Most melanomas | Melanocytes; astrocytes; Schwann cells; some neurons |
| Tyrosine-binding protein (TRP) | Most melanomas | Melanocytes; astrocytes, Schwann cells; some neurons |
| Keratin 14 | Presumably many squamous cell carcinomas (e.g., Head and neck cancers) | Keratinocytes |
| EBV LD-2 | Many squamous cell carcinomas of head and neck | Keratinocytes of upper digestive Keratinocytes of upper digestive tract |
| Glial fibrillary acidic protein (GFAP) | Many astrocytomas | Astrocytes |
| Myelin basic protein (MBP) | Many gliomas | Oligodendrocytes |
| Testis-specific angiotensin-converting enzyme (Testis-specific ACE) | Possibly many testicular cancers | Spermatazoa |
| Osteocalcin | Possibly many osteosarcomas | Osteoblasts |
| E2F-regulated promoter | Almost all cancers | Proliferating cells |
| HLA-G | Many colorectal carcinomas; many melanomas; possibly many other cancers | Lymphocytes; monocytes; spermatocytes; trophoblast |
| FasL | Most melanomas; many pancreatic carcinomas; most astrocytomas possibly many other cancers | Activated leukocytes: neurons; endothelial cells; keratinocytes; cells in immunoprivileged tissues; some cells in lungs, ovaries, liver, and prostate |
| Myc-regulated promoter | Most lung carcinomas (both small cell and non-small cell); most colorectal carcinomas | Proliferating cells (only some cell-types): mammary epithelial cells (including non-proliferating) |
| MAGE-1 | Many melanomas; some non-small cell lung carcinomas; some breast carcinomas | Testis |
| VEGF | 70% of all cancers (constitutive overexpression in many cancers) | Cells at sites of neovascularization (but unlike in tumors, expression is transient, less strong, and never constitutive) |
| bFGF | Presumably many different cancers, since bFGF expression is induced by ischemic conditions | Cells at sites of ischemia (but unlike tumors, expression is transient, less strong, and never constitutive) |
| COX-2 | Most colorectal carcinomas; many lung carcinomas; possibly many other cancers | Cells at sites of inflammation |
| IL-10 | Most colorectal carcinomas; many lung carcinomas; many squamous cell carcinomas of head and neck; possibly many other cancers | Leukocytes |
| GRP78/BiP | Presumably many different cancers, since GRP7S expression is induced by tumor-specific conditions | Cells at sites of ishemia |

TABLE 5-continued

Candidate Tissue-Specific Promoters

| Tissue-specific promoter | Cancers in which promoter is active | Normal cells in which promoter is active |
|---|---|---|
| CarG elements from Egr-1 | Induced by ionization radiation, so conceivably most tumors upon irradiation | Cells exposed to ionizing radiation; leukocytes |

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

(ii) IRES

In certain embodiments of the invention, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

(iii) Multi-Purpose Cloning Sites

Vectors can include a multiple cloning site (MCS), which is a nucleic acid region that contains multiple restriction enzyme sites, any of which can be used in conjunction with standard recombinant technology to digest the vector. See Carbonelli et al., 1999, Levenson et al., 1998, and Cocea, 1997, incorporated herein by reference. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

(iv) Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see Chandler et al., 1997, herein incorporated by reference).

(v) Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

(vi) Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

(vii) Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

(viii) Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

(ix) Viral Vectors

The capacity of certain viral vectors to efficiently infect or enter cells, to integrate into a host cell genome and stably express viral genes, have led to the development and application of a number of different viral vector systems (Robbins et al., 1998). Viral systems are currently being developed for use as vectors for ex vivo and in vivo gene transfer. For example, adenovirus, herpes-simplex virus, retrovirus and adeno-associated virus vectors are being evaluated currently for treatment of diseases such as cancer, cystic fibrosis, Gaucher disease, renal disease and arthritis (Robbins and Ghivizzani, 1998; Imai et al., 1998; U.S. Pat. No. 5,670,488). The various viral vectors described below, present specific advantages and disadvantages, depending on the particular gene-therapeutic application.

Adenoviral Vectors.

In particular embodiments, an adenoviral expression vector is contemplated for the delivery of expression constructs. "Adenovirus expression vector" is meant to include those constructs containing adenovirus sequences sufficient to (a) support packaging of the construct and (b) to ultimately express a tissue or cell-specific construct that has been cloned therein.

Adenoviruses comprise linear, double-stranded DNA, with a genome ranging from 30 to 35 kb in size (Reddy et al., 1998; Morrison et al., 1997; Chillon et al., 1999). An adenovirus expression vector according to the present invention comprises a genetically engineered form of the adenovirus. Advantages of adenoviral gene transfer include the ability to infect a wide variety of cell types, including non-dividing cells, a mid-sized genome, ease of manipulation, high infectivity and the ability to be grown to high titers (Wilson, 1996). Further, adenoviral infection of host cells does not result in chromosomal integration because adenoviral DNA can replicate in an episomal manner, without potential genotoxicity associated with other viral vectors. Adenoviruses also are structurally stable (Marienfeld et al., 1999) and no genome rearrangement has been detected after extensive amplification (Parks et al., 1997; Bett et al., 1993).

Salient features of the adenovirus genome are an early region (E1, E2, E3 and E4 genes), an intermediate region (pIX gene, Iva2 gene), a late region (L1, L2, L3, L4 and L5 genes), a major late promoter (MLP), inverted-terminal-repeats (ITRs) and a $\Psi$ sequence (Zheng, et al., 1999; Robbins et al., 1998; Graham and Prevec, 1995). The early genes E1, E2, E3 and E4 are expressed from the virus after infection and encode polypeptides that regulate viral gene expression, cellular gene expression, viral replication, and inhibition of cellular apoptosis. Further on during viral infection, the MLP is activated, resulting in the expression of the late (L) genes, encoding polypeptides required for adenovirus encapsidation. The intermediate region encodes components of the adenoviral capsid. Adenoviral inverted terminal repeats (ITRs; 100-200 bp in length), are cis elements, and function as origins of replication and are necessary for viral DNA replication. The $\Psi$ sequence is required for the packaging of the adenoviral genome.

A common approach for generating adenoviruses for use as a gene transfer vectors is the deletion of the E1 gene (E1$^-$), which is involved in the induction of the E2, E3 and E4 promoters (Graham and Prevec, 1995). Subsequently, a therapeutic gene or genes can be inserted recombinantly in place of the E1 gene, wherein expression of the therapeutic gene(s) is driven by the E1 promoter or a heterologous promoter. The E1$^-$, replication-deficient virus is then proliferated in a "helper" cell line that provides the E1 polypeptides in trans (e.g., the human embryonic kidney cell line 293). Thus, in the present invention it may be convenient to introduce the transforming construct at the position from which the E1-coding sequences have been removed. It is important to note that replacement of E1-coding sequences by E1A 1-80 will not restore E1-coding sequence function in terms of viral replication. However, the position of insertion of the construct within the adenovirus sequences is not critical to the invention. Alternatively, the E3 region, portions of the E4 region or both may be deleted, wherein a heterologous nucleic acid sequence under the control of a promoter operable in eukaryotic cells is inserted into the adenovirus genome for use in gene transfer (U.S. Pat. No. 5,670,488; U.S. Pat. No. 5,932,210, each specifically incorporated herein by reference).

Although adenovirus based vectors offer several unique advantages over other vector systems, they often are limited by vector immunogenicity, size constraints for insertion of recombinant genes and low levels of replication. The preparation of a recombinant adenovirus vector deleted of all open reading frames, comprising a full length dystrophin gene and the terminal repeats required for replication (Haecker et al., 1997) offers some potentially promising advantages to the above mentioned adenoviral shortcomings. The vector was grown to high titer with a helper virus in 293 cells and was capable of efficiently transducing dystrophin in mdx mice, in myotubes in vitro and muscle fibers in vivo. Helper-dependent viral vectors are discussed below.

A major concern in using adenoviral vectors is the generation of a replication-competent virus during vector production in a packaging cell line or during gene therapy treatment of an individual. The generation of a replication-competent virus could pose serious threat of an unintended viral infection and pathological consequences for the patient. Armentano et al. (1990), describe the preparation of a replication-defective adenovirus vector, claimed to eliminate the potential for the inadvertent generation of a replication-competent adenovirus (U.S. Pat. No. 5,824,544, specifically incorporated herein by reference). The replication-defective adenovirus method comprises a deleted E1 region and a relocated protein IX gene, wherein the vector expresses a heterologous, mammalian gene. As stated previously, replacement of the E1-region by E1A 1-80 will not restore E1 function in terms of viral replication.

Other than the requirement that the adenovirus vector be replication defective, or at least conditionally defective, the nature of the adenovirus vector is not believed to be crucial to the successful practice of the invention. The adenovirus may be of any of the 42 different known serotypes and/or subgroups A-F. Adenovirus type 5 of subgroup C is the preferred starting material in order to obtain the conditional replication-defective adenovirus vector for use in the present invention. This is because adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Adenovirus growth and manipulation is known to those of skill in the art, and exhibits broad host range in vitro and in vivo (U.S. Pat. No. 5,670,488; U.S. Pat. No. 5,932,210; U.S. Pat. No. 5,824,544). This group of viruses can be obtained in high titers, e.g., $10^9$ to $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. Many experiments, innovations, preclinical studies and clinical trials are currently under investigation for the use of adenoviruses as gene delivery vectors. For example, adenoviral gene delivery-based gene therapies are being developed for liver diseases (Han et al., 1999), psychiatric diseases (Lesch, 1999), neurological diseases (Smith, 1998; Hermens and Verhaagen, 1998), coronary diseases (Feldman et al., 1996), muscular diseases (Petrof, 1998), gastrointestinal diseases (Wu, 1998) and various cancers such as colorectal (Fujiwara and Tanaka, 1998; Dorai et al., 1999), pancreatic, bladder (Irie et al., 1999), head and neck (Blackwell et al., 1999), breast (Stewart et al., 1999), lung (Batra et al., 1999) and ovarian (Vanderkwaak et al., 1999).

Retroviral Vectors.

In certain embodiments of the invention, the uses of retroviruses for gene delivery are contemplated. Retroviruses are RNA viruses comprising an RNA genome. When a host cell is infected by a retrovirus, the genomic RNA is reverse transcribed into a DNA intermediate which is integrated into the chromosomal DNA of infected cells. This integrated DNA intermediate is referred to as a provirus. A particular advantage of retroviruses is that they can stably infect dividing cells with a gene of interest (e.g., a therapeutic gene) by integrating into the host DNA, without expressing immunogenic viral proteins. Theoretically, the integrated retroviral vector will be maintained for the life of the infected host cell, expressing the gene of interest.

The retroviral genome and the proviral DNA have three genes: gag, pol, and env, which are flanked by two long terminal repeat (LTR) sequences. The gag gene encodes the internal structural (matrix, capsid, and nucleocapsid) proteins; the pol gene encodes the RNA-directed DNA polymerase (reverse transcriptase) and the env gene encodes viral envelope glycoproteins. The 5' and 3' LTRs serve to promote transcription and polyadenylation of the virion RNAs. The LTR contains all other cis-acting sequences necessary for viral replication.

A recombinant retrovirus of the present invention may be genetically modified in such a way that some of the structural, infectious genes of the native virus have been removed and replaced instead with a nucleic acid sequence to be delivered to a target cell (U.S. Pat. No. 5,858,744; U.S. Pat. No. 5,739,018, each incorporated herein by reference). After infection of a cell by the virus, the virus injects its nucleic acid into the cell and the retrovirus genetic material can integrate into the host cell genome. The transferred retrovirus genetic material is then transcribed and translated into proteins within the host cell. As with other viral vector systems, the generation of a replication-competent retrovirus during vector production or during therapy is a major concern. Retroviral vectors suitable for use in the present invention are generally defective retroviral vectors that are capable of infecting the target cell, reverse transcribing their RNA genomes, and integrating the reverse transcribed DNA into the target cell genome, but are incapable of replicating within the target cell to produce infectious retroviral particles (e.g., the retroviral genome transferred into the target cell is defective in gag, the gene encoding virion structural proteins, and/or in pol, the gene encoding reverse transcriptase). Thus, transcription of the provirus and assembly into infectious virus occurs in the presence of an appropriate helper virus or in a cell line containing appropriate sequences enabling encapsidation without coincident production of a contaminating helper virus.

The growth and maintenance of retroviruses is known in the art (U.S. Pat. No. 5,955,331; U.S. Pat. No. 5,888,502, each specifically incorporated herein by reference). Nolan et al. describe the production of stable high titre, helper-free retrovirus comprising a heterologous gene (U.S. Pat. No. 5,830,725, specifically incorporated herein by reference). Methods for constructing packaging cell lines useful for the generation of helper-free recombinant retroviruses with amphoteric or ecotrophic host ranges, as well as methods of using the recombinant retroviruses to introduce a gene of interest into eukaryotic cells in vivo and in vitro are contemplated in the present invention (U.S. Pat. No. 5,955,331).

Currently, the majority of all clinical trials for vector-mediated gene delivery use murine leukemia virus (MLV)-based retroviral vector gene delivery (Robbins et al., 1998; Miller et al., 1993). Disadvantages of retroviral gene delivery include a requirement for ongoing cell division for stable infection and a coding capacity that prevents the delivery of large genes. However, recent development of vectors such as lentivirus (e.g., HIV), simian immunodeficiency virus (SIV) and equine infectious-anemia virus (EIAV), which can infect certain non-dividing cells, potentially allow the in vivo use of retroviral vectors for gene therapy applications (Amado and Chen, 1999; Klimatcheva et al., 1999; White et al., 1999; Case et al., 1999). For example, HIV-based vectors have been used to infect non-dividing cells such as neurons (Miyatake et al., 1999), islets (Leibowitz et al., 1999) and muscle cells (Johnston et al., 1999). The therapeutic delivery of genes via retroviruses are currently being assessed for the treatment of various disorders such as inflammatory disease (Moldawer et al., 1999), AIDS (Amado and Chen, 1999; Engel and Kohn, 1999), cancer (Clay et al., 1999), cerebrovascular disease (Weihl et al., 1999) and hemophilia (Kay, 1998).

Herpesviral Vectors.

Herpes simplex virus (HSV) type I and type II contain a double-stranded, linear DNA genome of approximately 150 kb, encoding 70-80 genes. Wild type HSV are able to infect cells lytically and to establish latency in certain cell types (e.g., neurons). Similar to adenovirus, HSV also can infect a variety of cell types including muscle (Yeung et al., 1999), ear (Derby et al., 1999), eye (Kaufman et al., 1999), tumors (Yoon et al., 1999; Howard et al., 1999), lung (Kohut et al., 1998), neuronal (Garrido et al., 1999; Lachmann and Efstathiou, 1999), liver (Miytake et al., 1999; Kooby et al., 1999) and pancreatic islets (Rabinovitch et al., 1999).

HSV viral genes are transcribed by cellular RNA polymerase II and are temporally regulated, resulting in the transcription and subsequent synthesis of gene products in roughly three discernable phases or kinetic classes. These phases of genes are referred to as the Immediate Early (IE) or α genes, Early (E) or β genes and Late (L) or γ genes. Immediately following the arrival of the genome of a virus in the nucleus of a newly infected cell, the IE genes are transcribed. The efficient expression of these genes does not require prior viral protein synthesis. The products of IE genes are required to activate transcription and regulate the remainder of the viral genome.

For use in therapeutic gene delivery, HSV must be rendered replication-defective. Protocols for generating replication-defective HSV helper virus-free cell lines have been described (U.S. Pat. No. 5,879,934; U.S. Pat. No. 5,851,826, each specifically incorporated herein by reference in its entirety). One IE protein, ICP4, also known as α4 or Vmw175, is absolutely required for both virus infectivity and the transition from IE to later transcription. Thus, due to its complex, multifunctional nature and central role in the regulation of HSV gene expression, ICP4 has typically been the target of HSV genetic studies.

Phenotypic studies of HSV viruses deleted of ICP4 indicate that such viruses will be potentially useful for gene transfer purposes (Krisky et al., 1998a). One property of viruses deleted for ICP4 that makes them desirable for gene transfer is that they only express the five other IE genes: ICP0, ICP6, ICP27, ICP22 and ICP47 (DeLuca et al., 1985), without the expression of viral genes encoding proteins that direct viral DNA synthesis, as well as the structural proteins of the virus. This property is desirable for minimizing possible deleterious effects on host cell metabolism or an immune response following gene transfer. Further deletion of IE genes ICP22 and ICP27, in addition to ICP4, substantially improve reduction of HSV cytotoxicity and prevented early and late viral gene expression (Krisky et al., 1998b).

The therapeutic potential of HSV in gene transfer has been demonstrated in various in vitro model systems and in vivo for diseases such as Parkinson's (Yamada et al., 1999), retinoblastoma (Hayashi et al., 1999), intracerebral and intradermal tumors (Moriuchi et al., 1998), B-cell malignancies (Suzuki et al., 1998), ovarian cancer (Wang et al., 1998) and Duchenne muscular dystrophy (Huard et al., 1997).

Adeno-Associated Viral Vectors.

Adeno-associated virus (AAV), a member of the parvovirus family, is a human virus that is increasingly being used for gene delivery therapeutics. AAV has several advantageous features not found in other viral systems. First, AAV can infect a wide range of host cells, including non-dividing cells. Second, AAV can infect cells from different species. Third, AAV has not been associated with any human or animal disease and does not appear to alter the biological properties of the host cell upon integration. For example, it is estimated that 80-85% of the human population has been exposed to AAV. Finally, AAV is stable at a wide range of physical and chemical conditions which lends itself to production, storage and transportation requirements.

The AAV genome is a linear, single-stranded DNA molecule containing 4681 nucleotides. The AAV genome generally comprises an internal non-repeating genome flanked on each end by inverted terminal repeats (ITRs) of approximately 145 bp in length. The ITRs have multiple functions, including origins of DNA replication, and as packaging signals for the viral genome. The internal non-repeated portion of the genome includes two large open reading frames, known as the AAV replication (rep) and capsid (cap) genes. The rep and cap genes code for viral proteins that allow the virus to replicate and package the viral genome into a virion. A family of at least four viral proteins is expressed from the AAV rep region, Rep 78, Rep 68, Rep 52, and Rep 40, named according to their apparent molecular weight. The AAV cap region encodes at least three proteins, VP1, VP2, and VP3.

AAV is a helper-dependent virus requiring co-infection with a helper virus (e.g., adenovirus, herpesvirus or vaccinia) in order to form AAV virions. In the absence of co-infection with a helper virus, AAV establishes a latent state in which the viral genome inserts into a host cell chromosome, but infectious virions are not produced. Subsequent infection by a helper virus "rescues" the integrated genome, allowing it to replicate and package its genome into infectious AAV virions. Although AAV can infect cells from different species, the helper virus must be of the same species as the host cell (e.g., human AAV will replicate in canine cells co-infected with a canine adenovirus).

AAV has been engineered to deliver genes of interest by deleting the internal non-repeating portion of the AAV genome and inserting a heterologous gene between the ITRs. The heterologous gene may be functionally linked to a heterologous promoter (constitutive, cell-specific, or inducible) capable of driving gene expression in target cells. To produce infectious recombinant AAV (rAAV) containing a heterologous gene, a suitable producer cell line is transfected with a rAAV vector containing a heterologous gene. The producer cell is concurrently transfected with a second plasmid harboring the AAV rep and cap genes under the control of their respective endogenous promoters or heterologous promoters. Finally, the producer cell is infected with a helper virus.

Once these factors come together, the heterologous gene is replicated and packaged as though it were a wild-type AAV genome. When target cells are infected with the resulting rAAV virions, the heterologous gene enters and is expressed in the target cells. Because the target cells lack the rep and cap genes and the adenovirus helper genes, the rAAV cannot further replicate, package or form wild-type AAV.

The use of helper virus, however, presents a number of problems. First, the use of adenovirus in a rAAV production system causes the host cells to produce both rAAV and infectious adenovirus. The contaminating infectious adenovirus can be inactivated by heat treatment (56° C. for 1 hour). Heat treatment, however, results in approximately a 50% drop in the titer of functional rAAV virions. Second, varying amounts of adenovirus proteins are present in these preparations. For example, approximately 50% or greater of the total protein obtained in such rAAV virion preparations is free adenovirus fiber protein. If not completely removed, these adenovirus proteins have the potential of eliciting an immune response from the patient. Third, AAV vector production methods which employ a helper virus require the use and manipulation of large amounts of high titer infectious helper virus, which presents a number of health and safety concerns, particularly in regard to the use of a herpesvirus. Fourth, concomitant production of helper virus particles in rAAV virion producing cells diverts large amounts of host cellular resources away from rAAV virion production, potentially resulting in lower rAAV virion yields.

Lentiviral Vectors.

Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. The lentiviral genome and the proviral DNA have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx.

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA. However, the resulting mutant remains capable of directing the synthesis of all virion proteins.

Lentiviral vectors are known in the art, see Naldini et al., (1996); Zufferey et al., (1997); U.S. Pat. Nos. 6,013,516; and 5,994,136. In general, the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest.

Recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. This describes a first vector that can provide a nucleic acid encoding a viral gag and a pol gene and another vector that can provide a nucleic acid encoding a viral env to produce a packaging cell. Introducing a vector providing a heterologous gene, such as the STAT-1α gene in this invention, into that packaging cell yields a producer cell which releases infectious viral particles carrying the foreign gene of interest. The env preferably is an amphotropic envelope protein which allows transduction of cells of human and other species.

One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

The vector providing the viral env nucleic acid sequence is associated operably with regulatory sequences, e.g., a promoter or enhancer. The regulatory sequence can be any eukaryotic promoter or enhancer, including for example, the Moloney murine leukemia virus promoter-enhancer element, the human cytomegalovirus enhancer or the vaccinia P7.5 promoter. In some cases, such as the Moloney murine leukemia virus promoter-enhancer element, the promoter-enhancer elements are located within or adjacent to the LTR sequences.

The heterologous or foreign nucleic acid sequence, such as the STAT-1α encoding polynucleotide sequence herein, is linked operably to a regulatory nucleic acid sequence. Preferably, the heterologous sequence is linked to a promoter, resulting in a chimeric gene. The heterologous nucleic acid sequence may also be under control of either the viral LTR promoter-enhancer signals or of an internal promoter, and retained signals within the retroviral LTR can still bring about efficient expression of the transgene. Marker genes may be utilized to assay for the presence of the vector, and thus, to confirm infection and integration. The presence of a marker gene ensures the selection and growth of only those host cells which express the inserts. Typical selection genes encode proteins that confer resistance to antibiotics and other toxic substances, e.g., histidinol, puromycin, hygromycin, neomycin, methotrexate, etc., and cell surface markers.

The vectors are introduced via transfection or infection into the packaging cell line. The packaging cell line produces viral particles that contain the vector genome. Methods for transfection or infection are well known by those of skill in the art. After cotransfection of the packaging vectors and the transfer vector to the packaging cell line, the recombinant virus is recovered from the culture media and titered by standard methods used by those of skill in the art. Thus, the packaging constructs can be introduced into human cell lines by calcium phosphate transfection, lipofection or electroporation, generally together with a dominant selectable marker, such as neo, DHFR, Gln synthetase or ADA, followed by selection in the presence of the appropriate drug and isolation of clones. The selectable marker gene can be linked physically to the packaging genes in the construct.

Lentiviral transfer vectors Naldini et al. (1996), have been used to infect human cells growth-arrested in vitro and to transduce neurons after direct injection into the brain of adult rats. The vector was efficient at transferring marker genes in vivo into the neurons and long term expression in the absence of detectable pathology was achieved. Animals analyzed ten months after a single injection of the vector showed no decrease in the average level of transgene expression and no sign of tissue pathology or immune reaction (Blomer et al., 1997). Thus, in the present invention, one may graft or transplant cells infected with the recombinant lentivirus ex vivo, or infect cells in vivo.

Other Viral Vectors.

The development and utility of viral vectors for gene delivery is constantly improving and evolving. Other viral vectors such as poxvirus; e.g., vaccinia virus (Gnant et al., 1999; Gnant et al., 1999), alpha virus; e.g., sindbis virus, Semliki forest virus (Lundstrom, 1999), reovirus (Coffey et al., 1998) and influenza A virus (Neumann et al., 1999) are contemplated for use in the present invention and may be selected according to the requisite properties of the target system.

In certain embodiments, vaccinia viral vectors are contemplated for use in the present invention. Vaccinia virus is a particularly useful eukaryotic viral vector system for expressing heterologous genes. For example, when recombinant vaccinia virus is properly engineered, the proteins are synthesized, processed and transported to the plasma membrane. Vaccinia viruses as gene delivery vectors have recently been demonstrated to transfer genes to human tumor cells, e.g., EMAP-II (Gnant et al., 1999), inner ear (Derby et al., 1999), glioma cells, e.g., p53 (Timiryasova et al., 1999) and various mammalian cells, e.g., $P_{450}$ (U.S. Pat. No. 5,506,138). The preparation, growth and manipulation of vaccinia viruses are described in U.S. Pat. No. 5,849,304 and U.S. Pat. No. 5,506,138 (each specifically incorporated herein by reference).

In other embodiments, sindbis viral vectors are contemplated for use in gene delivery.

Sindbis virus is a species of the alphavirus genus (Garoff and Li, 1998) which includes such important pathogens as Venezuelan, Western and Eastern equine encephalitis viruses (Sawai et al., 1999; Mastrangelo et al., 1999). In vitro, sindbis virus infects a variety of avian, mammalian, reptilian, and amphibian cells. The genome of sindbis virus consists of a single molecule of single-stranded RNA, 11,703 nucleotides in length. The genomic RNA is infectious, is capped at the 5' terminus and polyadenylated at the 3' terminus, and serves as mRNA. Translation of a vaccinia virus 26S mRNA produces a polyprotein that is cleaved co- and post-translationally by a combination of viral and presumably host-encoded proteases to give the three virus structural proteins, a capsid protein (C) and the two envelope glycoproteins (E1 and PE2, precursors of the virion E2).

Three features of sindbis virus suggest that it would be a useful vector for the expression of heterologous genes. First, its wide host range, both in nature and in the laboratory. Second, gene expression occurs in the cytoplasm of the host cell and is rapid and efficient. Third, temperature-sensitive mutations in RNA synthesis are available that may be used to modulate the expression of heterologous coding sequences by simply shifting cultures to the non-permissive temperature at various time after infection. The growth and maintenance of sindbis virus is known in the art (U.S. Pat. No. 5,217,879, specifically incorporated herein by reference).

Chimeric Viral Vectors.

Chimeric or hybrid viral vectors are being developed for use in therapeutic gene delivery and are contemplated for use in the present invention. Chimeric poxviral/retroviral vectors (Holzer et al., 1999), adenoviral/retroviral vectors (Feng et al., 1997; Bilbao et al., 1997; Caplen et al., 1999) and adenoviral/adeno-associated viral vectors (Fisher et al., 1996; U.S. Pat. No. 5,871,982) have been described.

These "chimeric" viral gene transfer systems can exploit the favorable features of two or more parent viral species. For example, Wilson et al., provide a chimeric vector construct which comprises a portion of an adenovirus, AAV 5' and 3' ITR sequences and a selected transgene, described below (U.S. Pat. No. 5,871,983, specifically incorporate herein by reference).

The adenovirus/AAV chimeric virus uses adenovirus nucleic acid sequences as a shuttle to deliver a recombinant AAV/transgene genome to a target cell. The adenovirus nucleic acid sequences employed in the hybrid vector can range from a minimum sequence amount, which requires the use of a helper virus to produce the hybrid virus particle, to only selected deletions of adenovirus genes, which deleted gene products can be supplied in the hybrid viral production process by a selected packaging cell. At a minimum, the adenovirus nucleic acid sequences employed in the pAdA shuttle vector are adenovirus genomic sequences from which all viral genes are deleted and which contain only those adenovirus sequences required for packaging adenoviral genomic DNA into a preformed capsid head. More specifically, the adenovirus sequences employed are the cis-acting 5' and 3' inverted terminal repeat (ITR) sequences of an adenovirus (which function as origins of replication) and the native 5' packaging/enhancer domain, that contains sequences necessary for packaging linear Ad genomes and enhancer elements for the E1 promoter. The adenovirus sequences may be modified to contain desired deletions, substitutions, or mutations, provided that the desired function is not eliminated.

The AAV sequences useful in the above chimeric vector are the viral sequences from which the rep and cap polypeptide encoding sequences are deleted. More specifically, the AAV sequences employed are the cis-acting 5' and 3' inverted terminal repeat (ITR) sequences. These chimeras are characterized by high titer transgene delivery to a host cell and the ability to stably integrate the transgene into the host cell chromosome (U.S. Pat. No. 5,871,983, specifically incorporate herein by reference). In the hybrid vector construct, the AAV sequences are flanked by the selected adenovirus sequences discussed above. The 5' and 3' AAV ITR sequences themselves flank a selected transgene sequence and associated regulatory elements, described below. Thus, the sequence formed by the transgene and flanking 5' and 3' AAV sequences may be inserted at any deletion site in the adenovirus sequences of the vector. For example, the AAV sequences are desirably inserted at the site of the deleted E1a/E1b genes of the adenovirus. Alternatively, the AAV sequences may be inserted at an E3 deletion, E2a deletion, and so on. If only the adenovirus 5' ITR/packaging sequences and 3' ITR sequences are used in the hybrid virus, the AAV sequences are inserted between them.

The transgene sequence of the vector and recombinant virus can be a gene, a nucleic acid sequence or reverse transcript thereof, heterologous to the adenovirus sequence, which encodes a protein, polypeptide or peptide fragment of interest. The transgene is operatively linked to regulatory components in a manner which permits transgene transcription. The composition of the transgene sequence will depend upon the use to which the resulting hybrid vector will be put. For example, one type of transgene sequence includes a therapeutic gene which expresses a desired gene product in a host cell. These therapeutic genes or nucleic acid sequences typically encode products for administration and expression in a patient in vivo or ex vivo to replace or correct an inherited or non-inherited genetic defect or treat an epigenetic disorder or disease.

(x) Non-Viral Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994, 624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384, 253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

Injection.

In certain embodiments, a nucleic acid may be delivered to an organelle, a cell, a tissue or an organism via one or more injections (i.e., a needle injection), such as, for example, either subcutaneously, intradermally, intramuscularly, intravenously or intraperitoneally. Methods of injection of vaccines are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into *Xenopus* oocytes (Harland and Weintraub, 1985).

Electroporation.

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human κ-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon-derived protoplasts is described by Dhir and Widholm in International Patent Application No. WO 92/17598, incorporated herein by reference. Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

Calcium Phosphate.

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

DEAE-Dextran: In another embodiment, a nucleic acid is delivered into a cell using DEAE-dextran followed by polyethylene glycol. In this manner, reporter plasmids were introduced into mouse myeloma and erythroleukemia cells (Gopal, 1985).

Sonication Loading.

Additional embodiments of the present invention include the introduction of a nucleic acid by direct sonic loading. LTK⁻ fibroblasts have been transfected with the thymidine kinase gene by sonication loading (Fechheimer et al., 1987).

Liposome-Mediated Transfection.

In a further embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

Receptor-Mediated Transfection.

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

C. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented.

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

IV. DIAGNOSING CANCERS INVOLVING HER2/NEU

In another embodiment, the present invention involves diagnostic methods for assessing expression, or overexpression of HER2/Neu in a cancer. Such cancers are of particular relevance to treatments involving E1A 1-80. Such cancer may involve cancers of the brain (glioblastomas, medulloblastoma, astrocytoma, oligodendroglioma, ependymomas), lung, liver, spleen, kidney, pancreas, small intestine, blood cells, lymph node, colon, breast, endometrium, stomach, prostate, testicle, ovary, skin, head and neck, esophagus, bone marrow, blood or other tissue. In particular, the present invention relates to the diagnosis of breast cancers.

The biological sample can be any tissue or fluid. Various embodiments include cells of the skin, muscle, facia, brain, prostate, breast, endometrium, lung, head & neck, pancreas, small intestine, blood cells, liver, testes, ovaries, colon, skin, stomach, esophagus, spleen, lymph node, bone marrow or kidney. Other embodiments include fluid samples such as peripheral blood, lymph fluid, ascites, serous fluid, pleural effusion, sputum, cerebrospinal fluid, lacrimal fluid, stool or urine.

A. Genetic Diagnosis

In one embodiment, the diagnosis may focus on nucleic acids, in particular, by examining DNA duplication or mRNA expression. Nucleic acid used is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given patient with a statistically significant reference group of normal patients and patients that have HER2/neu-related cancers. In this way, it is possible to correlate the amount of HER2/neu detected with various clinical states.

(i) Primers and Probes

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process. In particular embodiments, the probes or primers are labeled with radioactive species ($^{32}$P, $^{14}$C, $^{35}$S, $^{3}$H, or other label), with a fluorophore (rhodamine, fluorescein) or a chemillumiscent (luciferase).

(ii) Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in its entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al. (1989). Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPO No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992).

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR™-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double-stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single-stranded DNA, which is then converted to double stranded DNA, and then transcribed once again with an RNA polymerase such as T7 or SP6. The resulting products, whether truncated or complete, indicate target specific sequences.

Davey et al., EPO No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR™" (Frohman, 1990; Ohara et al., 1989; each herein incorporated by reference in their entirety).

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., (1989), incorporated herein by reference in its entirety.

(iii) Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will bind a portion of the target sequence under renaturing conditions. Unbound probe is then removed, and detection is accomplished as described above.

(iv) Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

(v) Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols. See Sambrook et al. (1989). For example, chromophore or radiolabel probes or primers identify the target during or following amplification.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al, 1994). The present invention provides methods by which any or all of these types of analyses may be used. Using the sequences disclosed herein, oligonucleotide primers may be designed to permit the amplification of HER2/neu sequences that may then be analyzed by direct sequencing.

(vi) Kit Components

All the essential materials and reagents required for detecting and sequencing HER2/neu and variants thereof may be assembled together in a kit. This generally will comprise preselected primers and probes. Also included may be enzymes suitable for amplifying nucleic acids including various polymerases (RT, Taq, Sequenase™ etc.), deoxynucleotides and buffers to provide the necessary reaction mixture for amplification. Such kits also generally will comprise, in suitable means, distinct containers for each individual reagent and enzyme as well as for each primer or probe.

(vii) Design and Theoretical Considerations for Relative Quantitative RT-PCR™

Reverse transcription (RT) of RNA to cDNA followed by relative quantitative PCR™ (RT-PCR™) can be used to determine the relative concentrations of specific mRNA species isolated from patients. By determining that the concentration of a specific mRNA species varies, it is shown that the gene encoding the specific mRNA species is differentially expressed.

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR™ products and the relative mRNA abundances is only true in the linear range of the PCR™ reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR™ for a collection of RNA populations is that the concentrations of the amplified PCR™ products must be sampled when the PCR™ reactions are in the linear portion of their curves.

The second condition that must be met for an RT-PCR™ experiment to successfully determine the relative abundances of a particular mRNA species is that relative concentrations of the amplifiable cDNAs must be normalized to some independent standard. The goal of an RT-PCR™ experiment is to determine the abundance of a particular mRNA species relative to the average abundance of all mRNA species in the sample. In the experiments described below, mRNAs for β-actin, asparagine synthetase and lipocortin II were used as external and internal standards to which the relative abundance of other mRNAs are compared.

Most protocols for competitive PCR™ utilize internal PCR™ standards that are approximately as abundant as the target. These strategies are effective if the products of the PCR™ amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR™ assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR™ is performed as a relative quantitative RT-PCR™ with an internal standard in which the internal standard is an amplifiable cDNA fragment that is larger than the target cDNA fragment and in which the abundance of the mRNA encoding the internal standard is roughly 5-100 fold higher than the mRNA encoding the target. This assay measures relative abundance, not absolute abundance of the respective mRNA species.

Other studies may be performed using a more conventional relative quantitative RT-PCR™ assay with an external standard protocol. These assays sample the PCR™ products in the linear portion of their amplification curves. The number of PCR™ cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR™ assays can be superior to those derived from the relative quantitative RT-PCR™ assay with an internal standard.

One reason for this advantage is that without the internal standard/competitor, all of the reagents can be converted into a single PCR™ product in the linear range of the amplification curve, thus increasing the sensitivity of the assay. Another reason is that with only one PCR™ product, display of the product on an electrophoretic gel or another display method becomes less complex, has less background and is easier to interpret.

(viii) Chip Technologies

Specifically contemplated by the present inventors are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization. See also Pease et al. (1994); Fodor et al. (1991).

B. Immunodiagnosis

Another diagnostic approach is to examine protein expression through techniques such as ELISAs and Western blotting. In particular, the use of antibodies in an ELISA assay is contemplated. For example, anti-HER2/Neu antibodies are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for HER2/Neu that differs from the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera are then allowed to incubate for from about 2 to about 4 hr, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The antibody compositions of the present invention will find great use in immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard.

V. METHODS OF THERAPY

The present invention also involves, in another embodiment, the treatment of cancer. Any type of cancer that may be treated, but in accordance with the present invention, there is particular relevance to the involvement of HER2/Neu. Thus, it is contemplated that a wide variety of tumors may be treated using E1A 1-80 constructs, including cancers of the brain, lung, liver, spleen, kidney, lymph node, pancreas, small intestine, blood cells, colon, stomach, breast, endometrium, prostate, testicle, ovary, skin, head and neck, esophagus, bone marrow, blood or other tissue.

In many contexts, it is not necessary that the tumor cell be killed or induced to undergo normal cell death or "apoptosis." Rather, to accomplish a meaningful treatment, all that is required is that the tumor growth be slowed to some degree. It may be that the tumor growth is completely blocked, however, or that some tumor regression is achieved. Clinical terminology such as "remission" and "reduction of tumor" burden also are contemplated given their normal usage.

The present invention contemplates the use of E1A 1-80 as a single-agent therapy against cancers that exhibit elevated HER2/Neu ("HER2/Neu overexpression"). It may also be used in combination with one or more additional anti-cancer therapies, such as radio-, chemo-, immuno-, hormonal, or toxin therapy. However, in particular, the invention is designed to function in combination with HER2/Neu targeting agents.

A. Genetic Based Therapies

One of the therapeutic embodiments contemplated by the present inventors is the intervention, at the molecular level, in the events involved in tumorigenesis. Specifically, the present inventors intend to provide, to a cancer cell, an expression construct capable expressing E1A 1-80 in that cell. The lengthy discussion of expression vectors and the genetic elements employed therein is incorporated into this section by reference. Particular expression vectors are viral vectors such as adenovirus, adeno-associated virus, herpesvirus, vaccinia virus and retrovirus. Also contemplated are liposomally-encapsulated expression vectors.

Those of skill in the art are well aware of how to apply gene delivery to in vivo and ex vivo situations. For viral vectors, one generally will prepare a viral vector stock. Depending on the kind of virus and the titer attainable, one will deliver $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for various tumor types. The section below on routes contains an extensive list of possible routes. For practically any tumor, systemic delivery is contemplated. This will prove especially important for attacking microscopic or metastatic cancer. Where discrete tumor mass may be identified, a variety of direct, local and regional approaches may be taken. For example, the tumor may be directly injected with the expression vector. A tumor bed may be treated prior to, during or after resection. Following resection, one generally will deliver the vector by a catheter left in place following surgery. One may utilize the tumor vasculature to introduce the vector into the tumor by injecting a supporting vein or artery. A more distal blood supply route also may be utilized.

In a different embodiment, ex vivo gene therapy is contemplated. This approach is particularly suited, although not limited, to treatment of bone marrow associated cancers. In an ex vivo embodiment, cells from the patient are removed and maintained outside the body for at least some period of time. During this period, a therapy is delivered, after which the cells are reintroduced into the patient; hopefully, any tumor cells in the sample have been killed.

Autologous bone marrow transplant (ABMT) is an example of ex vivo gene therapy. Basically, the notion behind ABMT is that the patient will serve as his or her own bone marrow donor. Thus, a normally lethal dose of irradiation or chemotherapeutic may be delivered to the patient to kill tumor cells, and the bone marrow repopulated with the patients own cells that have been maintained (and perhaps expanded) ex vivo. Because, bone marrow often is contaminated with tumor cells, it is desirable to purge the bone marrow of these cells. Use of gene therapy to accomplish this goal is yet another way E1A 1-80 may be utilized according to the present invention.

B. Protein Therapy

Another therapy approach is the provision, to a subject, of E1A 1-80 polypeptide, mimetic or other analogs thereof. The protein/peptide may be produced by recombinant expression means or, if small enough, generated by an automated peptide synthesizer. Formulations would be selected based on the route of administration and purpose including, but not limited to, liposomal formulations and classic pharmaceutical preparations.

C. Combinations

In the context of the present invention, it also is contemplated that E1A 1-80 therapy could be used similarly in conjunction with chemo- or radiotherapeutic intervention. It also may prove effective to combine E1A 1-80 therapy with anti-HER-2/Neu therapies or other therapies such as traditional chemo- or radiotherapy.

To kill cells, inhibit cell growth, inhibit metastasis, inhibit angiogenesis or otherwise reverse or reduce the malignant phenotype of tumor cells, using the methods and compositions of the present invention, one would generally contact a "target" cell with a E1A 1-80 therapy and at least one other agent. These compositions would be provided in a combined amount effective to kill or inhibit proliferation of the cell. This process may involve contacting the cells with the E1A 1-80 and the other agent(s) or factor(s) at the same time. This may be achieved by contacting the cell with a single composition or pharmacological formulation that includes both agents, or by contacting the cell with two distinct compositions or formulations, at the same time, wherein one composition includes the E1A 1-80 and the other includes the other agent.

Alternatively, the E1A 1-80 therapy may precede or follow the other agent treatment by intervals ranging from minutes to weeks. In embodiments where the other agent and E1A 1-80 are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either E1A 1-80 or the other agent will be desired. Various combinations may be employed, where E1A 1-80 therapy is "A" and the other therapy is "B", as exemplified below:

| A/B/A | B/A/B | B/B/A | A/A/B | B/A/A | A/B/B |
|---|---|---|---|---|---|
| B/B/B/A | B/B/A/B | A/A/B/B | A/B/A/B | A/B/B/A | B/B/B/A |
| B/A/B/A | B/A/A/B | B/B/B/A | A/A/A/B | B/A/A/A | A/B/A/A |
| A/A/B/A | A/B/B/B | B/A/B/B | B/B/A/B | | |

Other combinations are contemplated. Again, to achieve cell killing, both agents are delivered to a cell in a combined amount effective to kill the cell.

Agents or factors suitable for use in a combined therapy are any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide.

In treating cancer according to the invention, one would contact the tumor cells with an agent in addition to the expression construct. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or cisplatin. The agent may be prepared and used as a combined therapeutic composition, or kit, by combining it with an E1A 1-80 therapy, as described above.

Agents that directly cross-link nucleic acids, specifically DNA, are envisaged to facilitate DNA damage leading to a synergistic, antineoplastic combination with an E1A 1-80 therapy. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for adriamycin, to 35-50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells.

Other forms of DNA damaging factors are also contemplated such as microwaves and UV-irradiation. It is most likely that all of these factors affect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the local or regional delivery of E1A 1-80 to patients with cancer will be a very efficient method for treating the clinical disease. Similarly, the chemo- or radiotherapy may be directed to a particular, affected region of the subjects body. Alternatively, systemic delivery of expression construct and/or the agent may be appropriate in certain circumstances, for example, where extensive metastasis has occurred.

In a particular embodiment, the present invention contemplates the use of E1A 1-80 therapies with a HER-2/Neu therapy like trastuzumab. Trastuzumab (more commonly known under the trade name Herceptin®) is a humanized monoclonal antibody that acts on the extracellular portion of the HER2/Neu (ERBB2) receptor. Trastuzumab's principal use is as an anti-cancer therapy in breast cancer in patients whose tumors over express (produce more than the usual amount of) this receptor. Trastuzumab is administered either once a week or once every three weeks intravenously for 30 to 90 minutes. Amplification of ERBB2 occurs in 25-30% of early-stage breast cancers. It encodes the transmembrane tyrosine kinase p185-erbB2 glycoprotein. Overexpression of HER2/Neu can confer therapeutic resistance to cancer therapies.

Cells treated with trastuzumab undergo arrest during the G1 phase of the cell cycle so there is reduced proliferation. It has been suggested that trastuzumab induces some of its effect by downregulation of ERBB2 leading to disruption of receptor dimerization and signaling through the downstream PI3K cascade. P27Kip1 is then not phosphorylated and is able to enter the nucleus and inhibit CDK2 activity, causing cell cycle arrest. Also, trastuzumab suppresses angiogenesis by both induction of anti-angiogenic factors and repression of proangiogenic factors. It is thought that a contribution to the unregulated growth observed in cancer could be due to proteolytic cleavage of ERBB2 that results in the release of the extracellular domain. Trastuzumab has been shown to inhibit ERBB2 ectodomain cleavage in breast cancer cells. There may be other undiscovered mechanisms by which trastuzumab induces regression in cancer.

Initiation of trastuzumab therapy is based upon the identification of HER-2 overexpression. Various methodologies have been developed to identify overexpression of HER-2. In the routine clinical laboratory, the most commonly employed methods are immunohistochemistry (IHC) and either chromogenic or fluorescent in situ hybridization (CISH/FISH). In addition numerous PCR-based methodologies have also been described.

The optimal duration of adjuvant trastuzumab is currently unknown. One year of treatment is generally accepted as the ideal length of therapy based on current clinical trial evidence that demonstrated the superiority of one year treatment over none. However, a small Finnish trial also showed similar improvement with nine weeks' of treatment over no therapy. Due to the lack of direct head to head comparison in clinical trials, it is unknown whether a shorter duration of treatment may just be as effective (with less side effects) than the current accepted practice of treatment for one year. Debate about treatment duration has become a relevant issue for many public health policy makers due to the high financial costs involved in the administration of this treatment for one year. Some countries with a free public health system such as New Zealand, has opted to only fund for nine weeks of adjuvant therapy as a result.[14] Current clinical trials are in progress hoping to answer this question by directly comparing short versus long duration of therapy.

One of the significant complications of trastuzumab is its effect on the heart. Trastuzumab is associated with cardiac dysfunction in 2-7% of cases. Approximately 10% of patients are unable to tolerate this drug because of pre-existing heart problems; physicians are balancing the risk of recurrent cancer against the higher risk of death due to cardiac disease in this population. The risk of cardiomyopathy is increased when trastuzumab is combined with anthracycline chemotherapy (which itself is associated with cardiac toxicity). The present invention thus contemplates the use of lower doses of trastuzumab when used in combination with E1A 1-80, thereby avoiding this toxicity. In addition, trastuzumab costs about seventy thousand U.S. dollars for a full course of treatment. The ability to reduce trastuzumab doses can also reduce cost.

In addition to combining an E1A 1-80 therapy with chemo-, radio- and Herceptin® therapies, it also is contemplated that combination with gene therapies will be advantageous. For example, treatment of tumors with E1A 1-80 and a gene therapy targeting p53 mutations at the same time may produce an improved anti-cancer treatment. Any other tumor-related gene conceivably can be targeted in this manner, for example, p21, Rb, APC, DCC, NF-1, NF-2, BCRA2, p16, FHIT, WT-1, MEN-I, MEN-II, BRCA1, VHL, FCC, MCC, ras, myc, raf, erb, src, fms, jun, trk, ret, gsp, hst, bcl and abl.

D. Formulations and Routes for Administration to Patients

Where clinical applications are contemplated, it will be necessary to prepare pharmaceutical compositions—expression vectors, virus stocks, proteins, peptides, antibodies and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, or in a resected tumor bed.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

VI. KITS

According to the present invention, there are provided kits for detecting HER2 expression. The kit of the present invention can be prepared by known materials and techniques which are conventionally used in the art. Generally, kits comprise separate vials or containers for the various reagents, such as probes, primers, enzymes, antibodies, etc. The reagents are also generally prepared in a form suitable for preservation by dissolving it in a suitable solvent. Examples

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials & Methods

Plasmids and Transfections.

pHER2-533 expressing the luciferase gene driven by the HER2 promoter (Yu et al., 2002) was used as reporter. E1A 243R was PCR cloned into the expression vector pDest47 (Invitrogen) or E1A 243R and E1A 1-80 were PCR cloned into pcDNA3 (Invitrogen) using appropriate primers and pLE2 dl320, a plasmid containing genomic E1A with a splice-point mutation causing only 243R to be transcribed, as template (Green et al., 2008; Howe et al., 1990). MCF-10A (ATCC) cells were transfected in 24-well plates with a total of 500 ng of DNA using lipofectamine (Invitrogen) and the manufacturer's guidelines. SK-BR-3 (ATCC) cells in 60 mm$^2$ cell culture dishes were transfected with a total of 1 µg of DNA using Fugene (Roche) and the manufacturer's guidelines. Cells were harvested 48 h post transfection and luciferase gene expression quantified after normalization against expression of a co-transfected non-E1A repressible RTL-luc using a Dual-Luciferase assay kit (Promega) and a Turner Design luminometer.

Adenovirus Vectors.

E1A 243R, E1A 243R mutants with stop codons and E1A 1-80 with or without a stop codon were cloned into the Gateway (Invitrogen) entry vector pENTR/SD/D-TOPO following the manufacturer's instructions. After sequence confirmation, E1A inserts were transferred into pAd/CMV/V5 DEST (Invitrogen). E1A 243R, the triple mutant E1A 243R dl1101/dl1108/dl1135 or E1A 1-80 cloned into the entry vector with a stop codon transcribes their respective E1A moiety under the control of the CMV promoter. E1A 1-80 cloned without a stop codon transcribes E1A 1-80 with an additional 36 amino acids at its C-terminus. The pAd CMV plasmids were digested with PacI and transfected into 293A cells (Invitrogen). Resultant Ad vectors were amplified, purified on CsCl density gradients and titrated by plaque assay as described (Green and Loewenstein, 2005).

HER2RNA Repression Assays.

SK-BR-3 cells, about 60% confluent, in 6-well cell culture plates were infected in 2 ml of DME/10% FBS with AdCMV E1A 243R or AdCMV ETA 1-80 at 37° C. in a humidified incubator. After 1 h, 2 ml of complete medium was added and incubation continued for an additional 36 to 48 h and cells harvested by scraping into 1 ml of cold PBS. Cells were washed once in PBS and RNA isolated using an RNA Easy kit (QIAGEN). cDNA was prepared using a High Capacity cDNA Archive kit (Applied Biosystems). Levels of HER2 cDNA were measured by quantitative RT-PCR with a HER2 specific TaqMan probe-set (Applied Biosystems) using an Opticon 2 real-time PCR instrument (Bio-Rad).

Western Blots and Pulse-Chase Analysis.

For Western blots, A549 cells in 60 mm$^2$ cell culture dishes were infected with the indicated amounts of AdCMV ETA 1-80 or AdCMV E1A 1-80C+ (a modified E1A 1-80 which expresses the E1A repressor at very high levels), see Results. Cells were harvested 48 h post infection and subjected to SDS PAGE. Electroblots were probed by antibody specific for the E1A CR1 domain (PD1) (Boyd et al., 2002). Immunoblots were developed using a Super Signal Western Blot Chemoluminescence Kit (Pierce).

For pulse-chase experiments, A549 cells in replicate 10 cm$^2$ cell culture plates were mock infected or infected with 100 moi (multiplicity of infection) of AdCMV vector expressing E1A 243R, E1A 1-80 or E1A 1-80C+. At 20 h after infection, cells were washed in PBS and starved for 1 h in DME lacking cysteine/methionine and containing 10% dialyzed FBS. Cells were then labeled for 90 min with 100 µCi/plate of $^{35}$S-labeled methionine/cysteine (Tran-S label, MP Biochemicals) and then washed and chased for various times with complete DME/10% FBS.

Cell Proliferation Assays.

Human breast cancer SK-BR-3 cells (2,000/well) were plated in DME/10% FBS into replicate 96-well cell culture plates. Medium was removed 2 h after plating and cells infected with 100 µl of DME/10% FBS containing the indicated amount of Ad vector. Cell culture medium was exchanged for fresh medium (without Ad vector) at 24 h post infection. Cells were fed at 48, 96, 144 and 192 h post infection. Replicate plates were assayed at 48, 96, 144 and 192 h post infection for cell viability using a Cell Titer 96 cell proliferation assay kit (Promega). In this assay, viable cells bioreduce a MTS tetrazolium compound to a colored formazan product that is soluble in cell culture medium. Cell viability was quantitated using a Thermo Max microplate reader (Molecular Devices) at 490 nm.

The same cell proliferation assay was used to test the effect of E1A 243R, E1A 1-80 C+ and controls on a number of human normal and cancer cell lines including normal foreskin fibroblasts (HS68), normal breast (Mg.579, MCF12A and MCF10A), adenocarcinoma of the colon (SW620), Carcinoma of the lung (A549 and NCI 460), adenocarcinoma of the breast (MB231, SPC3 and MCF7), glioblastoma (T98 and SNP-19), adenocarcinoma of the prostate (PC3) and adenocarcinoma of the ovary (ES2).

Mutational Analysis.

Initially three E1A 1-80 genes were synthesized that contained multiple, substitution mutations of potential key amino acid residues within the first (aa 1-13), second (aa 14-27) and third (aa 28-39) regions of the 39 amino acid C-terminus of E1A 1-80 C+. The synthetic genes were made using Gene-Art® (Invitrogen) gene synthesis system. Additionally, a wild-type E1A 1-80 C+ was produced using the GeneArt® system. The region I mutant consists of E1A 1-80 and post E1A C-terminal aa 4Arg substituted with Glu, aa 9Phe substituted with Ala, aa 11Try substituted with Ala and aa 15Asp substituted with His. The region II mutant consists of E1A 1-80 and post-E1A C-terminal aa 24Lys substituted with Asp, aa 27Pro substituted with Ala and aa 29Pro substituted with Ala. The region III mutant consists of E1A 1-80 and post E1A C-terminal aa 34Arg substituted with Asp and aa 37Asp substituted with Arg. The mutations built into region I, II and III mutants are radical mutations designed to likely disrupt any functional secondary structure that may be present.

The synthetic genes were transferred into the Gateway® (Invitrogen) destination Ad vector AdCMV/V5. After transfection into 293A cells, resultant Ad virus vector expressing the various E1A 1-80 C+ derivatives were amplified and purified (Green and Loewenstein, 2005). Titers were normalized by comparison of the optical density of the GeneArt® viral vector preparations with prior preparations of Ad E1A 1-80 C+ with known plaque assay titers.

Example 2

Results

Expression of E1A can Transcriptionally Repress Exogenous and Endogenous HER2 Promoters.

In order to confirm that E1A 243R can repress HER2 expression in human breast cells, MCF-10A cells, which arose by spontaneous immortalization of normal breast epithelial cells (Soule et al., 1990), were co-transfected with a luciferase gene (luc) expressed from the HER2 promoter and with varying levels of a plasmid expressing E1A 243R. FIG. 2A demonstrates that expression from an exogenous HER2 promoter is repressed in a dose-dependent manner by E1A 243R.

A example of HER2 oncogene addiction in human breast cancer cells may be provided by SK-BR-3 cells. SK-BR-3 cells are frequently used as a model of HER2 up-regulation in human breast cancers because SK-BR-3 is amplified 4- to 8-fold for the HER2 gene and SK-BR-3 cells expresses about 128-fold higher levels of HER2RNA than normal breast fibroblasts (Clarke et al., 2000). Therefore, the inventors determined whether expression from the transfected exogenous HER2 promoter could be repressed by E1A 243R in an environment of very high exogenous and endogenous HER2 expression. As shown in FIG. 2B when E1A 243R is expressed in human SK-BR-3 cells, it is able to repress by over 15-fold, a co-transfected "exogenous" HER2 promoter driving a luciferase gene. As anticipated, the E1A repression domain alone (E1A 1-80) efficiently represses transcription from the HER2 promoter construct. This confirms that the E1A repression domain alone is capable of repressing the HER2 promoter in vivo and sets the stage for testing the ability of the repression domain to repress endogenous HER2 expression in up-regulated human cancer cells.

To determine whether the endogenous HER2 promoter can be efficiently repressed in SK-BR-3 cells, E1A 243R and E1A 1-80 were cloned into a replication-deficient Ad vector lacking the E1A, E1B and E3 genes (AdCMV/V5; Invitrogen). In this vector, the cloned E1A 243R or the E1A 1-80 repression domain are expressed from the strong CMV promoter. As shown in FIG. 2, when E1A 243R is expressed from AdCMV in SK-BR-3 cells at either 30 or 300 moi, HER2 expression is reduced over 80% by 36 h post infection (PI). Expression of E1A 1-80 from this Ad vector also repressed expression of HER2 but at a level that was less than anticipated (data not shown).

Alteration of the C-Terminus of E1A 1-80 Dramatically Increases its Expression.

The difference between AdCMV E1A 243R and AdCMV E1A 1-80 is the 163 amino acids removed from the C-terminus of E1A 243R. In an attempt to either stabilize the E1A repression domain or increase its transcription, the inventors elected to add non-specific sequences to the E1A 1-80 N-terminus. Re-cloning E1A 1-80 without a stop codon into the AdCMV/V5 vector provided a facile way to accomplish this task. This adds 39 additional amino acids to the E1A N-terminal repression domain (referred to as Ad E1A 1-80 C+). These sequences although containing a V5 epitope are not expected to provide any specific structure; 23 non-polar, 5 acidic, 5 basic, 3 aromatic and 3 polar residues are included in the additional sequences.

As shown in FIG. 4A, much more (~10- to 20-fold) E1A repression domain protein, as detected by polyclonal antibody directed against E1A CR1, is produced when A549 cells are infected with either 30 or 300 moi of Ad E1A 1-80 C+ than when infected with Ad E1A 1-80. The apparent size of the products does not reflect the 39 additional amino acids present in Ad E1A 1-80 C+ but sequence analysis shows them to be present. Anomalous apparent size by SDS PAGE is commonly observed with E1A proteins.

Although there is clearly more protein produced from Ad E1A 1-80 C+ as compared to Ad E1A 1-80, the reason for this is not apparent. An obvious question is whether the transcript is stabilized or whether transcription is enhanced. FIG. 4B shows the results of parallel pulse-chase experiments using E1A 1-80 or E1A 1-80 C+. As can be seen, the total amount of protein produced by infection with AdCMV E1A 1-80 C+ is more than that produced by infection with AdCMV E1A 1-80 but the rate of turnover is about the same. These findings suggest that the rate of transcription and not product stability accounts for the increased levels of E1A protein as seen in FIG. 3A. However, the inventors have not excluded the possibility that translational control could play a role.

Expression of the Ad E1A Repression Domain Kills SK-BR-3 Cells.

To determine whether transcription-repression of the endogenous HER2 promoter would interfere with the growth of HER2 up-regulated human breast cancer cells, SK-BR-3 cells were infected with varying levels of Ad vector expressing either E1A 243R or E1A 1-80 C+. As controls for potential toxicity from Ad vector infection, two Ad vectors were used: E1A 243R dl1101/dl1108/dl135 (Green et al., 2008; Howe et al., 1990) which is deficient in known E1A 243R functional domains, and LacZ, an unrelated gene, were expressed from the parental vector AdCMV/V5 in parallel wells. Cell viability was measured in replicative plates every 48 h by a cell viability colorimetric assay as described in Materials and Methods.

Figure 5A:
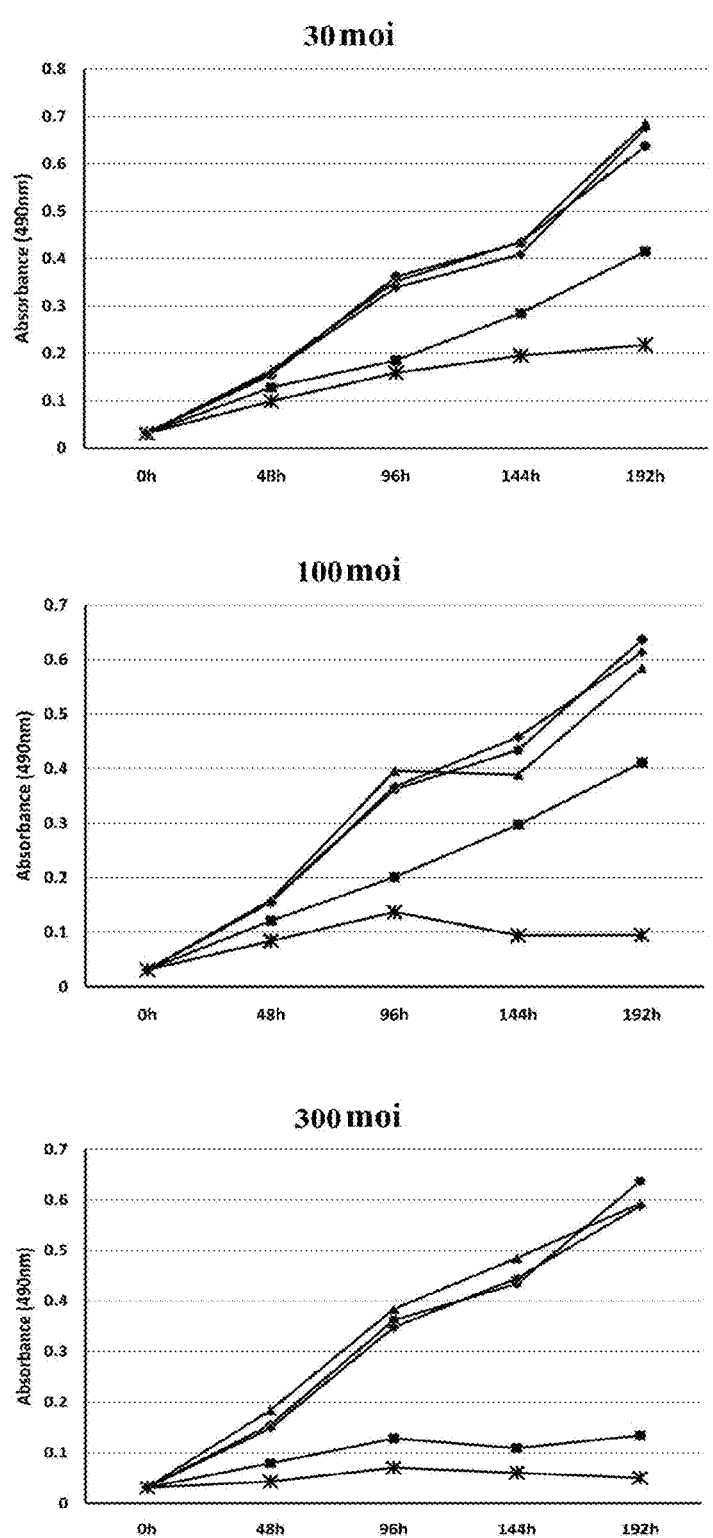
FIGS. 5A-B. E1A 1-80 modified at its C-terminus expressed from an Ad vector inhibits breast cancer cells.

When SK-BR-3 cells were infected at 30 moi (FIG. 5A, first panel), both AdCMV E1A 243R and AdCMV E1A 1-80 C+ clearly exhibited cell killing by 96 h PI. By 192 h PI, AdCMV E1A 1-80 C+ showed pronounced cell killing (~75%) compared to AdCMV E1A 243R (~50%) relative to mock infected or cells infected with control Ad vectors. When the normal human breast cell line HS 579.Mg was infected at 30 moi with the same panel of Ad vectors (FIG. 4B, first panel), no difference between AdCMV 243R or AdCMV E1A 1-80 C+ could be detected relative to mock infected or the Ad vector controls.

Figure 5B:
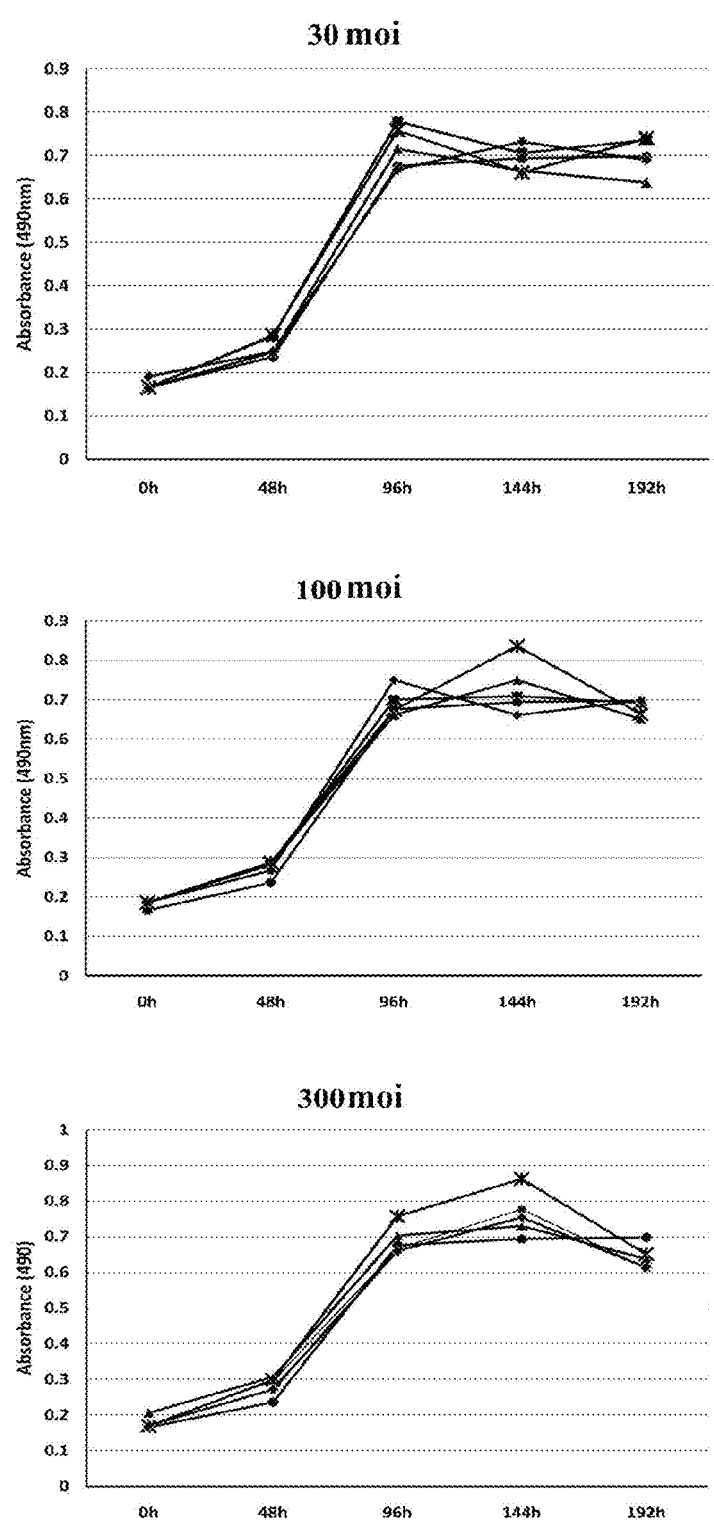

At 100 moi (FIG. 5A second panel), there is a greater difference between the cell-killing efficiencies of AdCMV ETA 243R and AdCMV E1A 1-80 C+. Again, SK-BR-3 cell killing by AdCMV E1A 243R and AdCMV E1A 1-80 C+ is clearly apparent by 96 h PI. However by 144 or 192 h PI, cell killing by AdCMV E1A 1-80 C+ was over 85% whereas cell killing by AdCMV E1A 243R was not substantially different from that observed with infections at 30 moi. Control Ad vectors did not exhibit substantial differences from mock infected. Again, when HS 579.Mg cells were infected with the Ad vectors (FIG. 5B, second panel), no significant cell killing by AdCMV E1A 243R or AdCMV E1A 1-80 C+ could be detected.

At 300 moi (FIG. 5A, third panel), SK-BR-3 cells infected with both AdCMV E1A 243R and AdCMV E1A 1-80 C+ showed very substantial cell-killing. Significantly, even at this high moi, the controls exhibited no cell death when compared with mock infected cells. HS 579.Mg cells (FIG. 5B, third panel) infected with AdCMV 243R or AdCMV 1-80 C+ did not exhibit significant cell killing.

In addition to the HER2 up regulated cell line SK-BR 3, a number of normal and cancer cell lines were tested with the cell proliferation assay for sensitivity to E1A 243R and E1A 1-80 C+ and the controls. None of the four normal cells tested (FIGS. 6A-D) were killed by expression from 300 moi of Ad vectors expressing E1A 243R or E1A 1-80 C+. All of the cancer cell lines tested except for the glioblastoma cell line T98 (FIG. 6L) were killed by expression of E1A 1-80 C+. Cell lines sensitive to E1A 1-80 C+ expression include another glioblastoma cell line SNP-19 (FIG. 6M). Other E1A 1-80 C+ sensitive cell lines were examples of adenocarcinoma of the colon (FIG. 6E), carcinoma of the lung (FIGS. 6F-G), adenocarcinoma of the breast (FIGS. 6H-J), adenocarcinoma of the prostate (FIG. 6N) as well as adenocarcinoma of the ovary (FIG. 6O).

Thus, repression of HER2 in SK-BR-3 cells leads to cell death. E1A 1-80 C+ proved to be a significantly more efficient killer of SK-BR-3 cell at low or moderate moi than E1A 243R. At all moi's tested, neither E1A 243R or E1A 1-80 C+ had a significant effect on the normal HS 579.Mg breast cell line and no cell death could be attributed to infection by Ad vectors alone. Other normal breast cancer cell lines also showed resistance to cell death by expression of the E1A repression domain.

In order to assess which, if any, amino acid residues within the added C-terminal amino acids (aa) of E1A 1-80 C+ are required for enhanced expression and cancer cell-killing activity, a mutational analysis was performed. Ad E1A 1-80 C+, the GeneArt® wild-type E1A 1-80 C+ and the region I, II and III E1A 1-80 C+ mutants were tested in the standard cell proliferation assay at 100 and 300 moi for their ability to kill SK-BR-3 HER2 up-regulated human breast cancer cells. It is clear from these experiments (FIG. 7) that E1A 1-80 C+ and the synthetic E1A 1-80 C+ have approximately the same ability to kill SK-BR-3 human breast cancer cells which express high levels of HER2. Thus, the synthetic E1A 1-80 C+ gene reflects the cancer cell killing activity of its previously cloned archetype. Further, region I and region III mutants of E1A 1-80 C+ retain similar ability to efficiently kill SK-BR-3 cells. However, the region II mutant of E1A 1-80 C+ is severely deficient in its ability to kill SK-BR-3 cells. These data show that some amino acids within region III (aa 14-27) are required for the E1A 1-80 C+ enhanced cancer cell killing ability.

Figure 8:
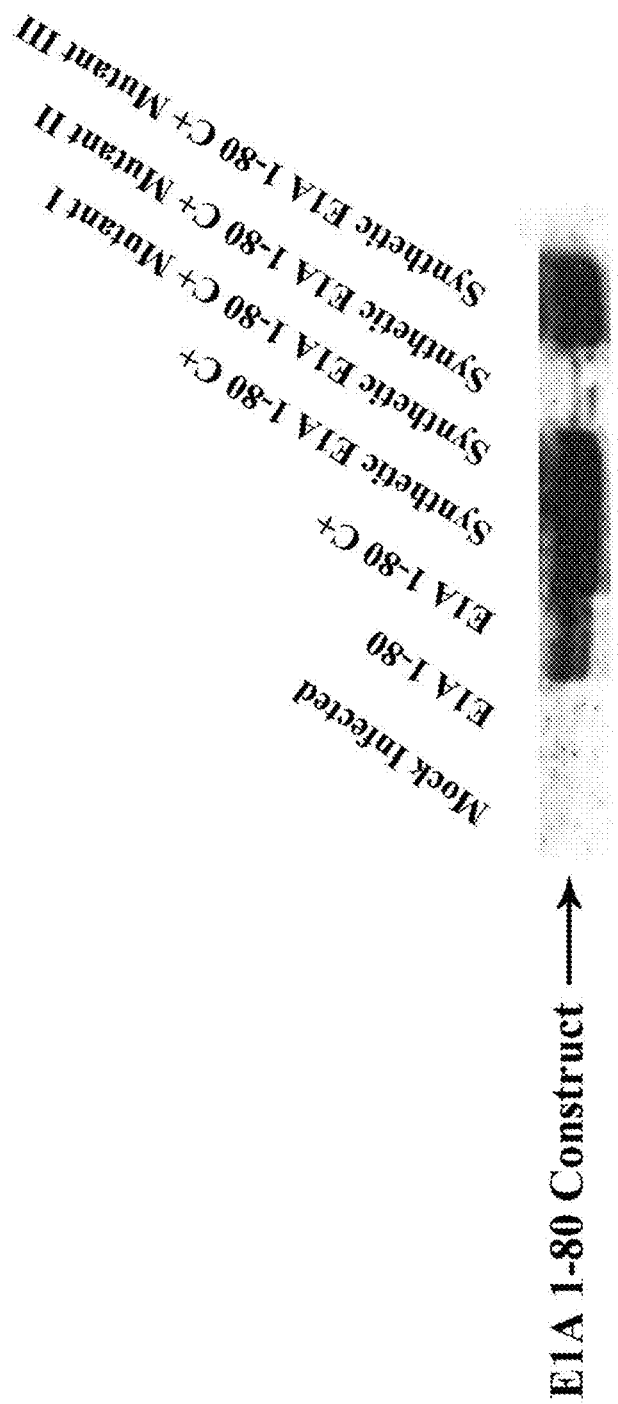
FIG. 8. Human A549 cells were infected with 100 moi of Ad vector expressing the indicated E1A 1-80 C+ construct. Expression of E1A 1-80, E1A 1-80 C+ synthetic GeneArt® E1A 1-80 C+ or synthetic E1A 1-80 C+ mutants was measured by Western analysis using a polyclonal antibody against E1A 289R.

The inventors have previously shown above that E1A 1-80 C+ is expressed at substantially increased levels compared to E1A 1-80 when expressed from a non-replicative ad vector in human A549 cells. Ad E1A 1-80, Ad E1A 1-80 C+, and the Ad vectors expressing the GeneArt® synthetic E1A 1-80 C+ and region I, II and III mutants were used to infect A549 cells at an moi of 100. Cells were harvested 26 h post-infection directly into LDS sample buffer, sonicated briefly to disrupt chromosomal DNA, subjected to LDS gel electrophoresis and proteins transferred to nitrocellulose. The nitrocellulose membranes were subjected to Western blot analysis using a polyclonal antibody against E1A 289R. FIG. 8 shows that E1A 1-80 C+, the GeneArt E1A 1-80 C+, the region I and the region III mutants are expressed at high levels in A549 cells. On the other hand, the E1A 1-80 C+ region II mutant is expressed at much lower levels and E1A 1-80 lacking the 39 additional residues of E1A 1-80 C+ is undetected in this experiment at 100 moi. These results demonstrate that amino acids within region II (aa 14-27) of E1A 1-80 C+ are required for dramatically increased expression levels which correlates with the ability to efficiently kill human breast cancer cells up-regulated for HER2

Example 3

Discussion

The data presented here show that E1A 243R, and more importantly the E1A 1-80 repression domain alone, can efficiently repress the expression of HER2 and when expressed in the HER2 up-regulated SK-BR-3 breast cancer cell line leads to cell death. SK-BR-3 cells were used as a prototype for human breast cancers dependent upon up-regulated HER2 oncogene for growth and survival. The fact that expression of the E1A transcription-repression domain efficiently kills these cells is consistent with the "Oncogene Addiction" hypothesis (Weinstein, 2002). This view holds that, at least in some cancers, once a tumor cell becomes dependent on the continued expression of an oncogene, interference with the expression or function of that oncogene can lead to a return to a normal phenotype or to apoptosis. Oncogenesis, however, is a continuing process that accumulates genetic and epigenetic abnormalities and it is entirely possible that a cancer cell may "evolve" beyond dependence on the original oncogene (Luo et al., 2009). Therefore, if therapy targeting a tumor exhibiting an oncogene addiction is to succeed without the development of resistant tumors, it must be very effective or target more than one aspect of oncogene function. For example, as many as one-third of patients having advanced disease treated with Herceptin fail to respond and further many of those who initially respond show progression of their disease within one year of treatment (Seidman et al., 2001; Miller, 2004). More recently it has been suggested that HER2 up-regulation results in an increase in the number of malignant stem cells which may contribute to failure of treatment (Korkaya et al., 2008) underscoring the potential value of repressing HER2 expression in the treatment of breast cancer.

Transcription-repression of the biosynthesis of a specific oncogene, e.g., HER2, is a strategy that has not been applied as an anti-oncogene therapy, but the SK-BR-3 cell killing assay shown here demonstrates its potential. Herceptin®, a humanized monoclonal antibody directed against the HER2 receptor, has proven its utility, but even a small percentage of unblocked receptors can allow the HER2 signal cascade to stimulate cancer cell growth thus allowing the continued risk of the development of Herceptin® resistant cells. A multi-drug approach to cancer is more likely to succeed since failure of one approach is not likely to impact the other. For example, Herceptin® used in concert with an E1A repressor of HER2 transcription may produce a superior inhibition of HER2 function with less likelihood for the development of resistant tumors.

The relatively small E1A 1-80 repression domain has potential for development into a successful therapy. Other than transcriptional repression, E1A 1-80 does not possess the complicating functions of the multifunctional E1A 243R protein. Its size does not preclude its modification by peptide mimetics nor delivery by methods other than Ad vectors. Further it appears from these preliminary studies to be a more potent killer of SK-BR-3 cells than E1A 243R, probably because it is more efficiently transcribed in its modified E1A 1-80 C+ form. Further examination is needed to access the practicality of using of the E1A transcription-repression domain as a therapy for the treatment of aggressive HER2 up-regulated human breast cancers.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. REFERENCES

The following references, to the extent that they provide exemplary procedural or other details supplementary to those set forth herein, are specifically incorporated herein by reference:

U.S. Pat. No. 4,554,101
U.S. Pat. No. 4,683,195
U.S. Pat. No. 4,683,202
U.S. Pat. No. 4,684,611
U.S. Pat. No. 4,800,159
U.S. Pat. No. 4,879,236
U.S. Pat. No. 4,883,750
U.S. Pat. No. 4,952,500
U.S. Pat. No. 5,217,879
U.S. Pat. No. 5,279,721
U.S. Pat. No. 5,302,523
U.S. Pat. No. 5,322,783
U.S. Pat. No. 5,384,253
U.S. Pat. No. 5,440,013
U.S. Pat. No. 5,446,128
U.S. Pat. No. 5,464,765
U.S. Pat. No. 5,475,085
U.S. Pat. No. 5,506,138
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,610,042
U.S. Pat. No. 5,618,914
U.S. Pat. No. 5,656,610
U.S. Pat. No. 5,670,155
U.S. Pat. No. 5,670,488
U.S. Pat. No. 5,672,681
U.S. Pat. No. 5,674,976
U.S. Pat. No. 5,702,932
U.S. Pat. No. 5,710,245
U.S. Pat. No. 5,736,524
U.S. Pat. No. 5,739,018
U.S. Pat. No. 5,780,448
U.S. Pat. No. 5,789,215
U.S. Pat. No. 5,824,544
U.S. Pat. No. 5,830,725
U.S. Pat. No. 5,840,833
U.S. Pat. No. 5,849,304
U.S. Pat. No. 5,851,826
U.S. Pat. No. 5,858,744
U.S. Pat. No. 5,859,184
U.S. Pat. No. 5,871,982
U.S. Pat. No. 5,871,983
U.S. Pat. No. 5,871,986
U.S. Pat. No. 5,879,934
U.S. Pat. No. 5,888,502
U.S. Pat. No. 5,925,565
U.S. Pat. No. 5,928,906
U.S. Pat. No. 5,929,237
U.S. Pat. No. 5,932,210
U.S. Pat. No. 5,935,819
U.S. Pat. No. 5,945,100
U.S. Pat. No. 5,955,331
U.S. Pat. No. 5,981,274
U.S. Pat. No. 5,994,136
U.S. Pat. No. 5,994,624
U.S. Pat. No. 6,013,516
EPO 320 308
EPO 027 3085
EPO 329 822
GB Appn. 2 202 328
PCT Appln. PCT/US87/00880
PCT Appln. PCT/US89/01025
PCT Appln. WO 88/10315
PCT Appln. WO 89/06700
PCT Appln. WO 90/07641
PCT Appln. WO 89/06700
PCT Appln. WO 90/07641
PCT Appln. WO 9217598
PCT Appln. WO 94/09699
PCT Appln. WO 95/06128
PCT Appln. WO 99/32619
Almendro et al., *J. Immunol.*, 157(12):5411-5421, 1996.
Amado and Chen, *Science*, 285(5428):674-676, 1999.
Angel et al., *Mol. Cell. Biol.*, 7:2256, 1987a.
Angel et al., *Cell*, 49:729, 1987b.
Armentano et al., *Proc. Natl. Acad. Sci. USA*, 87(16):6141-6145, 1990.
Atchison and Perry, *Cell*, 46:253, 1986.
Atchison and Perry, *Cell*, 48:121, 1987.
Ausubel et al., In: *Current Protocols in Molecular Biology*, John, Wiley & Sons, Inc, New York, 1994.
Banerji et al., *Cell*, 27(2 Pt 1):299-308, 1981.
Banerji et al., *Cell*, 33(3):729-740, 1983.
Barany and Merrifield, In: *The Peptides*, Gross and Meienhofer (Eds.), Academic Press, NY, 1-284, 1979.
Bates, *Mol. Biotechnol.*, 2(2):135-145, 1994.
Batra et al., *Am. J. Respir. Cell Mol. Biol.*, 21(2):238-245, 1999.
Battraw and Hall, *Theor. App. Genet.*, 82(2):161-168, 1991.
Bellus, *J. Macromol. Sci. Pure Appl. Chem.*, A31(1): 1355-1376, 1994.
Berkhout et al., *Cell*, 59:273-282, 1989.
Berkner, *Biotechniques*, 6:616-629, 1988.
Bernstein et al., *Nature*, 409:363-366, 2001.
Bett et al., *J. Virololgy*, 67(10):5911-5921, 1993.
Beuzeboc et al., *Bull. Cancer*, 86:544-549, 1999.
Bhattacharjee et al., *J. Plant Bioch. Biotech.*, 6(2):69-73. 1997.
Bilbao et al., *Transplant Proc.*, 31(1-2):792-793, 1999.
Blackwell et al., *Arch. Otolaryngol. Head. Neck Surg.*, 125 (8):856-863, 1999.
Blanar et al., *EMBO J.*, 8:1139, 1989.
Blomer et al., *J. Virol.*, 71(9):6641-6649, 1997.
Bodine and Ley, *EMBO J.*, 6:2997, 1987.
Boshart et al., *Cell*, 41:521, 1985.
Bosher and Labouesse, *Nat. Cell. Biol.*, 2(2):E31-E36, 2000.
Bosze et al., *EMBO J.*, 5(7):1615-1623, 1986.

Boyd et al., *J. Virol.*, 76:1461-1474, 2002.
Braddock et al., *Cell*, 58:269, 1989.
Brennecke et al., *Cell*, 113(1):25-36, 2003.
Brinster et al., *Proc. Natl. Acad. Sci. USA*, 82(13):4438-4442, 1985.
Bulla and Siddiqui, *J. Virol.*, 62:1437, 1986.
Campbell and Villarreal, *Mol. Cell. Biol.*, 8:1993, 1988.
Campbell et al., *Am. Rev. Respir. Dis.*, 130(3):417-423, 1984.
Campere and Tilghman, *Genes and Dev.*, 3:537, 1989.
Campo et al., *Nature*, 303:77, 1983.
Capaldi et al., *Biochem. Biophys. Res. Comm.*, 76:425, 1977.
Caplen et al., *Gene Ther.*, 6(3):454-459, 1999.
Caplen et al., *Gene*, 252(1-2):95-105, 2000.
Carbonelli et al., "*FEMS Microbiol Lett.* 177(1):75-82, 1999.
Case et al., *Proc. Natl. Acad. Sci. USA*, 96(6):2988-2893, 1999.
Celander and Haseltine, *J. Virology*, 61:269, 1987.
Celander et al., *J Virology*, 62:1314, 1988.
Chan et al., *Breast Cancer Res. Treat.*, 91:187-201, 2005.
Chandler et al., *Cell*, 33:489, 1983.
Chandler et al., *Proc. Natl. Acad. Sci. USA*, 94(8):3596-601, 1997.
Chang et al., *Mol. Cell. Biol.*, 9:2153, 1989.
Chatterjee et al., *Proc. Natl. Acad. Sci. USA*, 86:9114, 1989.
Chen and Okayama, *Mol. Cell. Biol.* 7:2745-2752, 1987.
Chen et al., *Genes Dev.*, 10:2438-2451, 1996.
Chen et al., *Nature*, 330:581-583, 1987.
Chillon et al., *J. Virol.*, 73(3):2537-2540, 1999.
Chin et al., *Nature*, 400:468-472, 1999.
Cho et al., *Biotechniques*, 30:562-572, 2001.
Choi et al., *Cell*, 53:519, 1988.
Choudhury et al., *Int. J. Cancer*, 108:71-77, 2003.
Christou et al., *Proc. Natl. Acad. Sci. USA*, 84(12):3962-3966, 1987.
Clarke et al., In: *Diseases of the Breast*, 2$^{nd}$ Ed., 335-354, Harris et al. (Eds.), CK, 2000.
Clay et al., *Pathol. Oncol. Res.*, 5(1):3-15, 1999.
Cocea, *Biotechniques*, 23(5):814-816, 1997.
Coffey et al., *Science*, 282(5392):1332-1334, 1999.
Cohen et al., *J. Cell. Physiol.*, 5:75, 1987.
Cook et al., *Cell*, 27:487-496, 1981.
Costa et al., *Mol. Cell. Biol.*, 8:81, 1988.
Cripe et al., *EMBO J.*, 6:3745, 1987.
Culotta and Hamer, *Mol. Cell. Biol.*, 9:1376, 1989.
Culver et al., *Science*, 256(5063):1550-1552, 1992.
Dandachi et al., *Anticancer Res.*, 24:2401-2406, 2004.
Dandolo et al., *J. Virology*, 47:55-64, 1983.
De Villiers et al., *Nature*, 312(5991):242-246, 1984.
DeLuca et al., *J. Virol.*, 56(2):558-570, 1985.
Derby et al., *Hear Res.*, 134(1-2):1-8, 1999.
Deschamps et al., *Science*, 230:1174-1177, 1985.
D'Halluin et al., *Plant Cell*, 4(12):1495-1505, 1992.
Dorai et al., *Int. J. Cancer*, 82(6):846-852, 1999.
Ebihara et al., *Br. J. Cancer*, 91:119-123, 2004.
Edbrooke et al., *Mol. Cell. Biol.*, 9:1908, 1989.
Edlund et al., *Science*, 230:912-916, 1985.
Elbashir et al., *Genes Dev.*, 5(2):188-200, 2001.
Engel and Kohn, *Front Biosci.*, 4:e26-33, 1999.
Evan et al., *Cell*, 69:119-128, 1992.
Fanidi et al., *Nature*, 359:554-556, 1992.
Fechheimer, et al., *Proc Natl. Acad. Sci. USA*, 84:8463-8467, 1987.
Feldman et al., *Semin. Interv. Cardiol.*, 1(3):203-208, 1996.
Felsher and Bishop, *Proc. Natl. Acad. Sci. USA*, 96:3940-3944, 1999.
Feng and Holland, *Nature*, 334:6178, 1988.
Feng et al., *Nat. Biotechnol.*, 15(9):866-870, 1997.
Firak and Subramanian, *Mol. Cell. Biol.*, 6:3667, 1986.
Fire et al., *Nature*, 391(6669):806-811, 1998.
Fisher et al., *Virology*, 217(1):11-22, 1996.
Flint et al., *Ann. Rev. Gen.*, 23:141-161, 1989.
Fodor et al., *Science*, 251:767-773, 1991.
Foecking and Hofstetter, *Gene*, 45(1):101-105, 1986.
Forster and Symons, *Cell*, 49:211-220, 1987.
Fraley et al., *Proc. Natl. Acad. Sci. USA*, 76:3348-3352, 1979.
Freifelder, In: *Physical Biochemistry Applications to Biochemistry and Molecular Biology*, 2nd Ed. Wm. Freeman and Co., NY, 1982.
Frisch, *Proc. Natl. Acad. Sci. USA*, 88:9077-9081, 1991.
Frohman, In: *PCR Protocols: A Guide To Methods And Applications*, Academic Press, N.Y., 1990.
Fujita et al., *Cell*, 49:357, 1987.
Fujiwara and Tanaka, *Nippon Geka Gakkai Zasshi*, 99(7): 463-468, 1998.
Garoff and Li, *Curr. Opin. Biotechnol.*, 9(5):464-469, 1998.
Garrido et al., *J. Neurovirol.*, 5(3):280-288, 1999.
Gefter et al., *Somatic Cell Genet.*, 3:231-236, 1977.
Gerlach et al., *Nature* (London), 328:802-805, 1987.
Ghosh and Bachhawat, In: *Liver Diseases, Targeted Diagnosis and Therapy Using Specific Receptors and Ligands*, Wu and Wu (Eds.), Marcel Dekker, New York, 87-104, 1991.
Gilles et al., *Cell*, 33:717, 1983.
Gloss et al., *EMBO J.*, 6:3735, 1987.
Gnant et al., *Cancer Res.*, 59(14):3396-403, 1999.
Gnant et al., *J. Natl. Cancer Inst.*, 91(20):1744-1750, 1999.
Godbout et al., *Mol. Cell. Biol.*, 8:1169, 1988.
Goding, In: *Monoclonal Antibodies: Principles and Practice*, 2d ed., Orlando, Fla., Academic Press, 60-61, 65-66, 71-74, 1986.
Goodbourn and Maniatis, *Proc. Natl. Acad. Sci. USA*, 85:1447, 1988.
Goodbourn et al., *Cell*, 45:601, 1986.
Gopal, *Mol. Cell. Biol.*, 5:1188-1190, 1985.
Graham and Prevec *Mol. Biotechnol.*, 3(3):207-220, 1995.
Graham and Van Der Eb, *Virology* 52:456-467, 1973
Green and Loewenstein, *Curr. Prot. Micro.*, 14C.1-14C.19, 2005.
Green et al., *Cell*, 53:921-926, 1988.
Green et al., *Oncogene*, 27:4446-4455, 2008.
Green et al., *Virology*, 371:1-7, 2008.
Greene et al., *Immunology Today*, 10:272, 1989
Grishok et al., *Science*, 287:2494-2497, 2000.
Grosschedl and Baltimore, *Cell*, 41:885, 1985.
Hacia et al., *Nature Genet.*, 14:441-449, 1996.
Haecker et al., *Hum. Gene Ther.*, 7(15):1907-1914, 1996.
Han et al., *Euro. J. Surgical Oncology*, 25:194-198, 1999.
Harland and Weintraub, *J. Cell Biol.*, 101:1094-1099, 1985.
Harlow and Lane, In: *Antibodies: A Laboratory Manual*, Cold Spring Harbor Laboratories, Cold Spring Harbor, N.Y., 1988.
Haslinger and Karin, *Proc. Natl. Acad. Sci. USA*, 82:8572, 1985.
Hauber and Cullen, *J. Virology*, 62:673, 1988.
Hayashi et al., *Neurosci. Lett.*, 267(1):37-40, 1999.
He et al., *Plant Cell Reports*, 14 (2-3):192-196, 1994.
Hen et al., *Nature*, 321:249, 1986.
Hensel et al., *Lymphokine Res.*, 8:347, 1989.
Hermens and Verhaagen, *Prog. Neurobiol.*, 55(4):399-432, 1998.
Herr and Clarke, *Cell*, 45:461, 1986.
Hirochika et al., *J. Virol.*, 61:2599, 1987.
Hirsch et al., *Mol. Cell. Biol.*, 10:1959, 1990.
Holbrook et al., *Virology*, 157:211, 1987.
Holzer et al., *Virology*, 253(1):107-114, 1999.

Horlick and Benfield, *Mol. Cell. Biol.,* 9:2396, 1989.
Hou and Lin, *Plant Physiology,* 111:166, 1996.
Howard et al., *Ann. NY Acad. Sci.,* 880:352-365, 1999.
Howe et al., *Proc. Natl. Acad. Sci. USA,* 87; 5883-5887, 1990.
Huang et al., *Cell,* 27:245, 1981.
Huard et al., *Neuromuscul Disord.,* 7(5):299-313, 1997.
Huettner et al., *Nat. Genet.,* 24:57-60, 2000.
Hug et al., *Mol. Cell. Biol.,* 8:3065, 1988.
Hutvagner and Zamore, *Science,* 297:2056-2060, 2002.
Hutvagner et al., *Science,* 293:834-838, 2001.
Hwang et al., *Mol. Cell. Biol.,* 10:585, 1990.
Imagawa et al., *Cell,* 51:251, 1987.
Imai et al., *J. Virol.,* 72(5):4371-4378, 1998.
Imbra and Karin, *Nature,* 323:555, 1986.
Imler et al., *Mol. Cell. Biol.,* 7:2558, 1987.
Imperiale and Nevins, *Mol. Cell. Biol.,* 4:875, 1984.
Innis et al., *Proc Natl Acad Sci USA,* 85(24):9436-9440, 1988.
Irie et al., *Antisense Nucleic Acid Drug Dev.,* 9(4):341-349, 1999.
Jain et al., *Science,* 297:102-104, 2002.
Jakobovits et al., *Mol. Cell. Biol.,* 8:2555, 1988.
Jameel and Siddiqui, *Mol. Cell. Biol.,* 6:710, 1986.
Jaynes et al., *Mol. Cell. Biol.,* 8:62, 1988.
Johannesson et al., *J. Med. Chem.,* 42(22):4524-4537, 1999.
Johnson et al., In: *Biotechnology And Pharmacy,* Pezzuto et al., (Eds.), Chapman and Hall, New York, 1993.
Johnson et al., *Mol. Cell. Biol.,* 9:3393, 1989.
Johnston et al., *J. Virol.,* 73(6):4991-5000, 1999.
Joyce, *Nature,* 338:217-244, 1989.
Kadesch and Berg, *Mol. Cell. Biol.,* 6:2593, 1986.
Kaeppler et al., *Plant Cell Reports,* 9:415-418, 1990.
Kaneda et al., *Science,* 243:375-378, 1989.
Karin et al., *Mol. Cell. Biol.,* 7:606, 1987.
Katinka et al., *Cell,* 20:393, 1980.
Kato et al., *J. Biol. Chem.,* 266(6):3361-3364, 1991.
Kaufman et al., *Surv. Ophthalmol.,* 43Suppl 1:S91-97, 1999.
Kawamoto et al., *Mol. Cell. Biol.,* 8:267, 1988.
Kay, *Haemophilia,* 4(4):389-392, 1998.
Ketting et al., *Cell,* 99(2):133-141, 1999.
Kiledjian et al., *Mol. Cell. Biol.,* 8:145, 1988.
Kim and Cech, *Proc. Natl. Acad. Sci. USA,* 84:8788-8792, 1987.
Klamut et al., *Mol. Cell. Biol.,* 10:193, 1990.
Klimatcheva et al., *Front Biosci.,* 4:D481-96, 1999.
Kluck et al., *Science,* 275:1132-1136, 1997.
Koch et al., *Mol. Cell. Biol.,* 9:303, 1989.
Kohler and Milstein, *Eur. J. Immunol.,* 6:511-519, 1976.
Kohler and Milstein, *Nature,* 256:495-497, 1975.
Kohut et al., *Am. J. Physiol.,* 275(6 Pt 1):L1089-94, 1998.
Kooby et al., *FASEB J.,* 13(11):1325-1334, 1999.
Korkaya et al., *Oncogene,* 27:6120-6130, 2008.
Kornberg, In: *DNA Replication,* W. H. Freeman and Company, New York, 1992.
Kraus et al., *FEBS Lett.,* 428(3):165-170, 1998.
Kriegler and Botchan, In: *Eukaryotic Viral Vectors,* Gluzman (Ed.), Cold Spring Harbor: Cold Spring Harbor Laboratory, NY, 1982.
Kriegler and Botchan, *Mol. Cell. Biol.,* 3:325, 1983.
Kriegler et al., *Cell,* 38:483, 1984.
Kriegler et al., *Cell,* 53:45, 1988.
Krisky et al., *Gene Ther.,* 5(11):1517-1530, 1998.
Krisky et al., *Gene Ther.,* 5(12):1593-1603, 1998.
Kuhl et al., *Cell,* 50:1057, 1987.
Kunz et al., *Nucl. Acids Res.,* 17:1121, 1989.
Kwoh et al., *Proc. Natl. Acad. Sci. USA,* 86(4):1173-1177, 1989.
Kyte and Doolittle, *J. Mol. Biol.,* 157(1):105-132, 1982.
Lachmann and Efstathiou, *Clin. Sci. (Colch),* 96(6):533-541, 1999.
Lareyre et al., *J. Biol. Chem.,* 274(12):8282-8290, 1999.
Larsen et al., *Proc Natl. Acad. Sci. USA.,* 83:8283, 1986.
Laspia et al., *Cell,* 59:283, 1989.
Latimer et al., *Mol. Cell. Biol.,* 10:760, 1990.
Latta et al., *Mod. Pathol.,* 15:1318-1325, 2002.
Lazzeri, *Methods Mol. Biol.,* 49:95-106, 1995.
Lee et al., *J. Auton. Nerv. Syst.,* 74(2-3):86-90, 1997.
Lee et al., *Korean J. Genet.,* 11(2):65-72, 1989.
Lee et al., *Nature,* 294:228, 1981.
Lee et al., *Nature,* 329(6140):642-645, 1987.
Lee et al., *Nucleic Acids Res.,* 12:4191-206, 1984.
Leibowitz et al., *Diabetes,* 48(4):745-753, 1999.
Lesch, *Biol. Psychiatry,* 45(3):247-253, 1999.
Levenson et al., *Human Gene Therapy,* 9:1233-1236, 1998.
Levine, *Cell,* 88:323-331, 1997.
Levinson et al., *Nature,* 295:79, 1982.
Li et al., *Science,* 275:1943-1947, 1997.
Liang and Pardee, *Nature Reviews Cancer,* 3:869-876, 2003.
Liang, *Biotechniques,* 33:338-346, 2002.
Lillie et al., *Cell,* 50:1091-1100, 1987.
Lin et al., *Mol. Cell. Biol.,* 10:850, 1990.
Loewenstein et al., *Virology,* 351:312-321, 2006.
Lowe et al., *Cell,* 74:957-967, 1993.
Lundstrom, *J. Recept. Signal Transduct. Res.,* 19(1-4):673-686, 1999.
Luo et al., *Cell,* 136:823-836, 2009.
Luria et al., *EMBO J.,* 6:3307, 1987.
Lusky and Botchan, *Proc. Natl. Acad. Sci. USA,* 83:3609, 1986.
Lusky et al., *Mol. Cell. Biol.,* 3:1108, 1983.
Macejak and Sarnow, *Nature,* 353:90-94, 1991.
Majors and Varmus, *Proc. Natl. Acad. Sci. USA,* 80:5866, 1983.
Marienfeld et al., *Gene Ther.,* 6(6):1101-1113, 1999.
Mastrangelo et al., *Cancer Gene Ther.,* 6(5):409-422 1999.
McNeall et al., *Gene,* 76:81, 1989.
Merrifield, *Science,* 232(4748):341-347 1986.
Michel and Westhof, *J. Mol. Biol.,* 216:585-610, 1990.
Miksicek et al., *Cell,* 46:203, 1986.
Miller et al., *Methods Enzymol.,* 217:581-599, 1993.
Miller, *Oncologist,* 9(3):16-19, 2004.
Miyatake et al., *Gene Ther.,* 6(4):564-572, 1999.
Moasser, *Oncogene,* 26:6469-4687, 2007a.
Moasser, *Oncogene,* 26:6577-6592, 2007b.
Moldawer et al., *Shock,* 12(2):83-101, 1999.
Montgomery et al., *Proc. Natl. Acad. Sci. USA,* 95:15502-15507, 1998.
Mordacq and Linzer, *Genes and Dev.,* 3:760, 1989.
Moreau et al., *Nucl. Acids Res.,* 9:6047, 1981.
Moriuchi et al., *Cancer Res.,* 58(24):5731-5737, 1998.
Morrison et al., *J. Gen. Virol.,* 78(Pt 4):873-878, 1997.
Muesing et al., *Cell,* 48:691, 1987.
Nagata et al., *Cancer Cell,* 6:117-127, 2004.
Naldini et al., *Proc. Natl. Acad. Sci. USA,* 93(21):11382-11388, 1996.
Neumann et al., *Proc. Natl. Acad. Sci. USA,* 96(16):9345-9350, 1999.
Ng et al., *Nuc. Acids Res.,* 17:601, 1989.
Nicolau and Sene, *Biochim. Biophys. Acta,* 721:185-190, 1982.
Nicolau et al., *Methods Enzymol.,* 149:157-176, 1987
Nomoto et al., *Gene,* 236(2):259-271, 1999.
Ohara et al., *Proc. Natl. Acad. Sci. USA,* 86:5673-5677, 1989.
Omirulleh et al., *Plant Mol. Biol.,* 21(3):415-28, 1993.

Ondek et al., *EMBO J.*, 6:1017, 1987.
Ornitz et al., *Mol. Cell. Biol.*, 7:3466, 1987.
Palmiter et al., *Nature*, 300:611, 1982.
Parks et al., *J. Virol.*, 71(4):3293-8, 1997.
Pease et al., *Proc. Natl. Acad. Sci. USA*, 91:5022-5026, 1994.
Pech et al., *Mol. Cell. Biol.*, 9:396, 1989.
Pelengaris et al., *Mol. Cell*, 3:565-577, 1999.
Pelletier and Sonenberg, *Nature*, 334:320-325, 1988.
Peng et al., *J. Biol. Chem.*, 280:13148-13152, 2005.
Perales et al., *Proc. Natl. Acad. Sci. USA*, 91:4086-4090, 1994.
Perez-Stable and Constantini, *Mol. Cell. Biol.*, 10:1116, 1990.
Petrof, *Eur. Respir. J.*, 11(2):492-497, 1998.
Picard and Schaffner, *Nature*, 307:83, 1984.
Pignon J et al., *Hum. Mutat.*, 3(2):126-132, 1994.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10:1076, 1990.
Potrykus et al., *Mol. Gen. Genet.*, 199:183-188, 1985.
Potter et al., *Proc. Natl. Acad. Sci. USA*, 81:7161-7165, 1984.
Queen and Baltimore, *Cell*, 35:741, 1983.
Quinn et al., *Mol. Cell. Biol.*, 9:4713, 1989.
Rabinovitch et al., *Diabetes*, 48(6):1223-1229, 1999.
Reddy et al., *J. Virol.*, 72(2):1394-1402, 1998.
Redondo et al., *Science*, 247:1225, 1990.
Reinhart et al., *Nature*, 403:901-906, 2000.
Reinhold-Hurek and Shub, *Nature*, 357:173-176, 1992.
Reisman and Rotter, *Mol. Cell. Biol.*, 9:3571, 1989.
Remington's Pharmaceutical Sciences, 15$^{th}$ ed., pages 1035-1038 and 1570-1580, Mack Publishing Company, Easton, Pa., 1980.
Remington's Pharmaceutical Sciences 15th Edition, 33:624-652, 1990.
Resendez Jr. et al., *Mol. Cell. Biol.*, 8:4579, 1988.
Rhodes et al., *Methods Mol. Biol.*, 55:121-131, 1995.
Ripe et al., *Mol. Cell. Biol.*, 9:2224, 1989.
Rippe et al., *Mol. Cell. Biol.*, 10:689-695, 1990.
Ritter et al., *Clin. Cancer Res.*, 13(16):4909-4919, 2007.
Rittling et al., *Nuc. Acids Res.*, 17:1619, 1989.
Roa et al., *Proc. Natl. Acad. Sci. USA*, 89:7742-7746, 1992.
Robbins and Ghivizzani, *Pharmacol. Ther.*, 80(1):35-47, 1998.
Robbins et al., *Proc. Natl. Acad. Sci. USA*, 95(17):10182-10187 1998.
Robbins et al., *Trends Biotechnol.*, 16(1):35-40, 1998.
Rosen et al., *Cell*, 41:813, 1988.
Ross et al., *Mol. Cell Proteomics*, 3:379-398, 2004.
Rothenberg et al., *Proc. Nat'l Acad. Sci. USA* 105:12480-4, 2008.
Ruley, *Nature*, 304:602-606, 1983.
Sakai et al., *Genes and Dev.*, 2:1144, 1988.
Sambrook et al., *In: Molecular Cloning: A Laboratory Manual*, Vol. 1, Cold Spring Harbor Laboratory Press, Cold Spring Harbor, N.Y., Ch. 7, 7.19-17.29, 1989.
Sarver et al., *Science*, 247:1222-1225, 1990.
Satake et al., *J. Virology*, 62:970, 1988.
Sawai et al., *Mol. Genet. Metab.*, 67(1):36-42, 1999.
Scanlon et al., *Proc. Natl. Acad. Sci. USA*, 88:10591-10595, 1991.
Schaffner et al., *J. Mol. Biol.*, 201:81, 1988.
Schwartz et al., *Cancer Res.*, 63:2913-2922, 2003.
Schwartze, *Z Gesamte Inn. Med.*, 42:336-339, 1987.
Searle et al., *Mol. Cell. Biol.*, 5:1480, 1985.
Seidman et al., *J. Clin. Oncol.*, 19:2587-2595, 2001.
Sharp and Marciniak, *Cell*, 59:229, 1989.
Sharp and Zamore, *Science*, 287:2431-2433, 2000.
Sharp, *Genes Dev.*, 13:139-141, 1999.
Shaul and Ben-Levy, *EMBO J.*, 6:1913, 1987.
Sherman et al., *Mol. Cell. Biol.*, 9:50, 1989.
Shin et al., *Nat. Med.*, 8:1145-1152, 2002.
Shoemaker et al., *Nature Genetics*, 14:450-456, 1996.
Sleigh and Lockett, *J. EMBO*, 4:3831, 1985.
Smith, *Arch. Neurol.*, 55(8):1061-1064, 1998.
Song et al., *J. Biol. Chem.*, 270:23263-23267, 1995.
Song et al., *J. Virol.*, 69:2907-2911, 1995.
Song et al., *Mol. Cell. Biol.*, 17:2186-2193, 1997.
Song et al., *Proc. Natl. Acad. Sci. USA*, 92:10330-10333, 1995.
Soule et al., *Cancer Res.*, 50:6075-6086, 1990.
Spalholz et al., *Cell*, 42:183, 1985.
Spandau and Lee, *J. Virology*, 62:427, 1988.
Spandidos and Wilkie, *EMBO J.*, 2:1193, 1983.
Steck et al., *Nat. Genet.*, 15:356-362, 1997.
Stein et al., *J. Biol. Chem.*, 279:48930-48940, 2004.
Stephens and Hentschel, *Biochem. J.*, 248:1, 1987.
Stephens et al., *Nature*, 431:525-526, 2004.
Stewart and Young, "Solid Phase Peptide Synthesis", 2d. ed., Pierce Chemical Co., 1984.
Stewart et al., *Gene Ther.*, 6(3):350-363, 1999.
Stuart et al., *Nature*, 317:828, 1985.
Sullivan and Peterlin, *Mol. Cell. Biol.*, 7:3315, 1987.
Suzuki et al., *Biochem. Biophys. Res. Commun.*, 252(3):686-690, 1998.
Swartzendruber and Lehman, *J. Cell. Physiology*, 85:179, 1975.
Tabara et al., *Cell*, 99(2):123-132, 1999.
Takebe et al., *Mol. Cell. Biol.*, 8:466, 1988.
Tam et al., *J. Am. Chem. Soc.*, 105:6442, 1983.
Tanaka et al., *Oncogene*, 8:2253-2258, 1993.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor and Stark, *Oncogene*, 20:1803-1815, 2001.
Taylor et al., *J. Biol. Chem.*, 264:15160, 1989.
Thiesen et al., *J. Virology*, 62:614, 1988.
Timiryasova et al., *Int. J. Oncol.*, 14(5):845-854, 1999.
Timiryasova et al., *Oncol. Res.;* 11(3):133-144, 1999.
Treisman, *Cell*, 42:889, 1985.
Tronche et al., *Mol. Biol. Med.*, 7:173, 1990.
Trudel and Constantini, *Genes and Dev.*, 6:954, 1987.
Tsukada et al., *Plant Cell Physiol.*, 30(4) 599-604, 1989.
Tsumaki et al., *J. Biol. Chem.*, 273(36):22861-22864, 1998.
Tur-Kaspa et al., *Mol. Cell. Biol.*, 6:716-718, 1986.
Tyndell et al., *Nuc. Acids. Res.*, 9:6231, 1981.
Vanderkwaak et al., *Gynecol. Oncol.*, 74(2):227-234, 1999.
Vannice and Levinson, *J. Virology*, 62:1305, 1988.
Varis et al., *Cancer Res.*, 62:2625-2629, 2002.
Varis et al., *Int. J. Cancer*, 109:548-553, 2004.
Vasseur et al., *Proc Natl. Acad. Sci. USA*, 77:1068, 1980.
Vogelstein et al., *Nature*, 408(6810):307-310, 2000.
Vogelstein, *Nature*, 348(6303):681-682, 1990.
Wagner et al., *Science*, 260:1510-1513, 1990.
Walker et al., *Nucleic Acids Res.*, 20(7):1691-1696, 1992.
Wang and Calame, *Cell*, 47:241, 1986.
Wang et al., *Gynecol. Oncol.*, 71(2):278-287, 1998.
Weber et al., *Cell*, 36:983, 1984.
Weihl et al., *Neurosurgery*, 44(2):239-252, 1999.
Weinberg et al., *Biochemistry*, 28:8263-8269, 1989.
Weinberger et al., *Mol. Cell. Biol.*, 8:988, 1984.
Weinstein and Joe, *Cancer Res.* 68:3077-3080, 2008.
Weinstein, *Science*, 297:63-64, 2002.
Weisshoff et al., *Eur. J. Biochem.*, 259(3):776-788, 1999.
White et al., *J. Virol.*, 73(4):2832-28340, 1999.
Wilson, *J. Clin. Invest.*, 98(11):2435, 1996.
Wincott et al., *Nucleic Acids Res.*, 23(14):2677-2684, 1995.
Winoto and Baltimore, *Cell*, 59:649, 1989.
Wong et al., *Gene*, 10:87-94, 1980.
Wu and Wallace, *Genomics*, 4:560-569, 1989.
Wu and Wu, *Adv. Drug Delivery Rev.*, 12:159-167, 1993.

Wu and Wu, *J. Biol. Chem.*, 262:4429-4432, 1987.
Wu et al., *Biochem. Biophys. Res. Commun.*, 233(1):221-226, 1997.
Wu, *Chung Hua Min Kuo Hsiao Erh Ko I Hsueh Hui Tsa Chih*, 39(5):297-300, 1998.
Xu et al., *Curr. Biol.*, 13(9):790-795, 2003.
Yamada et al., *Proc. Natl. Acad. Sci. USA*, 96(7):4078-4083, 1999.
Yan et al., *Oncogene*, 2:343-345, 1991.
Yang and Liang, *Mol Biotechnol.*, 3:197-208, 2004.
Yang et al., *Science*, 275:1129-1132, 1997.
Yeung et al., *Gene Ther.*, 6(9):1536-1544, 1999.
Yoon et al., *J. Gastrointest. Surg.*, 3(1):34-48, 1999.
Yu and Zhang, *Biochem. Biophys. Res. Commun.*, 331:851-858, 2005.
Yu et al., *Int. J. Oncol.*, 20:607-610, 2002.
Yu et al., *Mol. Cell. Biol.*, 3:1745-1750, 1991.
Yu et al., *Proc. Natl. Acad. Sci. USA*, 100:1931-1936, 2003.
Yu et al., *Proc. Natl. Acad. Sci. USA*, 87:4499-4503, 1990.
Yu et al., *Proc. Natl. Acad. Sci. USA*, 96:14517-14522, 1999.
Yutzey et al., *Mol. Cell. Biol.*, 9:1397, 1989.
Zeng et al., *Cancer Res.*, 62(13):3630-3635, 2002.
Zhao-Emonet et al., *Biochim. Biophys. Acta*, 1442(2-3):109-119, 1998.
Zheng et al., *J. Gen. Virol.*, 80(Pt 7):1735-1742, 1999.
Zhou et al., *Exp. Hematol*, 21:928-933, 1993.
Zufferey et al., *Nat. Biotechnol.*, 15(9):871-875, 1997.

---

What is claimed is:

1. A method of inhibiting a cancer cell comprising contacting said cancer cell with a polypeptide characterized as:
   (a) comprising residues 1-80 of adenovirus E1A (SEQ ID NO: 1);
   (b) substantially lacking E1A sequences C-terminal to residue 80; and
   (c) comprising a non-E1A stabilization sequence located C-terminal to residue 80.

2. The method of claim 1, wherein said cancer cell overexpresses HER2-Neu as compared to a non-cancer cell.

3. The method of claim 1, wherein said cancer cell does not overexpress HER2-Neu as compared to a non-cancer cell.

4. The method of claim 1, wherein said cancer cell is a breast cancer cell.

5. The method of claim 1, wherein said cancer cell is a lung cancer cell, an ovarian cancer cell, a brain cancer cell, or a prostate cancer cell.

6. The method of claim 1, wherein said cancer cell is a carcinoma, an adenocarcinoma or a glioblastoma.

7. The method of claim 1, wherein said non-E1A stabilization sequence is about 40 residues in length.

8. The method of claim 4, wherein said non-E1A stabilization sequence comprises residues 14-27 of SEQ ID NO: 3 or residues 1-27 of SEQ ID NO: 3.

9. The method of claim 4, wherein said non-E1A stabilization sequence comprises of SEQ ID NO: 3.

10. The method of claim 1, wherein said polypeptide lacks E1A sequences other than SEQ ID NO: 1.

11. The method of claim 1, wherein contacting comprises introducing into said cell a viral vector comprising a polynucleotide segment encoding said polypeptide under the control of a promoter active in said cell.

12. The method of claim 1, wherein contacting comprises introducing into said cell a non-viral vector comprising an polynucleotide segment encoding said polypeptide under the control of a promoter active in said cell.

13. The method of claim 12, wherein said non-viral vector is delivered in a lipid delivery vehicle.

14. The method of claim 1, wherein said polypeptide further comprises a cell penetrating domain.

15. The method of claim 1, further comprising contacting said cancer cell with a second anti-cancer treatment.

16. The method of claim 1, further comprising contacting said polypeptide with said cancer cell at least a second time.

17. The method of claim 1, wherein said cancer cell is a multi-drug resistant cancer cell.

18. The method of claim 1, wherein inhibiting comprises slowing the growth of said cancer cell.

19. The method of claim 1, wherein inhibiting comprises killing said cancer cell.

20. The method of claim 17, wherein killing comprises inducing apoptosis in said cancer cell.

21. The method of claim 1, further comprises assessing HER2-Neu expression prior to contacting.

22. A method of treating a subject with cancer comprising contacting a cancer cell in said subject with an polypeptide characterized as:

(a) comprising residues 1-80 of adenovirus E1A (SEQ ID NO: 1);
(b) substantially lacking E1A sequences C-terminal to residue 80; and
(c) comprising a non-E1A stabilization sequence located C-terminal to residue 80.

23. A method of increasing remission time in a subject with cancer that is in remission comprising contacting a cancer cell in said subject with an polypeptide characterized as:
(a) comprising residues 1-80 of adenovirus E1A (SEQ ID NO: 1);
(b) substantially lacking E1A sequences C-terminal to residue 80; and
(c) comprising a non-E1A stabilization sequence located C-terminal to residue 80.

* * * * *

UNITED STATES PATENT AND TRADEMARK OFFICE
CERTIFICATE OF CORRECTION

PATENT NO. : 8,716,014 B2
APPLICATION NO. : 13/552407
DATED : May 6, 2014
INVENTOR(S) : Maurice Green and Paul M. Loewenstein Page 1 of 1

It is certified that error appears in the above-identified patent and that said Letters Patent is hereby corrected as shown below:

In title page, item (75) Inventors, delete "Paul M. Loewenstein, Sain Louis, MO (US)" and replace with --Paul M. Loewenstein, Saint Louis, MO (US)-- therefor.

In the Claims

Claim 9, column 87, line 65, delete "comprises of" and replace with --comprises-- therefor.

Claim 20, column 88, line 61, delete "claim 17," and replace with --claim 19,-- therefor.

Signed and Sealed this
Nineteenth Day of August, 2014

Michelle K. Lee
*Deputy Director of the United States Patent and Trademark Office*